United States Patent
Basford et al.

(10) Patent No.: US 8,754,072 B2
(45) Date of Patent: Jun. 17, 2014

(54) SALTS AND POLYMORPHS OF 8-FLUORO-2-{4-[(METHYLAMINO)METHYL]PHENYL}-1,3,4,5-TETRAHYDRO-6H-AZEPINO[5,4,3-CD]INDOL-6-ONE

(75) Inventors: Patricia Ann Basford, Sandwich (GB); Anthony Michael Campeta, Ledyard, CT (US); Adam Gillmore, Sandwich (GB); Matthew Cameron Jones, Sandwich (GB); Eleftherios Kougoulos, Morrisville, NC (US); Suman Luthra, Groton, CT (US); Robert Walton, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/522,549

(22) PCT Filed: Feb. 10, 2011

(86) PCT No.: PCT/IB2011/050571
§ 371 (c)(1),
(2), (4) Date: Jul. 17, 2012

(87) PCT Pub. No.: WO2011/098971
PCT Pub. Date: Aug. 18, 2011

(65) Prior Publication Data
US 2012/0302550 A1   Nov. 29, 2012

Related U.S. Application Data

(60) Provisional application No. 61/304,277, filed on Feb. 12, 2010.

(51) Int. Cl.
*C07D 487/06*   (2006.01)
*A61K 31/55*   (2006.01)

(52) U.S. Cl.
USPC ..................... 514/212.06; 540/520

(58) Field of Classification Search
USPC ..................... 540/520; 514/212.06
See application file for complete search history.

(56) References Cited

U.S. PATENT DOCUMENTS

| 6,495,541 | B1 | 12/2002 | Webber et al. |
| 6,977,298 | B2 | 12/2005 | Webber et al. |
| 7,268,126 | B2 | 9/2007 | Liu et al. |
| 7,323,562 | B2 | 1/2008 | Ma et al. |
| 7,351,701 | B2 | 4/2008 | Helleday et al. |
| 7,429,578 | B2 | 9/2008 | Webber et al. |
| 7,531,530 | B2 | 5/2009 | Helleday et al. |
| 2006/0074073 | A1 | 4/2006 | Steinfeldt et al. |

FOREIGN PATENT DOCUMENTS

WO   WO 2004/087713   10/2004

*Primary Examiner* — Bruck Kifle
(74) *Attorney, Agent, or Firm* — Swanson & Bratschun, L.L.C.

(57) ABSTRACT

The present invention relates to novel polymorphic forms of 8-fluoro-2-{4-[(methylamino)methyl]phenyl}-1,3,4,5-tetrahydro-6H-azepino[5,4,3-cd]indol-6-one, and to processes for their preparation. Such polymorphic forms may be a component of a pharmaceutical composition and may be used to treat a mammalian disease condition mediated by poly(ADP-ribose) polymerase activity including the disease condition such as cancer.

21 Claims, 38 Drawing Sheets

SALTS AND POLYMORPHS OF 8-FLUORO-2-{4-[(METHYLAMINO)METHYL]PHENYL}-1,3,4,5-TETRAHYDRO-6H-AZEPINO[5,4,3-CD]INDOL-6-ONE

This application is a 35 U.S.C. §371 national phase application of PCT/IB2011/050571 (WO 2011/098971 A1), filed Feb. 10, 2011. PCT/IB2011/050571 claims the benefit of U.S. Patent Application No. 61/304,277, filed Feb. 12, 2010, which are hereby incorporated by reference in their entirety.

RELATED APPLICATIONS

This application claims the benefit of U.S. Patent Application No. 61/304,277, filed Feb. 12, 2010, which is hereby incorporated by reference in its entirety.

FIELD

The present invention relates to novel polymorphic salts of 8-fluoro-2-{4-[(methylamino)methyl]phenyl}-1,3,4,5-tetrahydro-6H-azepino[5,4,3-cd]indol-6-one, and to methods for their preparation. The invention is also directed to pharmaceutical compositions containing at least one polymorphic form and to the therapeutic and/or prophylactic use of such polymorphic forms and compositions.

BACKGROUND

The compound 8-fluoro-2-{4-[(methylamino)methyl]phenyl}-1,3,4,5-tetrahydro-6H-azepino[5,4,3-cd]indol-6-one ("Compound 1")

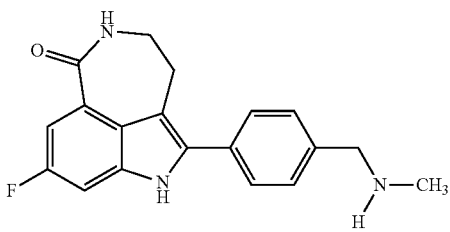

is a small molecule inhibitor of poly(ADP-ribose) polymerase (PARP). Compound 1, and methods of making it, are described in U.S. Pat. Nos. 6,495,541; 6,977,298; 7,429,578 and 7,323,562. Certain salts and polymorphs thereof, of Compound 1, are disclosed in U.S. Pat. No. 7,268,126 and in International Patent Publication No. WO 04/087713. Other publications describing Compound 1 and uses thereof include U.S. Patent Application Publication No. 2006-0074073, and U.S. Pat. Nos. 7,351,701 and 7,531,530.

PARP is a family of nuclear enzymes responsible for ADP-ribosylation (a post-translational protein modification) in which poly(ADP-ribosyl)transferases transfer the ADP-ribose moiety from $NAD^+$ onto specific amino acid side chains on nuclear target proteins such as histones and DNA repair enzymes and/or onto previously attached ADP-ribose units. In humans the PARP family encompasses 17 enzymes of which PARP-1 is the best-characterized (Otto H, Reche P A, Bazan F et al, In silico characterization of the family of PARP-like poly(ADP-ribosyl)transferases (pARTs), BMC Genomics 2005; 6:139). Pharmacology studies have shown that Compound 1 is an inhibitor of PARP-1 (Ki=1.4 nM) and PARP-2 (Ki=0.17 nM).

PARP-1 is involved in DNA homeostasis through binding to DNA breaks and attracting DNA repair proteins to the site of DNA damage. PARP-1 through the addition of ADP-ribose units on target proteins provides the energetic resources necessary for chromatin relaxation and the DNA repair process. These actions promote and facilitate DNA repair. Depending on the extent of DNA damage PARP-1 activation and subsequent poly(ADP-ribosyl)ation mediate the repair of damaged DNA or induce cell death. When DNA damage is moderate, PARP-1 plays a significant role in the DNA repair process. Conversely, in the event of massive DNA damage, excessive activation of PARP-1 depletes the cellular ATP pool, which ultimately leads to cell mortality by necrosis (Tentori L, Portarena I, Graziani G, Potential applications of poly(ADP-ribose) polymerase (PARP) inibitors, Pharmacol Res 2002; 45:73-85).

In cancer therapy, many useful drugs as well as ionizing radiation exert their therapeutic effect through DNA damage. Enzyme-mediated repair of single- or double-strand DNA breaks is a potential mechanism of resistance to radiotherapy or cytotoxic drugs whose mechanism of action depends on DNA damage. Inhibition of DNA repair pathway enzymes is thus a strategy for the potentiation of anticancer agents. Inhibition of PARP-1 has shown to potentiate the activity of DNA-damaging agents and ionizing radiation in vivo and in vitro. Accordingly, PARP has been identified as a therapeutic target for cancer therapy in combination with DNA damaging agents. (Tentori L, Leonetti C, Scarsella M, et al, Systemic administration of GPA 15427, a novel poly(ADP-ribose) polymerase-1 inhibitor, increases the antitumor activity of temozolomide against intracranial melanoma, glioma, lymphoma, Clin Cancer Res 2003; 9:5370-9. Satoh M S, Poirier GG, Lindahl T, NAD(+)-dependent repair of damaged DNA by human cell extracts, J Biol Chem 1993; 268:5480-7.)

In addition to the potential role as chemopotentiator or radiosensitizer agents, more recent evidence has emerged of sensitivity of cell lines, homozygous for either the BRCA1 or BRCA2 mutation, to a PARP inhibitor alone. (Bryant H E, Schultz N, Thomas H D, et al, Specific killing of BRCA-2 deficient tumors with inhibitors of poly(ADP-ribose) polymerase, Nature 2005; 434:913-7. Farmer H, McCabe N, Lord C J, et al, Targeting the DNA repair defect in BRCA mutant cells as a therapeutic strategy, Nature 2005; 434:917-21.) Preliminary clinical data from a Phase I study with a single-agent PARP inhibitor has recently been published (Yap T A, Boss D S, Fong M, et al, First in human phase I pharmacokinetic (PK) and pharmacodynamic (PD) study of KU-0059436 (Ku), a small molecule inhibitor of poly ADP-ribose polymerase (PARP) in cancer patients (p) including BRCA 1/2 mutation carriers, (J Clin Oncol 2007; 25 (Supplement June 20):3529).

It is desirable to have crystalline salts and polymorphic forms thereof that possess properties amenable to reliable formulation and manufacture.

SUMMARY OF THE INVENTION

Some embodiments disclosed herein provide a maleate salt of 8-fluoro-2-{4-[(methylamino)methyl]phenyl}-1,3,4,5-tetrahydro-6H-azepino[5,4,3-cd]indol-6-one. In some embodiments, the maleate salt is crystalline. In some embodiments, the maleate salt is a crystalline anhydrous salt.

In some embodiments, the maleate salt has a powder X-ray diffraction pattern comprising one or more or two or more peaks at diffraction angles (2θ) selected from the group consisting of 6.0±0.2, 20.3±0.2, and 21.7±0.2. In some embodiments, said powder X-ray diffraction pattern is obtained using copper K-alpha$_1$ X-rays at a wavelength of 1.5406 Ångstroms. In some embodiments, the maleate salt has a powder X-ray diffraction pattern comprising peaks at diffraction angles (2θ) of 6.0±0.2, 20.3±0.2, and 21.7±0.2, wherein said powder X-ray diffraction pattern is obtained using copper K-alpha$_1$ X-rays at a wavelength of 1.5406 Ångstroms. In further embodiments, the salt has a powder X-ray diffraction pattern comprising peaks at diffraction angles (2θ) essentially the same as shown in FIG. 1. In additional embodiments, the salt has a differential scanning calorimetry thermogram essentially the same as shown in FIG. 2. In some embodiments, the salt is a substantially pure polymorph of maleate polymorph Form A.

In some embodiments, the maleate salt has a powder X-ray diffraction pattern comprising one or more or two or more peaks at diffraction angles (2θ) selected from the group consisting of 7.5±0.2, 11.3±0.2, and 24.3±0.2. In some embodiments, said powder X-ray diffraction pattern is obtained using copper K-alpha$_1$ X-rays at a wavelength of 1.5406 Ångstroms. In some embodiments, the maleate salt has a powder X-ray diffraction pattern comprising peaks at diffraction angles (2θ) of 7.5±0.2, 11.3±0.2, and 24.3±0.2, wherein said powder X-ray diffraction pattern is obtained using copper K-alpha$_1$ X-rays at a wavelength of 1.5406 Ångstroms. In further embodiments, the maleate salt has a powder X-ray diffraction pattern comprising peaks at diffraction angles (2θ) essentially the same as shown in FIG. 3 or FIG. 4. In some embodiments, the maleate salt has a solid state NMR spectrum comprising one or more or two or more $^{13}$C chemical shifts selected from the group consisting of 171.3±0.2, 112.4±0.2, and 43.8±0.2 ppm. In some embodiments, the maleate salt has a solid state NMR spectrum comprising $^{13}$C chemical shifts at 171.3±0.2, 112.4±0.2, and 43.8±0.2 ppm. In further embodiments, the maleate salt has a solid state NMR spectrum comprising $^{13}$C chemical shifts at positions essentially the same as shown in FIG. 5. In some embodiments, the maleate salt has a solid state NMR spectrum comprising a $^{19}$F chemical shift at −123.1±0.2 ppm. In further embodiments, the maleate salt has a solid state NMR spectrum comprising $^{19}$F chemical shifts at positions essentially the same as shown in FIG. 6. In some embodiments, the maleate salt has a powder X-ray diffraction pattern comprising: one or more or two or more or three peaks at diffraction angles (2θ) selected from the group consisting of 7.5±0.2, 11.3±0.2, and 24.3±0.2 obtained using copper K-alpha$_1$ X-rays at a wavelength of 1.5406 Ångstroms; and: 1) a solid state NMR spectrum comprising one or more or two or more or three $^{13}$C chemical shifts selected from the group consisting of 171.3±0.2, 112.4±0.2, and 43.8±0.2 ppm; and/or 2) a solid state NMR spectrum comprising a $^{19}$F chemical shift at −123.1±0.2 ppm. In additional embodiments, the salt has a differential scanning calorimetry thermogram essentially the same as shown in FIG. 7. In additional embodiments, the salt has a dynamic vapor sorption isotherm essentially the same as shown in FIG. 8. In some embodiments, the maleate salt has one or more FT-IR spectral peaks as shown in Table 6. In some embodiments, the maleate salt has one or more FT-Raman spectral peaks as shown in Table 7. In some embodiments, the maleate salt is a substantially pure polymorph of maleate polymorph Form B. Some embodiments provide for a mixture of maleate polymorph Form A and maleate polymorph Form B.

Additional embodiments provide a pharmaceutical composition comprising a maleate salt (e.g., maleate polymorph Form A or maleate polymorph Form B or a mixture thereof). In some embodiments, the pharmaceutical composition comprises a solid dosage form (e.g., a tablet). In some embodiments, the pharmaceutical composition comprises approximately 10%-25% of the maleate salt, approximately 45%-60% microcrystalline cellulose, approximately 20%-35% dicalciaum phosphate anhydrous, approximately 0.1%-5% sodium starch glycolate (type A), and approximately 0.1%-5% magnesium stearate. In some embodiments, the pharmaceutical composition comprises approximately 17.18% of the maleate salt, approximately 52.55% microcrystalline cellulose, approximately 26.27% dicalciaum phosphate anhydrous, approximately 3% sodium starch glycolate (type A), and approximately 1% magnesium stearate. Some embodiments provide a method of treating a mammalian disease condition mediated by poly(ADP-ribose) polymerase activity, the method comprising administering to a mammal in need thereof a therapeutically effective amount of a pharmaceutical composition comprising a maleate salt (e.g., maleate polymorph Form A or maleate polymorph Form B or a mixture thereof). Some embodiments provide a method of treating cancer in a mammal, the method comprising administering to the mammal a therapeutically effective amount of a pharmaceutical composition comprising a maleate salt (e.g., maleate polymorph Form A or maleate polymorph Form B or a mixture thereof).

Some embodiments disclosed herein relate to a camsylate salt of 8-fluoro-2-{4-[(methylamino)methyl]phenyl}-1,3,4,5-tetrahydro-6H-azepino[5,4,3-cd]indol-6-one. In some embodiments, the camsylate salt is crystalline. In some embodiments, the camsylate salt is a crystalline anhydrous salt. In some embodiments, the camsylate is S-camsylate. In other embodiments, the camsylate is R-camsylate.

In some embodiments, the camsylate salt has a powder X-ray diffraction pattern comprising one or more or two or more or three or more or four or more peaks at diffraction angles (2θ) selected from the group consisting of 6.0±0.2, 12.2±0.2, 12.7±0.2, 14.8±0.2, 16.7±0.2, and 22.4±0.2. In some embodiments, the camsylate salt has a powder X-ray diffraction pattern comprising one or more or two or more or three peaks at diffraction angles (2θ) selected from the group consisting of 12.2±0.2, 14.8±0.2, and 22.4±0.2. In some embodiments, the powder X-ray diffraction pattern is obtained using copper K-alpha$_1$ X-rays at a wavelength of 1.5406 Ångstroms. In further embodiments, the camsylate salt has a powder X-ray diffraction pattern comprising peaks at diffraction angles (2θ) essentially the same as shown in FIG. 9 or 10. In some embodiments, the camsylate salt has a solid state NMR spectrum comprising one or more or two or more $^{13}$C chemical shifts selected from the group consisting of 213.4±0.2, 171.8±0.2, and 17.3±0.2 ppm. In some embodiments, the camsylate salt has a solid state NMR spectrum comprising $^{13}$C chemical shifts at 213.4±0.2, 171.8±0.2, and 17.3±0.2 ppm. In further embodiments, the camsylate salt has a solid state NMR spectrum comprising $^{13}$C chemical shifts at positions essentially the same as shown in FIG. 11. In some embodiments, the camsylate salt has a solid state NMR spectrum comprising one or more $^{19}$F chemical shifts selected from the group consisting of −118.9±0.2 and −119.7 ppm±0.2. In some embodiments, the camsylate salt has a solid state NMR spectrum comprising $^{19}$F chemical shifts at −118.9±0.2 and −119.7 ppm±0.2. In further embodiments, the camsylate salt has a solid state NMR spectrum comprising $^{19}$F chemical shifts at positions essentially the same as shown in FIG. 12. In some embodiments, the camsylate salt has a powder X-ray diffraction pattern comprising one or more or two or more or three or more or four or more or five peaks at diffraction angles (2θ) selected from the group consisting of 6.0±0.2, 12.2±0.2, 12.7±0.2, 14.8±0.2 16.7±0.2, and 22.4±0.2 obtained using copper K-alpha$_1$ X-rays at a wavelength of 1.5406 Ångstroms; and 1) a solid state NMR spectrum comprising one or more or two or more or three $^{13}$C chemical shifts selected from the group consisting of 213.4±0.2, 171.8±0.2, and 17.3±0.2 ppm; and/or 2) a solid state NMR spectrum comprising one or more or two $^{19}$F chemical shifts selected from the group consisting of −118.9±0.2 and −119.7 ppm±0.2. In additional embodiments, the salt has a differential scanning calorimetry thermogram essentially the same as shown in FIG. 13. In additional embodiments, the salt has a dynamic vapor sorption isotherm essentially the same as shown in FIG. 14. In some embodiments, the camsylate salt has one or more FT-IR spectral peaks as shown in Table 12. In some embodiments, the camsylate salt has one or more FT-Raman spectral peaks as shown in Table 13. In some embodiments, the salt is a substantially pure polymorph of S-camsylate polymorph Form A.

In some embodiments, the camsylate salt has a powder X-ray diffraction pattern comprising peaks at diffraction angles (2θ) essentially the same as shown in FIG. 15. In some embodiments, the salt is a substantially pure polymorph of S-camsylate polymorph Form B. Some embodiments provide for a mixture of S-camsylate polymorph Form A and S-camsylate polymorph Form B.

In some embodiments, the camsylate salt has a powder X-ray diffraction pattern comprising peaks at diffraction angles (2θ) essentially the same as shown in FIG. 18. In some embodiments, the camsylate salt has a powder X-ray diffraction pattern comprising one or more or two or more or three peaks at diffraction angles (2θ) selected from the group consisting of 15.0±0.2, 21.8±0.2, and 24.7±0.2. In some embodiments, the camsylate salt has a solid state NMR spectrum comprising one or more $^{13}$C chemical shifts as shown in Table 16. In some embodiments, the camsylate salt has one or more $^{19}$F chemical shifts as shown in Table 17. In some embodiments, the camsylate salt has a solid state NMR spectrum comprising two or more $^{13}$C chemical shifts selected from the group consisting of 211.7±0.2, 132.5±0.2, and 19.4±0.2 ppm. In some embodiments, the camsylate salt has a solid state NMR spectrum comprising $^{13}$C chemical shifts at 211.7±0.2, 132.5±0.2, and 19.4±0.2 ppm. In some embodiments, the camsylate salt has a solid state NMR spectrum comprising a $^{19}$F chemical shift at −118.5±0.2. In some embodiments, the camsylate salt has one or more FT-IR spectral peaks as shown in Table 18. In some embodiments, the camsylate salt has one or more FT-Raman spectral peaks as shown in Table 19. In some embodiments, the salt is a substantially pure polymorph of S-camsylate polymorph Form C. Some embodiments provide for a mixture of two or more of S-camsylate polymorph Form A, S-camsylate polymorph Form B and S-camsylate polymorph Form C.

In some embodiments, the salt is a substantially pure polymorph of R-camsylate polymorph Form A. Further embodiments provide additional camsylate salts. The salts can have various R:S ratios of camphor sulfonic acid, e.g., a 1R:1S-camsylate salt, a 1R:9S-camsylate salt, a 1R:3S-camsylate salt, and a 1R:7S-camsylate salt.

Further embodiments provide for an amorphous form of the S-camsylate salt of Compound 1.

Additional embodiments provide a pharmaceutical composition comprising an camsylate salt described herein (e.g., S-camsylate polymorph Form A, S-camsylate polymorph Form B, S-camsylate polymorph Form C, R-camsylate polymorph Form A or a mixture thereof). In some embodiments, the pharmaceutical composition comprises a solid dosage form (e.g., a tablet). In some embodiments, the pharmaceutical composition comprises approximately 10%-25% of the camsylate salt, approximately 45%-60% microcrystalline cellulose, approximately 20%-35% dicalciaum phosphate anhydrous, approximately 0.1%-5% sodium starch glycolate (type A), and approximately 0.1%-5% magnesium stearate. In some embodiments, the pharmaceutical composition comprises approximately 17.18% of the camsylate salt, approximately 52.55% microcrystalline cellulose, approximately 26.27% dicalciaum phosphate anhydrous, approximately 3% sodium starch glycolate (type A), and approximately 1% magnesium stearate. Some embodiments provide a method of treating a mammalian disease condition mediated by poly (ADP-ribose) polymerase activity, the method comprising administering to a mammal in need thereof a therapeutically effective amount of a pharmaceutical composition comprising an camsylate salt described herein (e.g., S-camsylate polymorph Form A, S-camsylate polymorph Form B, S-camsylate polymorph Form C, R-camsylate polymorph Form A or a mixture thereof). Some embodiments provide a method of treating cancer in a mammal, the method comprising administering to the mammal a therapeutically effective amount of a pharmaceutical composition comprising an S-camsylate salt described herein (e.g., S-camsylate polymorph Form A, S-camsylate polymorph Form B, S-camsylate polymorph Form C, R-camsylate polymorph Form A or a mixture thereof).

Further embodiments provide a pharmaceutical composition comprising two or more polymporph forms or salts described herein.

Additional embodiments provide methods of treating a mammalian disease condition mediated by poly(ADP-ribose) polymerase activity, the method comprising administering to a mammal in need thereof a therapeutically effective amount of a pharmaceutical composition described herein in combination with a therapeutically effective amount of one or more substances, such as anti-tumor agents, anti-angiogenesis agents, signal transduction inhibitors, and antiproliferative agents, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments provide a method of treating cancer in a mammal, the method comprising administering to the mammal a therapeutically effective amount of a pharmaceutical composition described herein in combination with a therapeutically effective amount of one or more substances, such as anti-tumor agents, anti-angiogenesis agents, signal transduction inhibitors, and antiproliferative agents, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Definitions

As used herein, the term "Compound 1" refers to the chemical compound 8-fluoro-2-{4-[(methylamino)methyl] phenyl}-1,3,4,5-tetrahydro-6H-azepino[5,4,3-cd]indol-6-one, also represented by the structural formula:

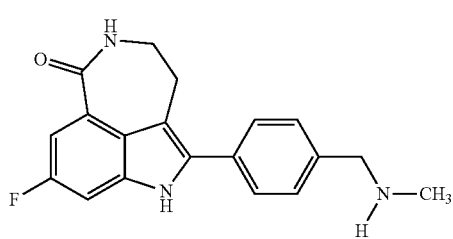

The term "active agent" or "active ingredient" refers to a polymorphic form of Compound 1, or to a solid form that comprises two or more polymorphic forms or amorphous form of Compound 1.

As used herein, the term "substantially pure" with reference to a particular polymorphic form (or to a mixture of two or more polymorphic forms) of Compound 1 indicates the polymorphic form (or a mixture) includes less than 10%, preferably less than 5%, preferably less than 3%, preferably less than 1% by weight of impurities, including other polymorphic forms of Compound 1. Such purity may be determined, for example, by powder X-ray diffraction.

As used herein, the term "polymorph" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore X-ray powder diffraction can be used to identify different polymorphs, or a solid form that comprises more than one polymorph, in a reproducible and reliable way (S. Byrn et al, Pharmaceutical Solids: A Strategic Approach to Regulatory Considerations, Pharmaceutical research, Vol. 12, No. 7, p. 945-954, 1995; J. K. Haleblian and W. McCrone, Pharmacetical Applications of Polymorphism, Journal of Pharmaceutical Sciences, Vol. 58, No. 8, p. 911-929, 1969). Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The term "powder X-ray diffraction pattern" or "PXRD pattern" refers to the experimentally observed diffractogram or parameters derived therefrom. Powder X-ray diffraction patterns are typically characterized by peak position (abscissa) and peak intensities (ordinate). The term "peak intensities" refers to relative signal intensities within a given X-ray diffraction pattern. Factors which can affect the relative peak intensities are sample thickness and preferred orientation (i.e., the crystalline particles are not distributed randomly). The term "peak positions" as used herein refers to X-ray reflection positions as measured and observed in powder X-ray diffraction experiments. Peak positions are directly related to the dimensions of the unit cell. The peaks, identified by their respective peak positions, have been extracted from the diffraction patterns for the various polymorphic forms of salts of Compound 1.

The term "2 theta value" or "2θ" refers to the peak position in degrees based on the experimental setup of the X-ray diffraction experiment and is a common abscissa unit in diffraction patterns. In general, the experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions as described herein.

The term "amorphous" refers to any solid substance which (i) lacks order in three dimensions, or (ii) exhibits order in less than three dimensions, order only over short distances (e.g., less than 10 Å), or both. Thus, amorphous substances include partially crystalline materials and crystalline mesophases with, e.g. one- or two-dimensional translational order (liquid crystals), orientational disorder (orientationally disordered crystals), or conformational disorder (conformationally disordered crystals). Amorphous solids may be characterized by known techniques, including powder X-ray powder diffraction (PXRD) crystallography, solid state nuclear magnet resonance (ssNMR) spectroscopy, differential scanning calorimetry (DSC), or some combination of these techniques. Amorphous solids give diffuse PXRD patterns, typically comprised of one or two broad peaks (i.e., peaks having base widths of about 5° 2θ or greater).

The term "crystalline" refers to any solid substance exhibiting three-dimensional order, which in contrast to an amorphous solid substance, gives a distinctive PXRD pattern with sharply defined peaks.

The term "ambient temperature" refers to a temperature condition typically encountered in a laboratory setting. This includes the approximate temperature range of about 20 to about 30° C.

The term "detectable amount" refers to an amount or amount per unit volume that can be detected using conventional techniques, such as X-ray powder diffraction, differential scanning calorimetry, HPLC, Fourier Transform Infrared Spectroscopy (FT-IR), Raman spectroscopy, and the like.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "relative humidity" refers to the ratio of the amount of water vapor in air at a given temperature to the maximum amount of water vapor that can be held at that temperature and pressure, expressed as a percentage.

The term "relative intensity" refers to an intensity value derived from a sample X-ray diffraction pattern. The complete ordinate range scale for a diffraction pattern is assigned a value of 100. A peak having intensity falling between about 50% to about 100% on this scale intensity is termed very strong (vs); a peak having intensity falling between about 50% to about 25% is termed strong (s). Additional weaker peaks are present in typical diffraction patterns and are also characteristic of a given polymorph.

The term "slurry" refers to a solid substance suspended in a liquid medium, typically water or an organic solvent.

The term "under vacuum" refers to typical pressures obtainable by a laboratory oil or oil-free diaphragm vacuum pump.

The term "pharmaceutical composition" refers to a composition comprising one or more of the polymorphic forms of salts of Compound 1 described herein, and other chemical components, such as physiologically/pharmaceutically acceptable carriers, diluents, vehicles and/or excipients. The purpose of a pharmaceutical composition is to facilitate administration of a compound to an organism, such as a human or other mammal.

The term "pharmaceutically acceptable" "carrier", "diluent", "vehicle", or "excipient" refers to a material (or materials) that may be included with a particular pharmaceutical agent to form a pharmaceutical composition, and may be solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

The term "mediated by poly(ADP-ribose) polymerase (PARP) activity" refers to biological or molecular processes that are regulated, modulated, or inhibited by PARP activity. For certain applications, inhibition of PARP activity associated with cancer is preferred. Embodiments disclosed herein include methods of modulating or inhibiting PARP activity, for example in mammals, by administering polymorphic salt forms of Compound 1, or a solid form that comprises two or more polymorphic salt forms of Compound 1. The activity or efficacy of polymorphic salt forms of Compound 1, or a solid form that comprises two or more such forms, may be measured as described, for example, in U.S. Pat. No. 6,495,541 and U.S. Patent Application Publication No. 2006-0074073, the disclosures of which are incorporated herein by reference in their entireties.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of "treating" as defined immediately above. For example, the terms "treat", "treating" and "treatment" can refer to a method of alleviating or abrogating a hyperproliferative disorder (e.g., cancer) and/or one or more of its attendant symptoms. With regard particularly to cancer, these terms can indicate that the life expectancy of an individual affected with a cancer will be increased or that one or more of the symptoms of the disease will be reduced.

An "effective amount" refers to the amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The term "therapeutically effective amount" refers to that amount of the compound or polymorph being administered which can relieve to some extent one or more of the symptoms of the disorder being treated. In reference to the treatment of cancer, a therapeutically effective amount refers to that amount which, for example, has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

DETAILED DESCRIPTION OF THE INVENTION

Figure 1:
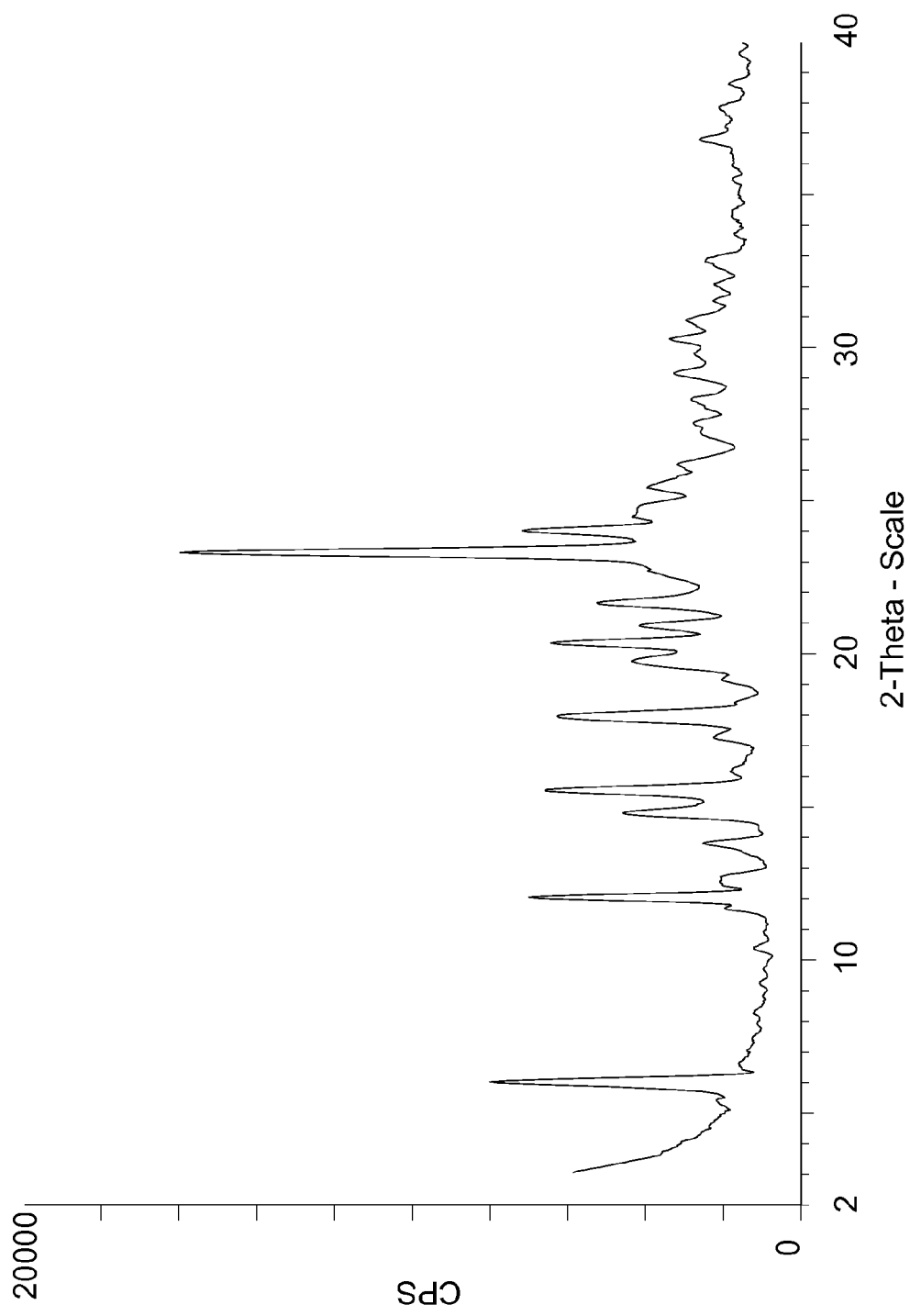
FIG. 1 shows a powder X-ray diffraction (PXRD) pattern of a maleate salt of Compound 1, polymorph Form A, using CuKα radiation at 1.5406 Å.

Several unique physical forms of Compound 1 have now been made. Compound 1, and methods of making it, are described in U.S. Pat. Nos. 6,495,541; 6,977,298; 7,429,578 and 7,323,562, which are herein incorporated by reference in their entireties. Certain salts and polymorphs thereof, of Compound 1, are disclosed in U.S. Pat. No. 7,268,126 and in International Patent Publication No. WO 04/087713, which are herein incorporated by reference in their entireties.

It has been found, as described herein, that Compound 1 can exist in multiple crystalline salt forms, such as maleate salt forms and camsylate salt forms. These forms may be used in a formulated product for the treatment of a mammalian disease condition mediated by poly(ADP-ribose) polymerase (PARP) activity, including cancer. Each form may have advantages over the others in terms of properties such as bioavailability, stability, and manufacturability. Novel crystalline salt forms of Compound 1 have been discovered which are likely to be more suitable for bulk preparation and handling than other forms. For example, the phosphate salt of Compound 1, while particularly suitable, for example, for intravenous dosage forms, may be less suitable for a solid dosage form due to its susceptibility to hydration. Maleate and camsylate salt forms described herein (e.g., maleate polymorph Form B and S-camsylate polymorph Form A) exist as physically stable forms and are not susceptible to hydration as compared to other salt forms of Compound 1, making them particularly suitable in the preparation of solid dosage forms. In addition, maleate and camsylate salts described herein can be isolated in fewer steps than other salt forms in the synthetic process, allowing greater scope to control the crystallization. A controlled crystallization can be used, for example, to provide API particles with properties that are advantageous to a solid dosage form, such as controlled particle size, crystallinity and crystal shape. Also described herein are processes for the preparation of each polymorphic salt form of Compound 1, substantially free from other polymorphic forms of Compound 1. Additionally, described herein are pharmaceutical formulations comprising crystalline salts of Compound 1 in different polymorphic forms, and methods of treating hyperproliferative conditions by administering such pharmaceutical formulations. Additionally, described herein are pharmaceutical formulations comprising crystalline salts of Compound 1 in different polymorphic forms, and methods of treating a mammalian disease condition (e.g., cancer) mediated by poly(ADP-ribose) polymerase (PARP) activity by administering such pharmaceutical formulations.

I. Crystalline Salt Forms of Compound 1

Several crystalline forms of Compound 1 are described herein. Each crystalline salt form of Compound 1 can be characterized by one or more of the following: powder X-ray diffraction pattern (e.g., X-ray diffraction peaks at various diffraction angles (2θ)); solid state nuclear magnetic resonance (NMR) spectral pattern; melting point onset (and onset of dehydration for hydrated forms) as illustrated by endotherms of a Differential Scanning calorimetry (DSC) thermogram; hygroscopic properties as illustrated by Dynamic Vapor Sorption measurements; FT-IR spectral diagram pattern; Raman spectral diagram pattern; aqueous solubility; light stability under International Conference on Harmonization (ICH) high intensity light conditions, and physical and chemical storage stability according to methods known in the art or described herein. For example, maleate polymorph Form A, maleate polymorph Form B, S-camsylate polymorph Form A, and S-camsylate polymorph Form B and of Compound 1 were each characterized by the positions and relative intensities of peaks in their powder X-ray diffraction patterns. The powder X-ray diffraction parameters differ for each of the polymorphic forms of Compound 1. For example, maleate polymorph Form A, maleate polymorph Form B, S-camsylate polymorph Form A, and S-camsylate polymorph Form B of Compound 1 can therefore be distinguished from each other and from other polymorphic forms of Compound 1 by using powder X-ray diffraction.

Powder X-ray diffraction patterns of the different polymorphic forms (e.g., maleate polymorph Form A, maleate polymorph Form B, S-camsylate polymorph Form A, and S-camsylate polymorph Form B) of Compound 1 were determined according to procedures described in Examples 6-8 using CuKα radiation at 1.5406 Å. The peaks for the PXRD patterns obtained for Maleate polymorph Form A, Maleate polymorph Form B, S-camsylate polymorph Form A, and S-camsylate polymorph Form B were selected using Bruker-AXS Ltd. Evaluation software with a threshold of 1 and a peak width of 0.3° 2-theta. With the exception of S-camsylate polymorph Form B, the data were collected at 21° C.

To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses can result from a variety of factors including: (a) errors in sample preparation (e.g., sample height); (b) instrument errors (e.g., flat sample errors); (c) calibration errors; (d) operator errors (including those errors present when determining the peak locations); and (e) the nature of the material (e.g., preferred orientation and transparency errors). Calibration errors and sample height errors often result in a shift of all the peaks in the same direction. Small differences in sample height when using a flat holder will lead to large displacements in PXRD peak positions. A systematic study showed that, using a Shimadzu XRD-6000 in the typical Bragg-Brentano configuration, sample height difference of 1 mm led to peak shifts as high as 1 degree (2θ) (Chen et al., *J Pharmaceutical and Biomedical Analysis* 26:63 (2001)). These shifts can be identified from the X-ray diffractogram and can be eliminated by compensating for the shift (applying a systematic correction factor to all peak position values) or recalibrating the instrument. It is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 degrees (2θ).

One of skill in the art will appreciate that the peak positions (2θ) will show some variability, typically as much as 0.1 to 0.2 degrees (2θ), depending, for example, on the solvents being used and/or on the apparatus being used to measure the diffraction. Accordingly, where peak positions (2θ) are reported, one of skill in the art will recognize that such numbers are intended to encompass such variability. Furthermore, where the polymorphs of the present invention are described as having a powder X-ray diffraction pattern essentially the same as that shown in a given figure, the term "essentially the same" is also intended to encompass such variability in diffraction peak positions. Further, one skilled in the art will appreciate that relative peak intensities will show inter-apparatus variability as well as variability due to the degree of crystallinity, preferred orientation, prepared sample surface, the degree of purity of the sample being analyzed, and other factors known to those skilled in the art, and should be taken as qualitative measures only. The skilled person will also appreciate that measurements using a different wavelength will result in different shifts according to the Bragg equation $-n\lambda=2d \sin \theta$. Such further PXRD patterns generated by use of alternative wavelengths are considered to be alternative representations of the PXRD patterns of the crystalline materials of embodiments described herein and as such are within the scope of the present embodiments.

The different polymorphs described herein can also be characterized using solid state NMR spectroscopy according to methods known in the art or described herein. For example, $^{13}C$ solid state spectra and $^{19}F$ solid state spectra can be collected according to the procedures described in Examples 9-10. It should be noted that $^{13}C$ or $^{19}F$ chemical shifts measured in solid state NMR will typically have a variability of up to 0.2 ppm for well defined peaks, and even larger for broad lines.

Different crystalline salt forms of Compound 1 were also distinguished using differential scanning calorimetry (DSC) according to the procedures described in the Examples. DSC measures the difference in heat energy uptake between a sample and an appropriate reference with increase in temperature. For example, for the measurement of a solid powder sample, the reference can be an empty sample pan of the type used in preparation of the sample. DSC thermograms can be characterized by endotherms (indicating energy uptake) and also by exotherms (indicating energy release), typically as the sample is heated. Depending on several factors, the endotherms exhibited may vary by about 0.01-5° C. for crystal polymorphs melting above or below the endotherms, such as those depicted in the appended figures. Factors responsible for such variance include, for example, the rate of heating (e.g., the scan rate) at which the DSC analysis is conducted, the way the DSC onset temperature is defined and determined, the calibration standard used, instrument calibration, the relative humidity and the chemical purity of the sample. For any given sample, the observed endotherms may also differ from instrument to instrument; however, it will generally be within the ranges described herein provided the instruments are calibrated similarly.

Different polymorphic forms of a compound may have different hygroscopic properties. For example, salts of Compound 1 were characterized based on their hygroscopic properties using dynamic vapor sorption measurements according to procedures described in Example 12.

In some embodiments, the solid forms may also comprise more than one polymorphic form. One of skill in the art will also recognize that crystalline forms of a given compound can exist in substantially pure forms of a single polymorph, but can also exist in a crystalline form that comprises a mixture of two or more different polymorphs or amorphous forms. Where a solid form comprises two or more polymorphs, the X-ray diffraction pattern will typically have peaks characteristic of each of the individual polymorphs. For example, a solid form that comprises two polymorphs will typically have a powder X-ray diffraction pattern that is a convolution of the two X-ray diffraction patterns that correspond to the substantially pure polymorphic forms. For example, a solid form of Compound 1 or a salt thereof can contain a first and second polymorphic form where the solid form contains at least 10% by weight of the first polymorph. In a further example, the solid form can contain at least 20% by weight of the first polymorph. Even further examples contain at least 30%, at least 40%, or at least 50% by weight of the first polymorph. One of skill in the art will recognize that many such combinations of several individual polymorphs and amorphous forms in varying amounts are possible.

Two polymorphic forms of the maleate salt of Compound 1 have been identified and characterized as indicated in FIGS. 1 to 8, and are designated as maleate polymorph Form A and maleate polymorph Form B. In addition, polymorphic forms of the camsylate salt of Compound 1 and various salts containing different R:S ratios of camphor sulfonic acid have been identified and characterized as indicated in FIGS. 9 to 33, and are designated as S-camsylate polymorph Form A, S-camsylate polymorph Form B, S-camsylate polymorph Form C, R-camsylate polymorph Form A, or the salt with the designated R:S ratio of camphor sulfonic acid. Furthermore, an amorphous form of the S-camsylate salt of Compound 1 has been identified and characterized as indicated in FIGS. 34-38. As used herein, the term "camsylate salt" refers to the S-camsylate salt, the R-camsylate salt, or salts with camphor sulfonic acid in particular R:S ratios. The polymorphs, pharmaceutical compositions including one or more polymorphs, and methods of using the polymorphs and pharmaceutical compositions thereof are described in more detail in the following sections and examples.

A. Maleate Salt of Compound 1, Polymorph Form A

The maleate salt of Compound 1, maleate polymorph Form A, can be produced as described in Example 1.

Maleate polymorph Form A was characterized by the PXRD pattern shown in FIG. 1 and described in Example 7. The PXRD pattern of maleate polymorph Form A, expressed in terms of the degree (2θ) and relative intensities with a relative intensity of ≥15.0%, measured on a Bruker D5000 diffractometer with CuKα radiation at 1.5406 A, is also shown in Table 1.

TABLE 1

| Angle (Degree 2θ ± 0.2°) | Relative Intensity (≥15.0%) |
|---|---|
| 6.0 | 50.9 |
| 12.0 | 44.7 |
| 13.8 | 15.8 |
| 14.8 | 29.4 |

TABLE 1-continued

| Angle (Degree 2θ ± 0.2°) | Relative Intensity (≥15.0%) |
|---|---|
| 15.5 | 40.3 |
| 17.9 | 35.6 |
| 19.8 | 25.5 |
| 20.3 | 39.5 |
| 20.9 | 26.7 |
| 21.7 | 32.4 |
| 23.3 | 100.0 |
| 24.0 | 42.5 |
| 24.5 | 25.2 |
| 24.8 | 25.2 |
| 25.4 | 24.5 |
| 26.2 | 19.5 |
| 27.5 | 16.7 |
| 28.3 | 19.0 |
| 29.2 | 20.5 |
| 30.3 | 20.5 |
| 31.0 | 17.4 |
| 36.8 | 15.5 |

Figure 2:
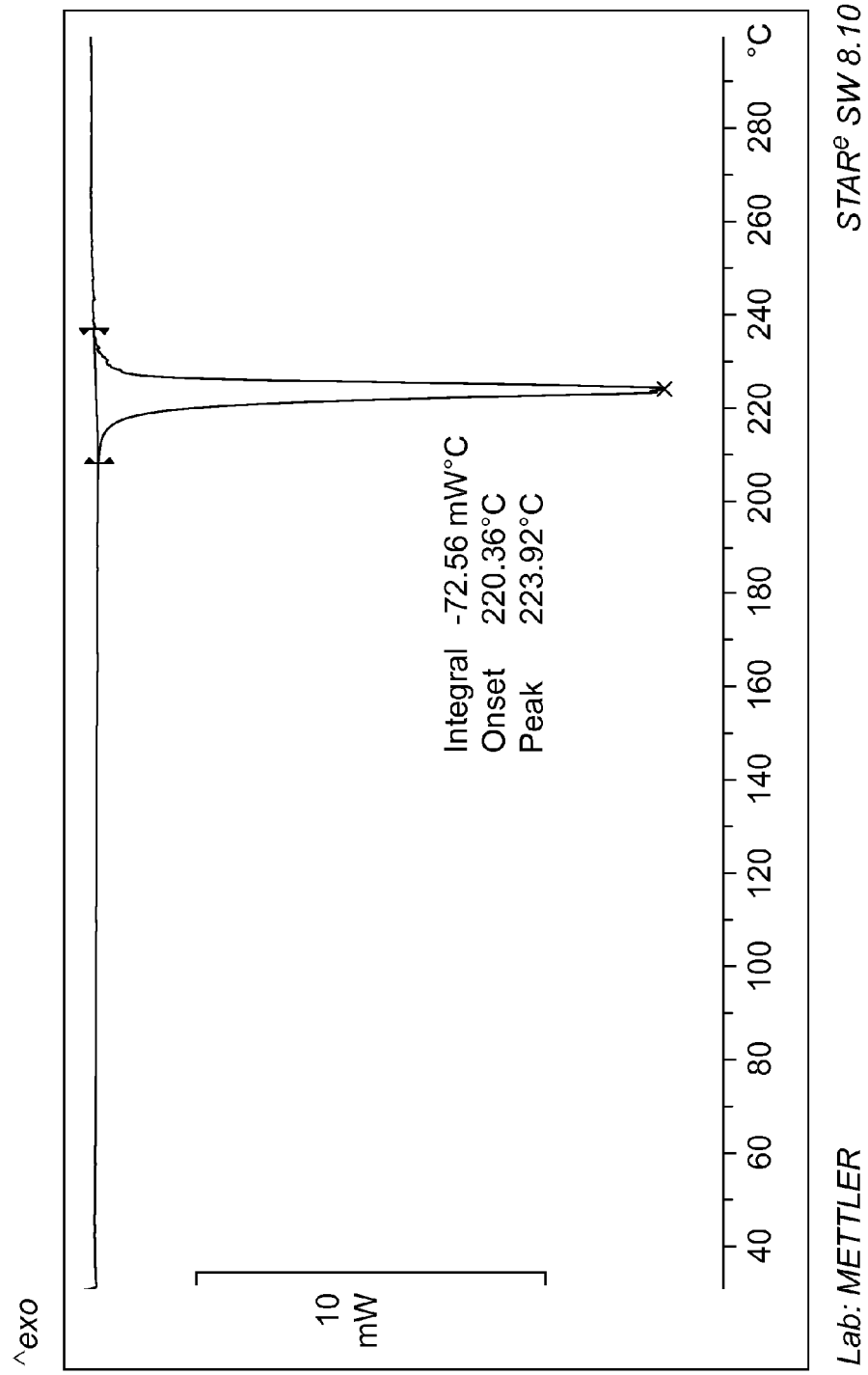
FIG. 2 shows a differential scanning calorimetry (DSC) thermogram of a maleate salt of Compound 1, polymorph Form A.

The DSC thermogram for maleate polymorph Form A, shown in FIG. 2 and described in Example 11, indicates an endotherm onset at 220.36° C.

B. Maleate Salt of Compound 1, Maleate Polymorph Form B

The maleate salt of Compound 1, maleate polymorph Form B, can be produced as described in Example 2, using ethanol in the synthetic scheme. The maleate salt of Compound 1, maleate polymorph Form B, can also be produced as described in Example 3, using isopropyl alcohol in the synthetic scheme.

Figure 3:
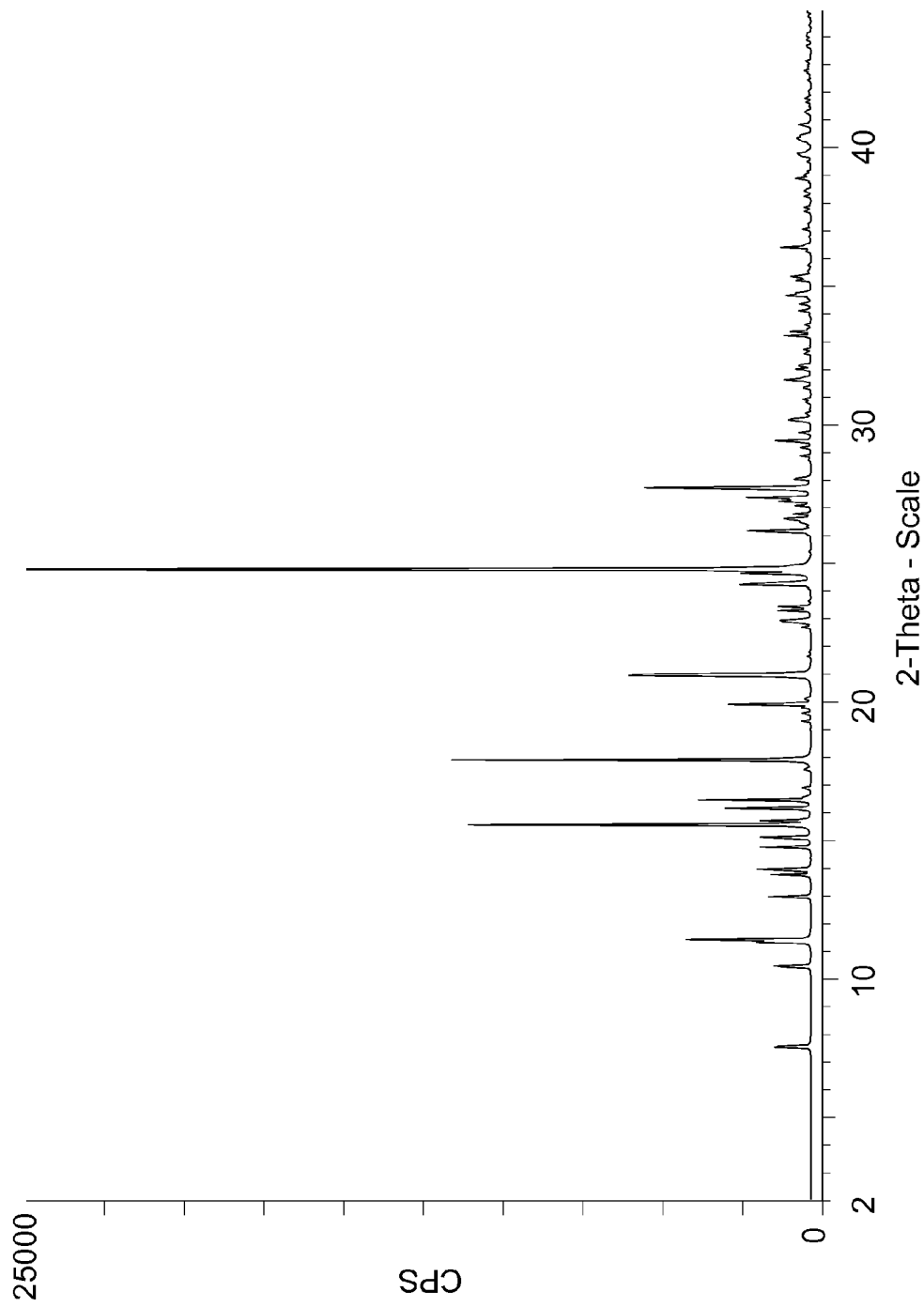
FIG. 3 shows a simulated PXRD pattern of a maleate salt of Compound 1, polymorph Form B, using CuKα radiation at 1.5406 Å.

Maleate polymorph Form B was characterized by the simulated PXRD pattern calculated from a single crystal structure, as shown in FIG. 3. The simulated PXRD pattern of maleate polymorph Form B, expressed in terms of the degree (2θ) and relative intensities with a relative intensity of ≥5.0%, calculated from the single crystal structure of maleate Form B using the "Reflex Powder Diffraction" module of Accelrys M S Modelling™ [version 4.4], is also shown in Table 2. Pertinent simulation parameters included a wavelength of 1.5406 Å (Cu Kα) and a polarization factor of 0.5.

TABLE 2

| Angle (Degree 2θ) | Relative Intensity (≥5.0%) |
|---|---|
| 11.3 | 5.5 |
| 11.4 | 12.2 |
| 14.0 | 5.4 |
| 14.7 | 5.1 |
| 15.1 | 5.1 |
| 15.5 | 32.9 |
| 15.7 | 5.1 |
| 16.1 | 8.5 |
| 16.5 | 11.1 |
| 17.9 | 34.5 |
| 19.9 | 8.2 |
| 21.0 | 17.7 |
| 24.2 | 7.1 |
| 24.6 | 7.0 |
| 24.8 | 100.0 |
| 26.2 | 6.4 |
| 27.4 | 6.4 |
| 27.7 | 16.2 |

Figure 4:
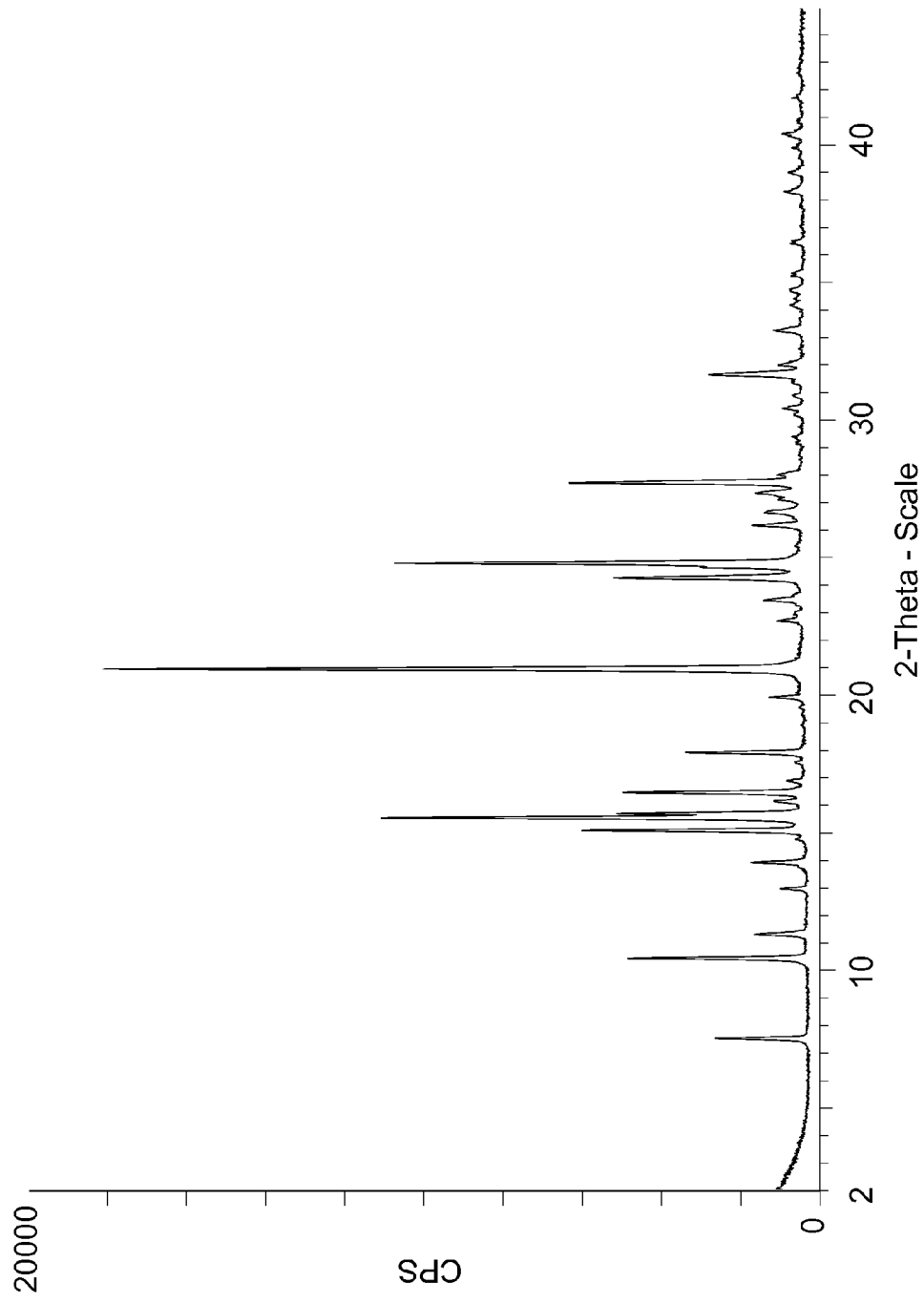
FIG. 4 shows an experimental PXRD pattern of a maleate salt of Compound 1, polymorph Form B, using CuKα radiation at 1.5406 Å.

Maleate polymorph Form B was also characterized by measuring the PXRD pattern for a particular batch of maleate polymorph Form B. This experimental PXRD pattern is shown in FIG. 4 and described in Example 6. The experimental PXRD pattern of maleate polymorph Form B, expressed in terms of the degree (2θ) and relative intensities with a relative intensity of ≥5.0%, measured on a Bruker-AXS Ltd., D4 diffractometer with CuKα radiation at 1.5406 Å, is also shown in Table 3.

TABLE 3

| Angle (Degree 2θ ± 0.2°) | Relative Intensity (≥5.0%) |
|---|---|
| 7.5 | 14.4 |
| 10.4 | 26.6 |
| 11.3 | 9.0 |
| 12.9 | 5.4 |
| 13.9 | 9.4 |
| 15.1 | 33.1 |
| 15.5 | 61.1 |
| 15.7 | 28.2 |
| 16.1 | 6.2 |
| 16.4 | 27.3 |
| 17.9 | 18.6 |
| 19.9 | 6.8 |
| 20.9 | 100.0 |
| 22.7 | 5.8 |
| 23.5 | 7.6 |
| 24.3 | 28.6 |
| 24.6 | 16.5 |
| 24.8 | 59.2 |
| 26.2 | 9.3 |
| 26.6 | 7.5 |
| 27.1 | 5.7 |
| 27.3 | 8.8 |
| 27.7 | 34.9 |
| 28.0 | 5.7 |
| 30.4 | 5.0 |
| 31.7 | 15.3 |
| 32.0 | 5.6 |
| 33.3 | 6.3 |
| 40.4 | 5.1 |

It can be seen that the peak positions for the simulated and experimental PXRD patterns agree very well. Any difference in peak position, relative intensity and width of the diffraction peaks can be attributed, for example, to inter-apparatus variability as well as variability due to the degree of crystallinity, preferred orientation, prepared sample surface, the degree of purity of the sample being analyzed, and other factors known to those skilled in the art.

Figure 5:
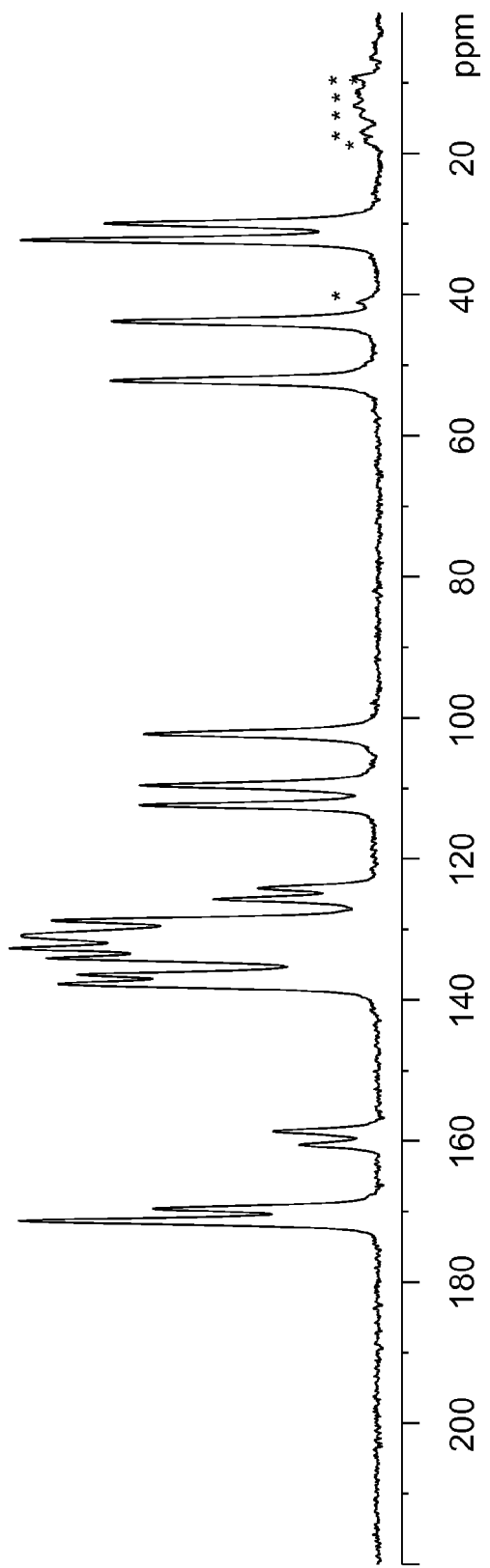
FIG. 5 shows a $^{13}$C solid state nuclear magnetic resonance (NMR) spectrum of a maleate salt of Compound 1, polymorph Form B.

Maleate polymorph Form B of Compound 1 was also characterized by the solid state NMR spectral pattern shown in FIG. 5, carried out on a Bruker-Biospin 4 mm BL CPMAS probe positioned into a wide-bore Bruker-Biospin DSX 500 MHz NMR spectrometer as described in Example 9. The $^{13}$C chemical shifts of maleate polymorph Form B of Compound 1 are shown in Table 4.

TABLE 4

| $^{13}$C Chemical Shifts[a] [±0.2 ppm] | Intensity[b] |
|---|---|
| 171.3 | 11.7 |
| 169.6 | 7.3 |
| 160.5 | 2.6 |
| 158.6 | 3.4 |
| 137.7 | 10.4 |
| 136.4 | 9.8 |
| 134.1 | 10.8 |
| 132.7 | 12.0 |
| 130.9 | 11.6 |
| 128.7 | 10.6 |
| 125.7 | 5.4 |
| 124.2 | 3.9 |
| 112.4 | 7.8 |
| 109.6 | 7.8 |
| 102.3 | 7.6 |

TABLE 4-continued

| $^{13}$C Chemical Shifts$^a$ [±0.2 ppm] | Intensity$^b$ |
|---|---|
| 52.2 | 8.7 |
| 43.8 | 8.7 |
| 32.3 | 11.7 |
| 29.9 | 8.9 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Figure 6:
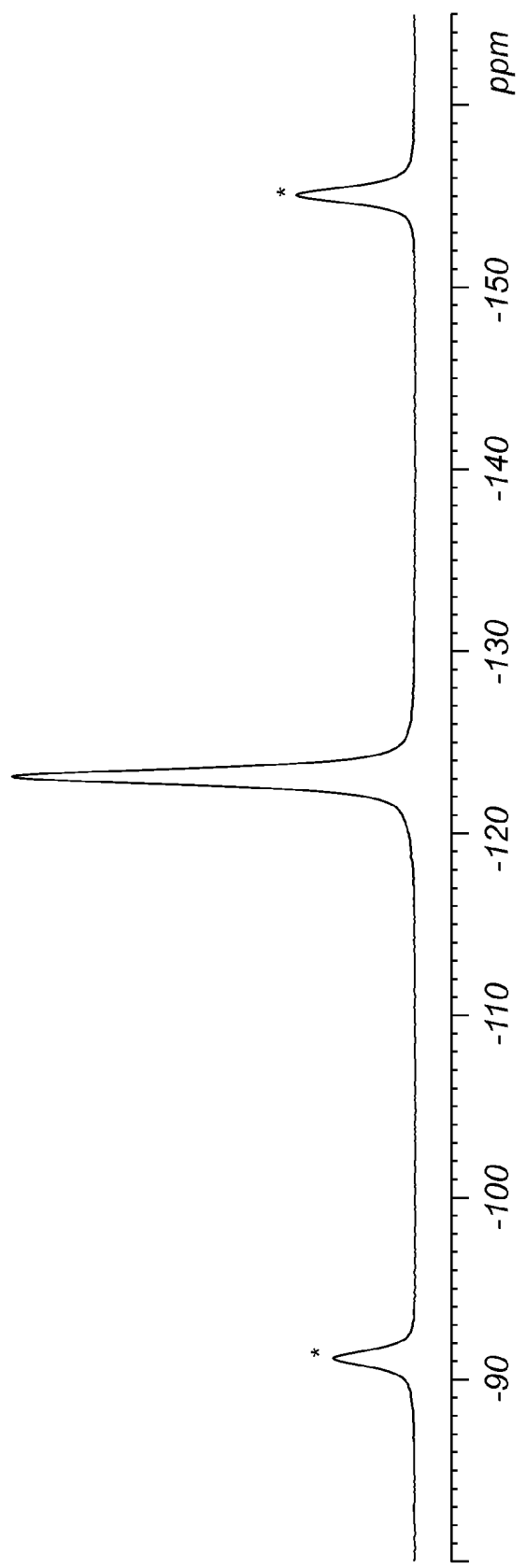
FIG. 6 shows a $^{19}$F solid state NMR spectrum of a maleate salt of Compound 1, polymorph Form B.

Maleate polymorph Form B of Compound 1 was also characterized by the solid state NMR spectral pattern shown in FIG. 6, carried out on a Bruker-Biospin 4 mm BL CPMAS probe positioned into a wide-bore Bruker-Biospin DSX 500 MHz NMR spectrometer as described in Example 9. The $^{19}$F chemical shifts of maleate polymorph Form B of Compound 1 are shown in Table 5.

TABLE 5

| $^{19}$F Chemical Shifts$^a$ [±0.2 ppm] | Intensity$^b$ |
|---|---|
| −123.1 | 12.0 |

$^a$Referenced to external standard of trifluoroacetic acid (50% V/V in H$_2$O) at −76.54 ppm.
$^b$Defined as peak heights.

Figure 7:
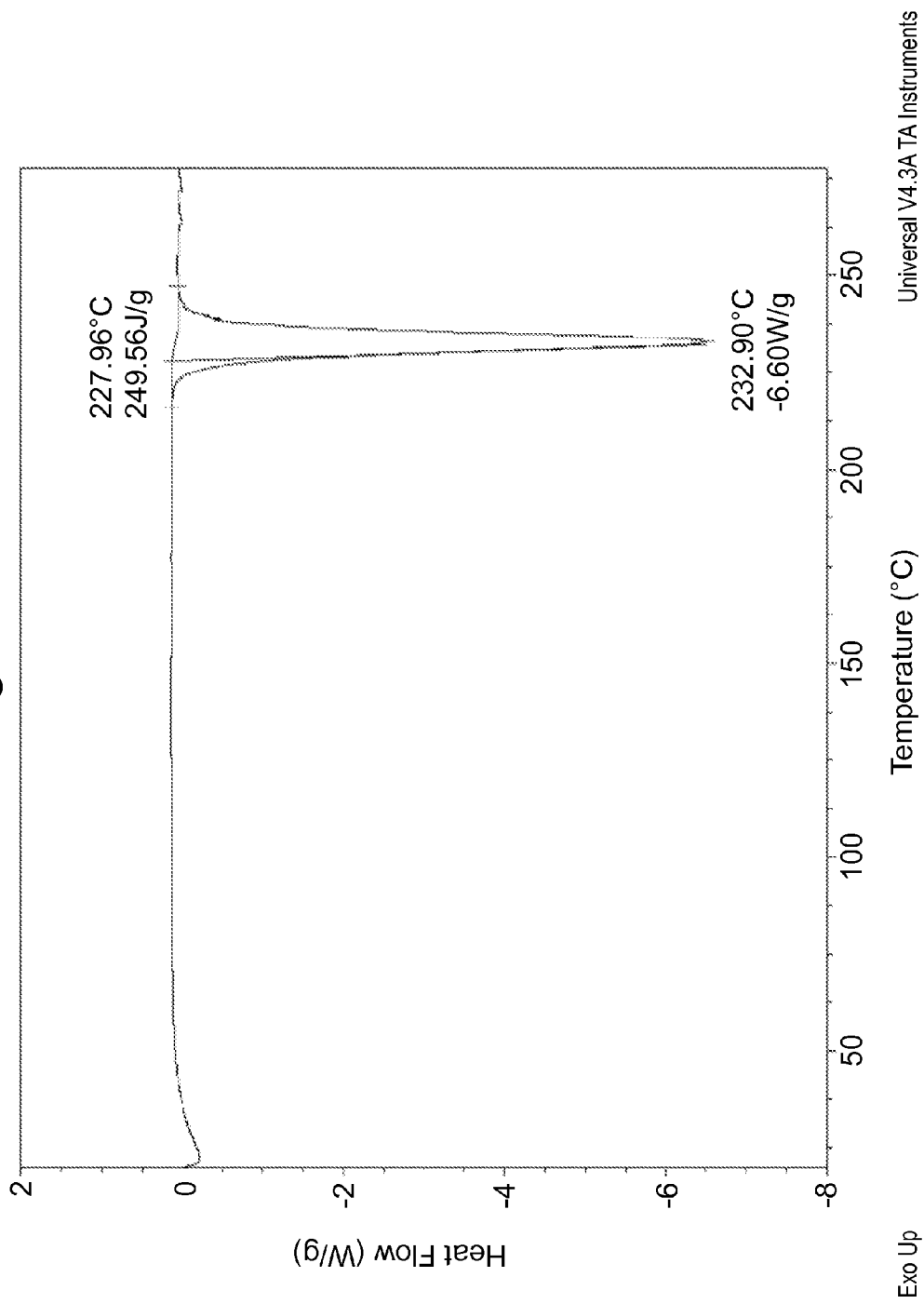
FIG. 7 shows a DSC thermogram of a maleate salt of Compound 1, polymorph Form B.
Figure 8:
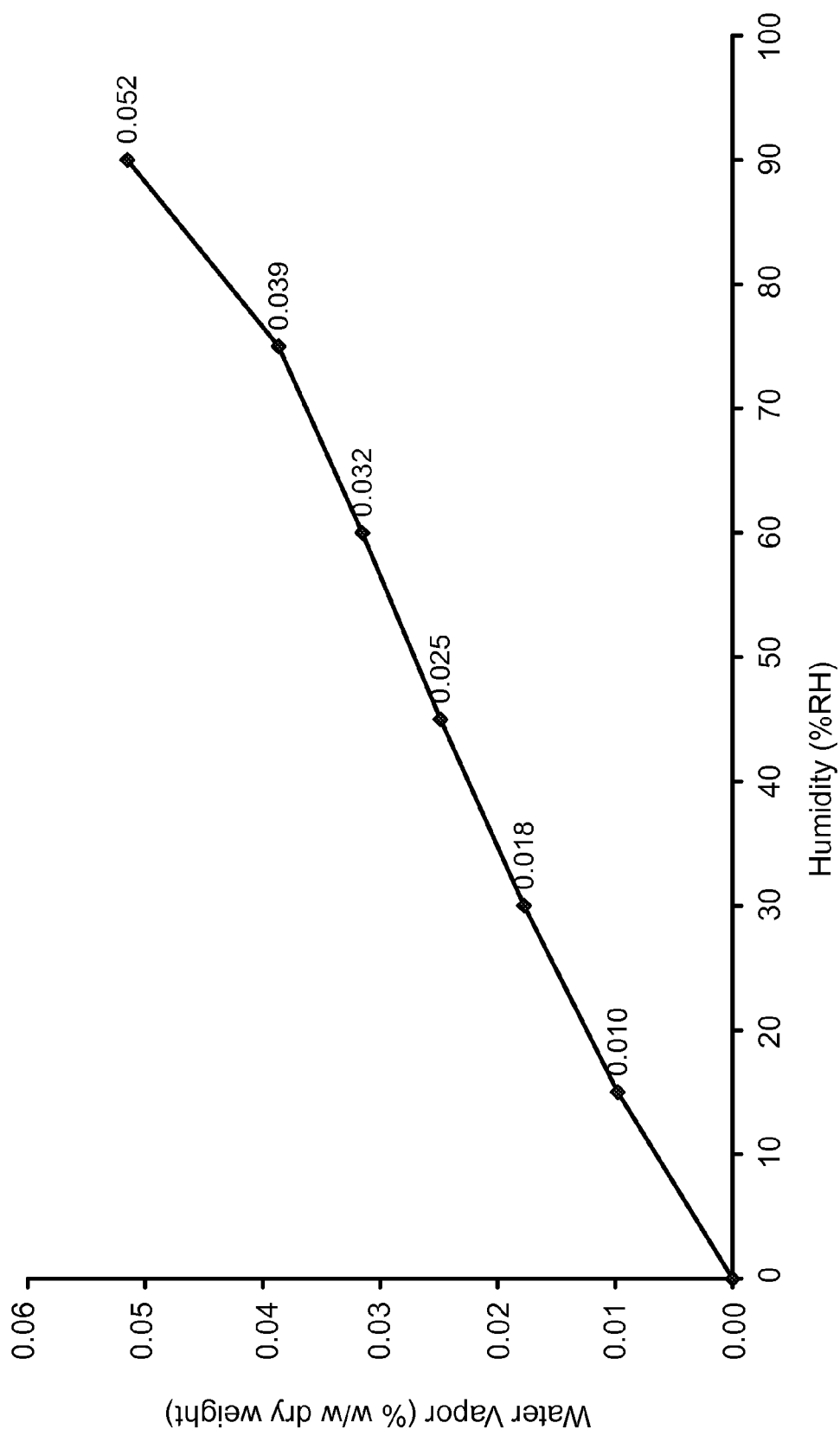
FIG. 8 shows a dynamic vapor sorption isotherm of a maleate salt of Compound 1, polymorph Form B.

The DSC thermogram for maleate polymorph Form B, shown in FIG. 7, indicates an endotherm onset at 228.0° C. The dynamic vapor sorption isotherm for maleate polymorph Form B is shown in FIG. 8. The dynamic vapor sorption isotherm indicates maleate polymorph Form B is non-hygroscopic.

Maleate polymorph Form B of Compound 1 was also characterized by Fourier Transform-Infrared Spectroscopy (FT-IR) as described in Example 25, and the spectral peaks are shown in Table 6. Absorption band frequencies are listed. (w: weak, m: medium, s: strong, vs: very strong). Experimental error is ±2 cm$^{-1}$ except for * error on peak position could be considerably larger.

TABLE 6

| Wavenumber (cm$^{-1}$) |
|---|
| 3179* w |
| 2970 w |
| 2927 w |
| 2884 w |
| 2830 w |
| 2484 w |
| 1685 w |
| 1594 m |
| 1576 m |
| 1509 w |
| 1457 s |
| 1444 s |
| 1417 m |
| 1389 w |
| 1368 m |
| 1353 s |
| 1347 s |
| 1332 s |
| 1315 m |
| 1275 w |
| 1267 w |
| 1252 w |
| 1212 w |
| 1179 w |
| 1159 w |
| 1127 s |

TABLE 6-continued

| Wavenumber (cm$^{-1}$) |
|---|
| 1106 m |
| 1066 m |
| 1051 m |
| 1030 m |
| 1020 m |
| 1013 m |
| 971 m |
| 954 m |
| 938 w |
| 916 w |
| 895 w |
| 886 m |
| 877 w |
| 866 s |
| 856 m |
| 841 s |
| 836 s |
| 788 s |
| 761 s |
| 741 m |
| 699 w |
| 679 s |
| 663 m |

Maleate polymorph Form B of Compound 1 was also characterized by Fourier Transform-Raman Spectroscopy (FT-Raman) as described in Example 26, and the spectral peaks are shown in Table 7. (w: weak, m: medium, s: strong, vs: very strong). Experimental error is ±2 cm$^{-1}$.

TABLE 7

| Wavenumber (cm$^{-1}$) |
|---|
| 3237 w |
| 3060 w |
| 3031 w |
| 2972 w |
| 2948 w |
| 2929 w |
| 2887 w |
| 2834 w |
| 2819 w |
| 2716 w |
| 2651 w |
| 2589 w |
| 2562 w |
| 2534 w |
| 1694 w |
| 1621 vs |
| 1585 s |
| 1563 s |
| 1511 m |
| 1460 s |
| 1431 w |
| 1407 w |
| 1387 w |
| 1370 m |
| 1350 s |
| 1330 m |
| 1268 w |
| 1218 w |
| 1195 w |
| 1181 w |
| 1130 w |
| 1069 s |
| 1033 w |
| 1003 w |
| 961 w |
| 940 w |
| 898 w |
| 883 w |
| 857 w |
| 846 w |
| 794 w |

TABLE 7-continued

| Wavenumber (cm$^{-1}$) |
| --- |
| 744 w |
| 732 w |
| 702 w |
| 665 w |
| 647 w |
| 619 w |
| 557 w |
| 524 w |
| 503 w |
| 487 w |
| 464 w |
| 433 w |
| 414 w |
| 402 w |
| 381 w |
| 345 w |
| 318 w |
| 299 w |
| 257 w |
| 216 w |
| 166 w |
| 149 w |
| 126 m |
| 106 m |
| 72 s |

C. S-camsylate Salt of Compound 1, S-camsylate Polymorph Form A

The S-camsylate salt of Compound 1, S-camsylate polymorph Form A, can be produced as described in Example 4, using tetrahydrofuran in the synthetic scheme. The S-camsylate salt of Compound 1, S-camsylate polymorph Form A, can also be produced as described in Example 5, using isopropyl alcohol in the synthetic scheme.

Figure 9:
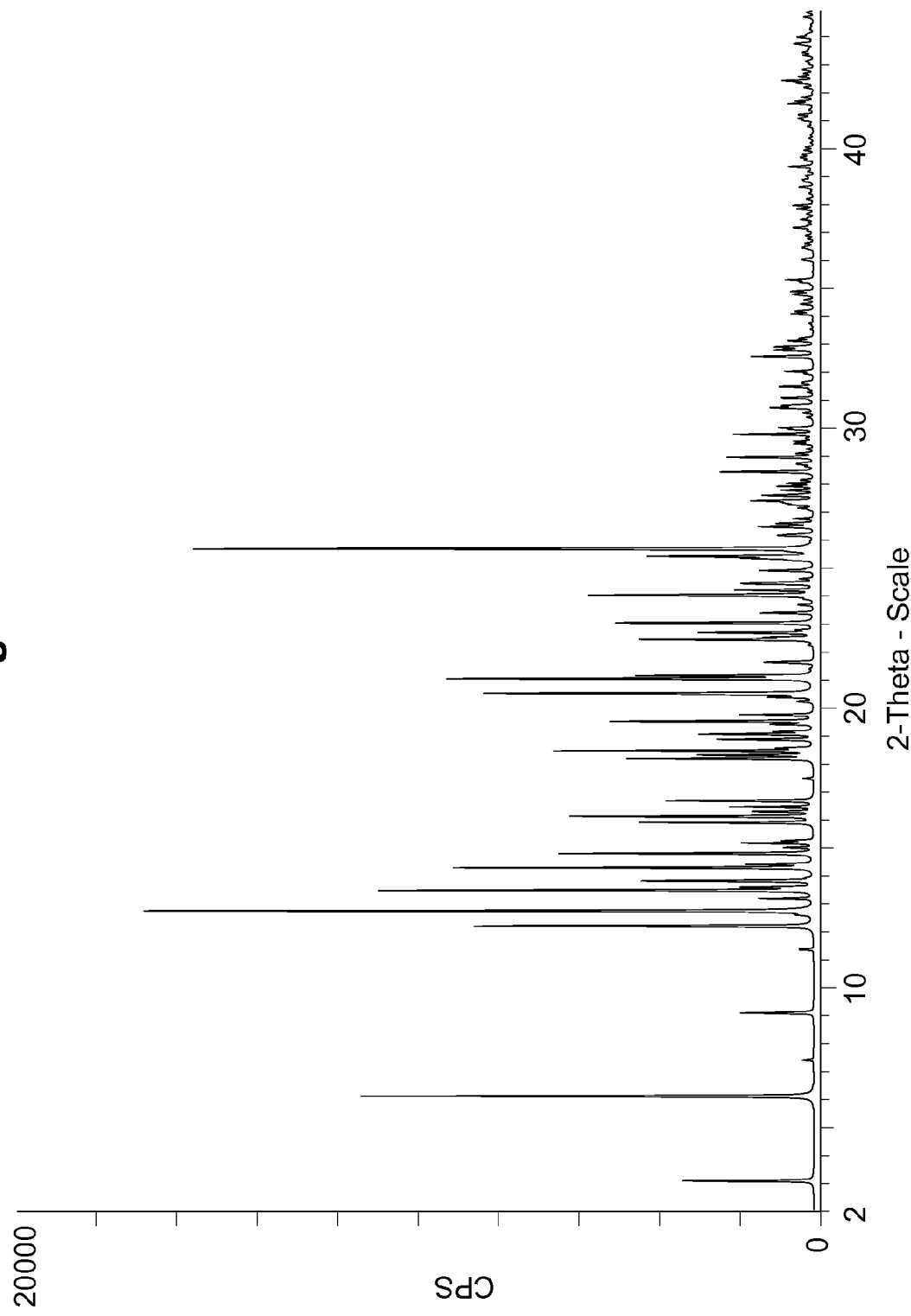
FIG. 9 shows a simulated PXRD pattern of an S-camsylate salt of Compound 1, polymorph Form A, using CuKα radiation at 1.5406 Å.

S-camsylate polymorph Form A was characterized by the simulated PXRD pattern calculated from a single crystal structure, as shown in FIG. 9. The simulated PXRD pattern of S-camsylate polymorph Form A, expressed in terms of the degree (2θ) and relative intensities with a relative intensity of ≥15.0%, calculated from the single crystal structure of camsylate Form A using the "Reflex Powder Diffraction" module of Accelrys M S Modelling™ [version 4.4], is also shown in Table 8. Pertinent simulation parameters included a wavelength of 1.5406 Å (Cu Kα) and a polarization factor of 0.5.

TABLE 8

| Angle (Degree 2θ) | Relative Intensity (≥15.0%) |
| --- | --- |
| 3.0 | 21.1 |
| 6.1 | 68.2 |
| 12.2 | 51.7 |
| 12.7 | 100.0 |
| 13.4 | 65.7 |
| 13.8 | 27.3 |
| 14.3 | 54.7 |
| 14.8 | 39.2 |
| 15.9 | 27.5 |
| 16.1 | 37.7 |
| 16.7 | 23.6 |
| 18.2 | 29.3 |
| 18.3 | 19.0 |
| 18.4 | 40.1 |
| 18.9 | 16.2 |
| 19.0 | 18.8 |
| 19.5 | 31.8 |
| 20.5 | 50.3 |
| 21.0 | 55.7 |
| 21.1 | 28.0 |
| 22.4 | 27.6 |
| 22.7 | 18.9 |
| 23.0 | 31.0 |
| 24.0 | 35.0 |
| 25.4 | 26.3 |
| 25.7 | 92.8 |
| 28.4 | 15.8 |

Figure 10:
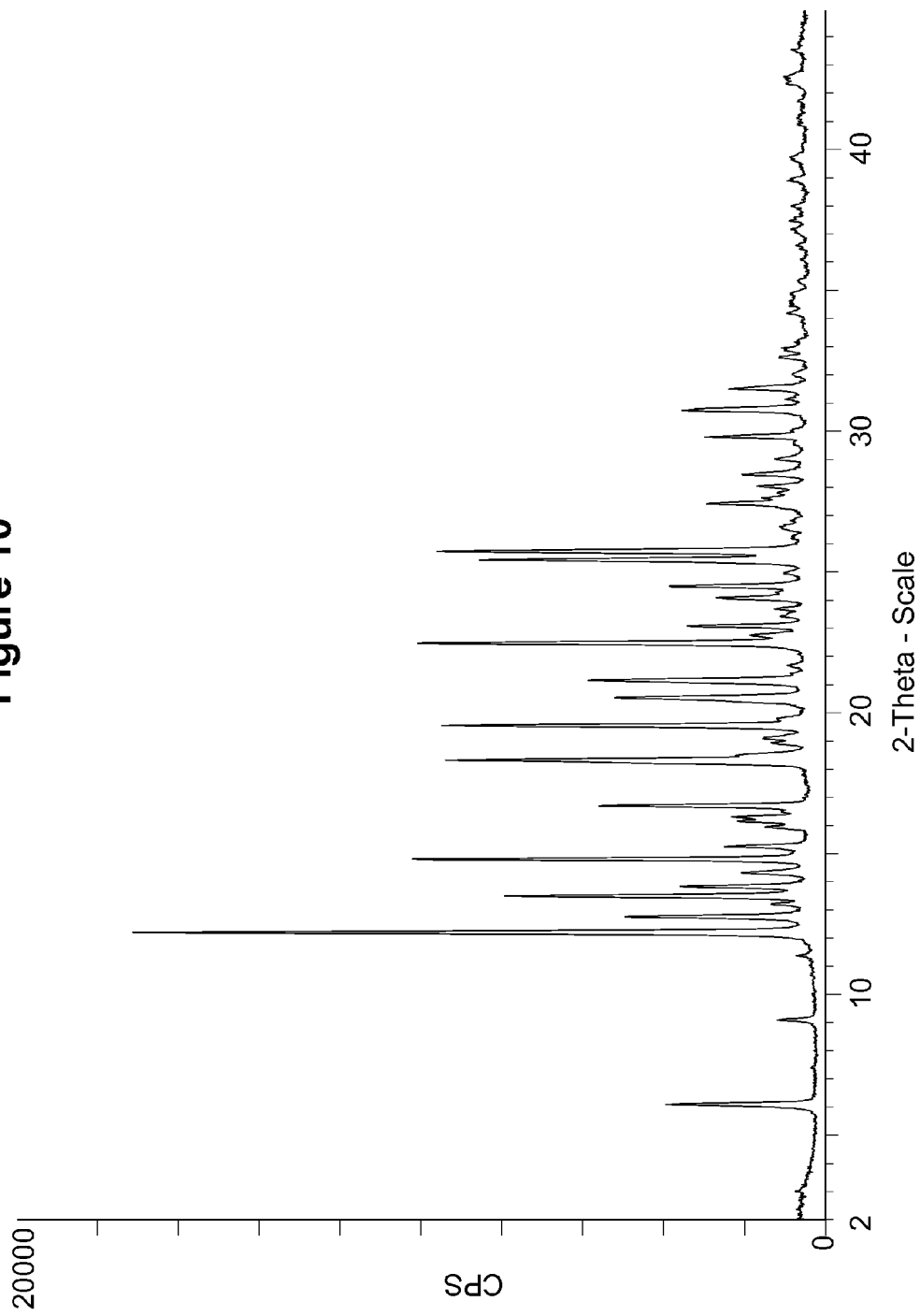
FIG. 10 shows an experimental PXRD pattern of an S-camsylate salt of Compound 1, polymorph Form A, using CuKα radiation at 1.5406 Å.

S-camsylate polymorph Form A was also characterized by measuring the PXRD pattern for a particular batch of S-camsylate polymorph Form A. This experimental PXRD pattern is shown in FIG. 10. The experimental PXRD pattern of S-camsylate polymorph Form A, expressed in terms of the degree (2θ) and relative intensities with a relative intensity of ≥10.0%, measured on a Bruker-AXS Ltd., D4 diffractometer with CuKα radiation at 1.5406 Å, is also shown in Table 9.

TABLE 9

| Angle (Degree 2θ ± 0.2°) | Relative Intensity (≥10.0%) |
| --- | --- |
| 6.0 | 22.9 |
| 12.2 | 100.0 |
| 12.7 | 28.8 |
| 13.5 | 46.2 |
| 13.8 | 20.8 |
| 14.3 | 11.9 |
| 14.8 | 59.5 |
| 15.2 | 14.4 |
| 16.1 | 12.5 |
| 16.3 | 13.5 |
| 16.7 | 32.3 |
| 18.3 | 54.8 |
| 18.5 | 12.9 |
| 19.5 | 55.4 |
| 20.5 | 30.3 |
| 21.1 | 34.1 |
| 22.5 | 58.8 |
| 22.7 | 10.7 |
| 23.1 | 19.8 |
| 24.1 | 15.6 |
| 24.5 | 22.3 |
| 25.4 | 49.9 |
| 25.7 | 56.0 |
| 27.4 | 17.0 |
| 28.5 | 11.8 |
| 29.8 | 17.2 |
| 30.7 | 20.6 |
| 30.8 | 18.8 |
| 31.5 | 13.7 |

It can be seen that the peak positions for the simulated and experimental PXRD patterns agree very well. Any difference in peak position, relative intensity and width of the diffraction peaks can be attributed, for example, to inter-apparatus variability as well as variability due to the degree of crystallinity, preferred orientation, prepared sample surface, the degree of purity of the sample being analyzed, and other factors known to those skilled in the art.

Figure 11:
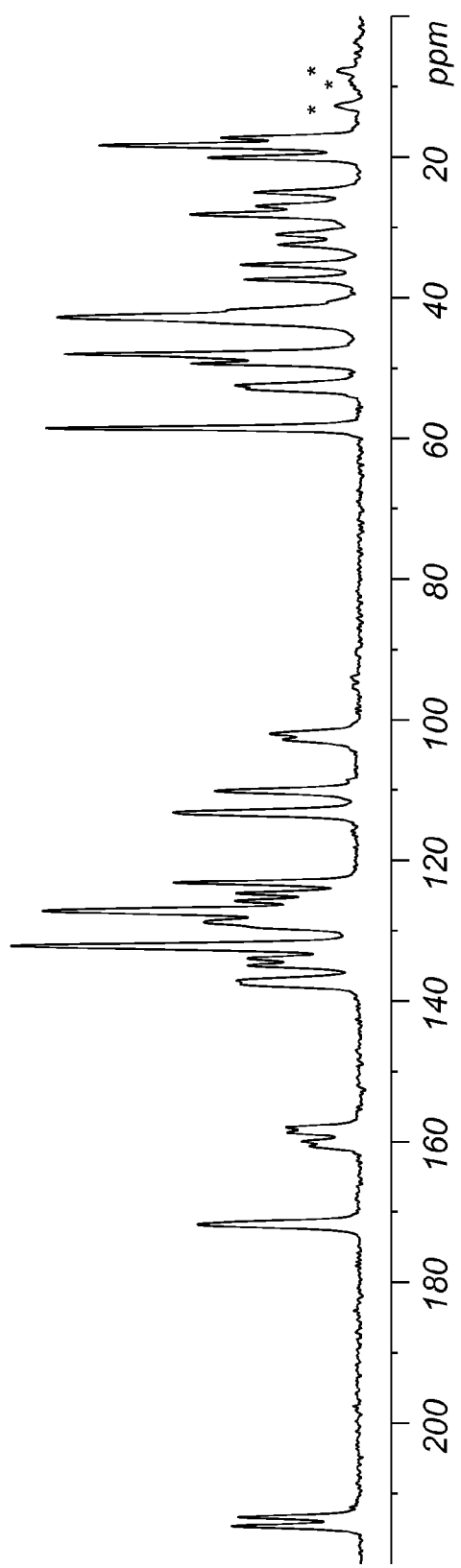
FIG. 11 shows a $^{13}$C solid state NMR spectrum of an S-camsylate salt of Compound 1, polymorph Form A.

S-camsylate polymorph Form A of Compound 1 was also characterized by the solid state NMR spectral pattern shown in FIG. 11, carried out on a Bruker-Biospin 4 mm BL CPMAS probe positioned into a wide-bore Bruker-Biospin DSX 500 MHz NMR spectrometer as described in Example 10. The $^{13}$C chemical shifts of S-camsylate polymorph Form A of Compound 1 are shown in Table 10.

TABLE 10

| $^{13}$C Chemical Shifts$^a$ [±0.2 ppm] | Intensity$^b$ |
|---|---|
| 214.7 | 4.3 |
| 213.4 | 4.0 |
| 171.8 | 5.6 |
| 160.7 | 1.8 |
| 160.0 | 2.0 |
| 158.7 | 2.5 |
| 158.0 | 2.5 |
| 137.6 | 4.5 |
| 137.2 | 4.5 |
| 134.9 | 4.1 |
| 134.0 | 4.2 |
| 132.2 | 12.0 |
| 128.8 | 5.8 |
| 127.2 | 11.0 |
| 125.8 | 4.2 |
| 124.7 | 4.1 |
| 123.2 | 5.9 |
| 113.2 | 6.5 |
| 110.1 | 4.8 |
| 102.8 | 2.6 |
| 102.0 | 3.0 |
| 58.6 | 10.1 |
| 53.0 | 4.1 |
| 52.5 | 4.4 |
| 49.3 | 5.9 |
| 48.0 | 9.8 |
| 42.8 | 10.6 |
| 41.8 | 4.7 |
| 37.4 | 3.8 |
| 35.3 | 3.8 |
| 32.5 | 2.8 |
| 31.0 | 2.9 |
| 28.2 | 5.8 |
| 27.0 | 3.5 |
| 25.0 | 3.5 |
| 20.1 | 5.0 |
| 18.4 | 8.8 |
| 17.3 | 4.5 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensitie sare not necessarily quantitative.

Figure 12:
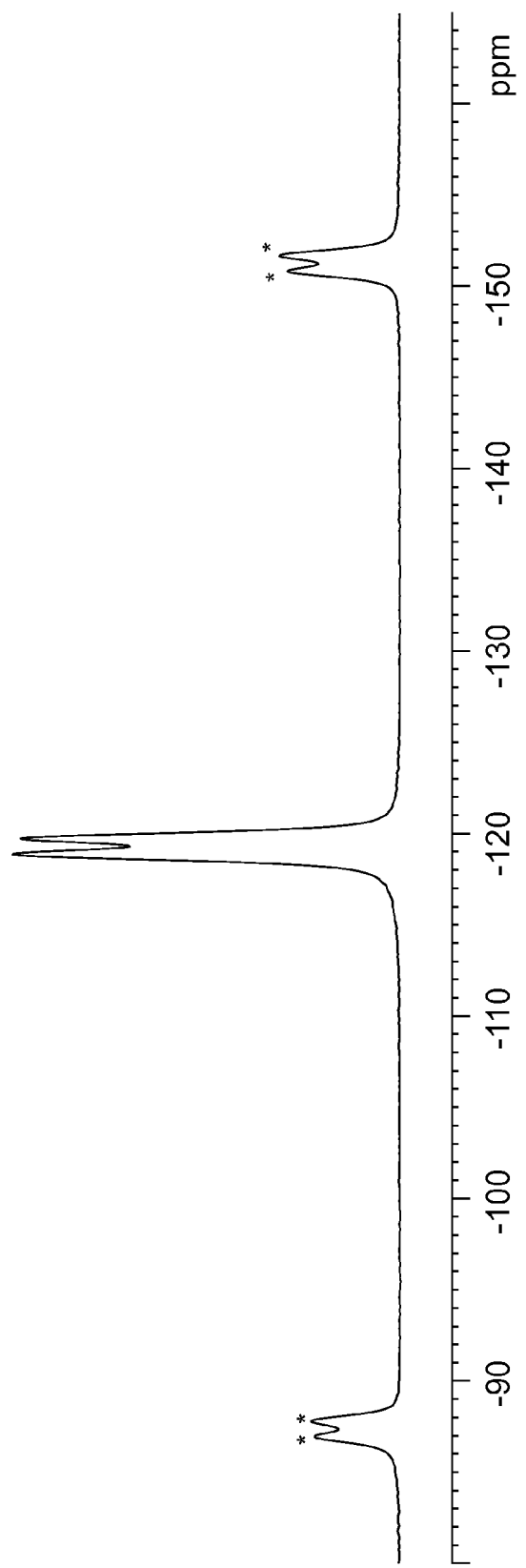
FIG. 12 shows a $^{19}$F solid state NMR spectrum of an S-camsylate salt of Compound 1, polymorph Form A.

The S-camsylate polymorph Form A of Compound 1 was also characterized by the solid state NMR spectral pattern shown in FIG. 12, carried out on a Bruker-Biospin 4 mm BL CPMAS probe positioned into a wide-bore Bruker-Biospin DSX 500 MHz NMR spectrometer as described in Example 10. The $^{19}$F chemical shifts of S-camsylate polymorph Form A of Compound 1 are shown in Table 11.

TABLE 11

| $^{19}$F Chemical Shifts$^a$ [±0.2 ppm] | Intensity$^b$ |
|---|---|
| −118.9 | 12.0 |
| −119.7 | 11.7 |

$^a$Referenced to external standard of trifluoroacetic acid (50% V/V in H$_2$O) at −76.54 ppm.
$^b$Defined as peak heights.

Figure 13:
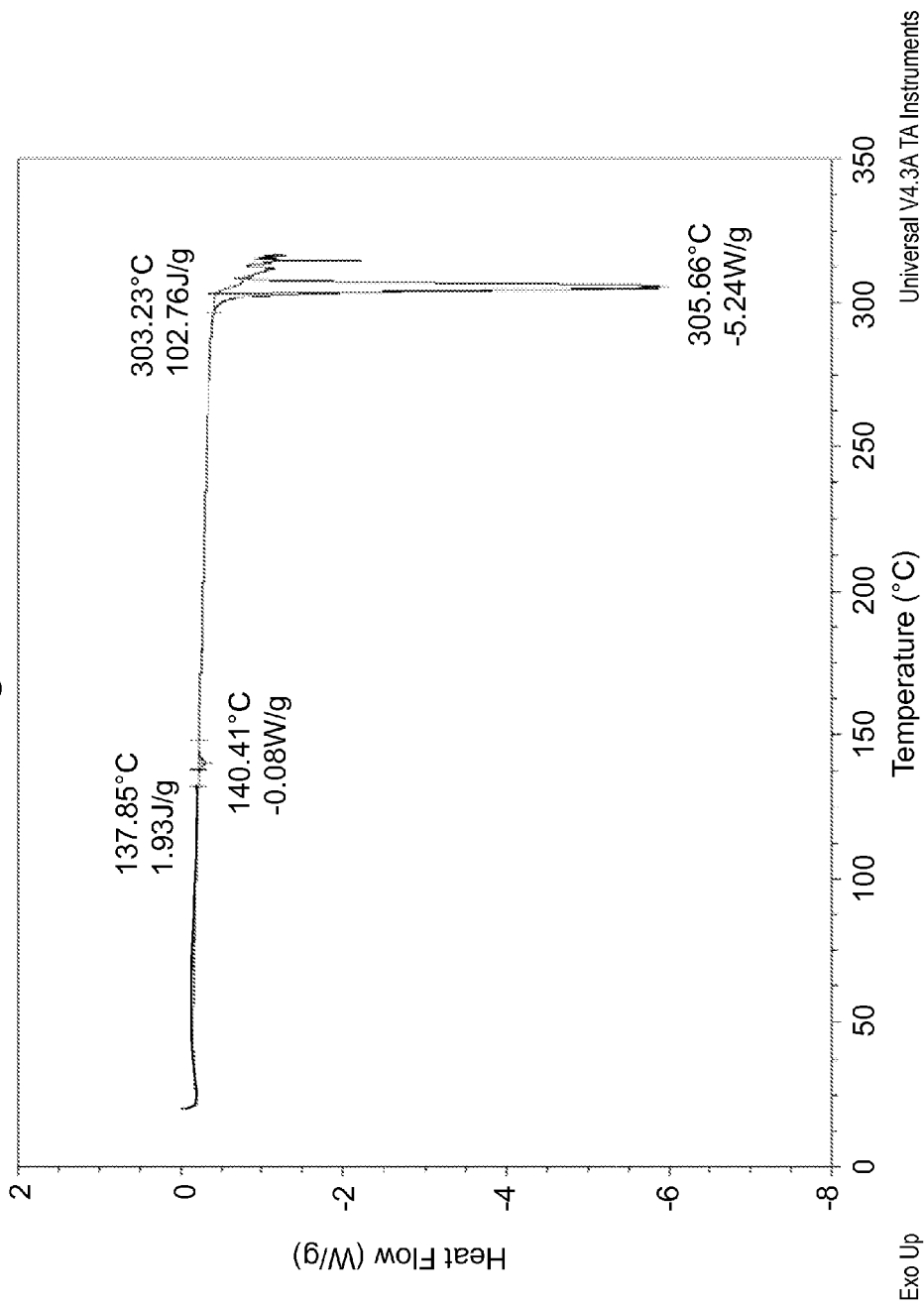
FIG. 13 shows a DSC thermogram of an S-camsylate salt of Compound 1, polymorph Form A.
Figure 14:
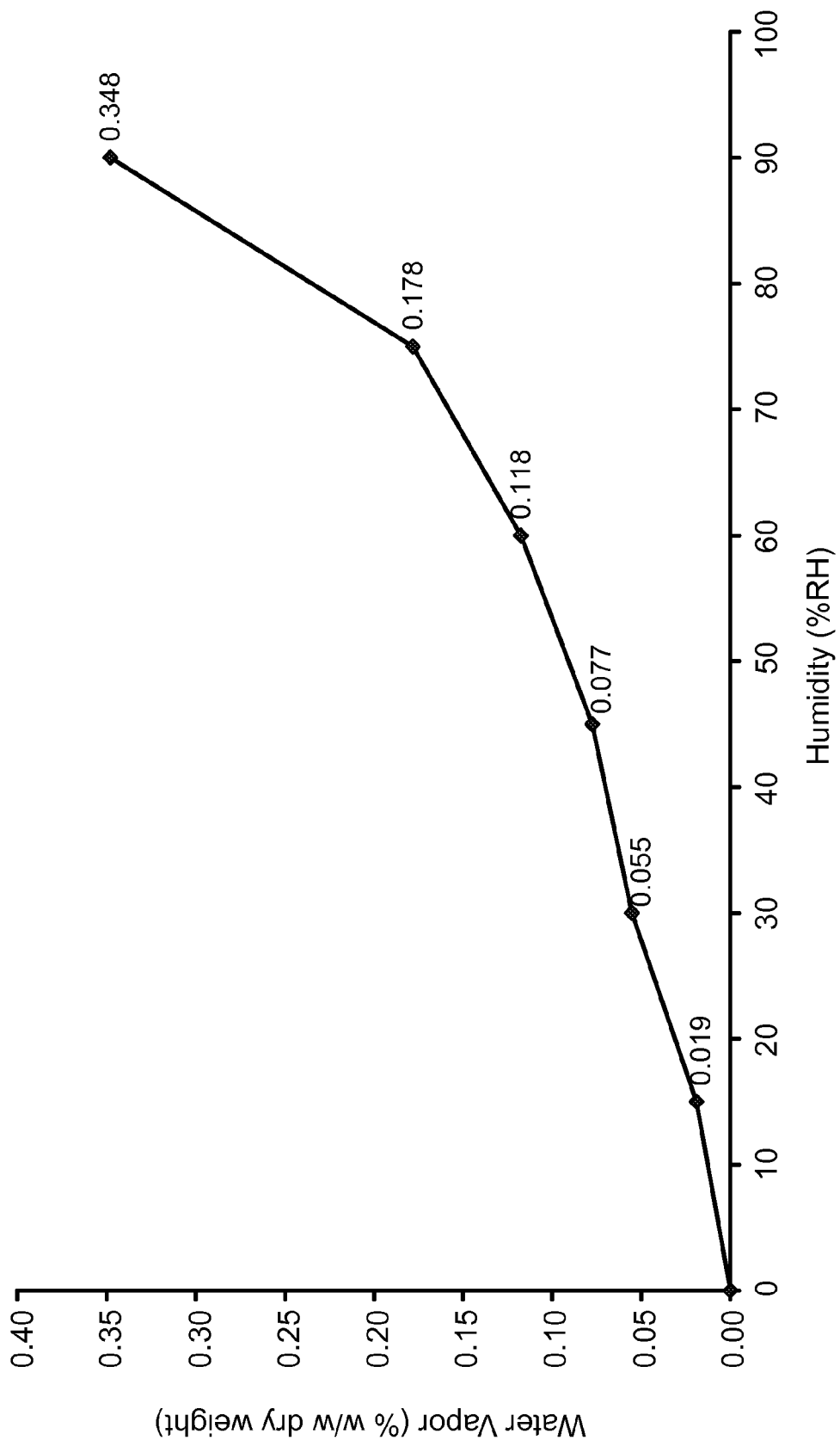
FIG. 14 shows a dynamic vapor sorption isotherm of an S-camsylate salt of Compound 1, S-camsylate polymorph Form A.

The DSC thermogram for S-camsylate polymorph Form A, shown in FIG. 13, indicates an endotherm onset at 303.2° C. The dynamic vapor sorption isotherm for S-camsylate polymorph Form A is shown in FIG. 14. The dynamic vapor sorption isotherm indicates S-camsylate polymorph Form A is non-hygroscopic.

S-camsylate polymorph Form A of Compound 1 was also characterized by Fourier Transform-Infrared Spectroscopy (FT-IR) as described in Example 25, and the spectral peaks are shown in Table 12. Absorption band frequencies are listed. (w: weak, m: medium, s: strong, vs: very strong). Experimental error is ±2 cm$^{-1}$ except for * error on peak position could be considerably larger.

TABLE 12

| Wavenumber (cm$^{-1}$) |
|---|
| 3287 m |
| 3237 m |
| 3074 w |
| 2962 m |
| 2949 w |
| 2892 w |
| 2839 w |
| 1743 s |
| 1637 s |
| 1615 s |
| 1581 w |
| 1510 w |
| 1474 m |
| 1451 m |
| 1415 m |
| 1366 w |
| 1348 w |
| 1315 m |
| 1289 w |
| 1266 m |
| 1255 m |
| 1240 m |
| 1234 m |
| 1226 m |
| 1202 s |
| 1193 s |
| 1151 s |
| 1128 s |
| 1103 s |
| 1066 m |
| 1056 w |
| 1030 s |
| 1015 s |
| 979 w |
| 967 w |
| 958 w |
| 936 w |
| 898 w |
| 870 m |
| 864 m |
| 848 m |
| 834 m |
| 811 m |
| 787 s |
| 753 m |
| 720 m |
| 706 m |
| 674 m |

S-camsylate polymorph Form A of Compound 1 was also characterized by Fourier Transform-Raman Spectroscopy (FT-Raman) as described in Example 26, and the spectral peaks are shown in Table 13. (w: weak, m: medium, s: strong, vs: very strong). Experimental error is ±2 cm$^{-1}$.

TABLE 13

| Wavenumber (cm$^{-1}$) |
|---|
| 3299 w |
| 3230 w |
| 3109 w |
| 3076 w |
| 3059 w |
| 3043 w |
| 3024 w |
| 3000 w |
| 2968 m |
| 2942 w |
| 2922 w |

TABLE 13-continued

| Wavenumber (cm$^{-1}$) |
| --- |
| 2895 w |
| 2843 w |
| 2820 w |
| 2777 w |
| 2736 w |
| 2554 w |
| 1746 w |
| 1617 vs |
| 1581 s |
| 1554 vs |
| 1510 m |
| 1454 vs |
| 1434 m |
| 1419 w |
| 1408 w |
| 1369 m |
| 1348 s |
| 1324 s |
| 1270 w |
| 1251 w |
| 1214 w |
| 1200 w |
| 1160 w |
| 1133 w |
| 1068 s |
| 1041 w |
| 1022 w |
| 939 w |
| 901 w |
| 859 w |
| 816 w |
| 726 w |
| 689 w |
| 645 w |
| 621 w |
| 585 w |
| 550 w |
| 516 w |
| 503 w |
| 430 w |
| 416 w |
| 401 w |
| 370 w |
| 350 w |
| 278 w |
| 261 w |
| 243 w |
| 219 w |
| 158 m |
| 137 w |
| 115 m |
| 84 m |
| 64 s |

D. S-camsylate Salt of Compound 1, S-camsylate Polymorph Form B

Figure 15:
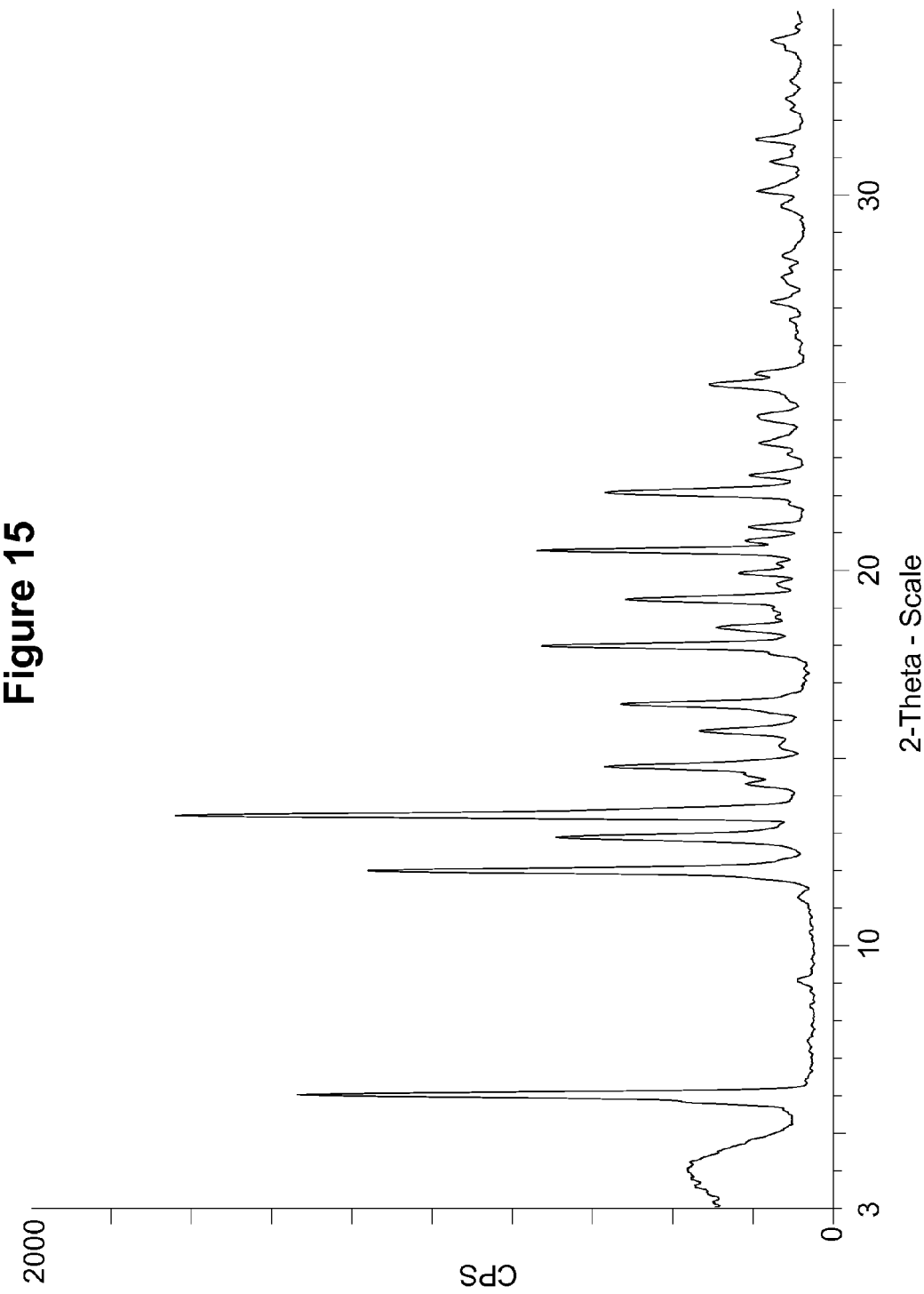
FIG. 15 shows PXRD pattern of an S-camsylate salt of Compound 1, polymorph Form B, using CuKα radiation at 1.5406 Å.

The S-camsylate salt of Compound 1, S-camsylate polymorph Form B, was characterized by the PXRD pattern shown in FIG. 15.

E. Hydrochloride Salt Trihydrate Polymorph of Compound 1

Figure 17:
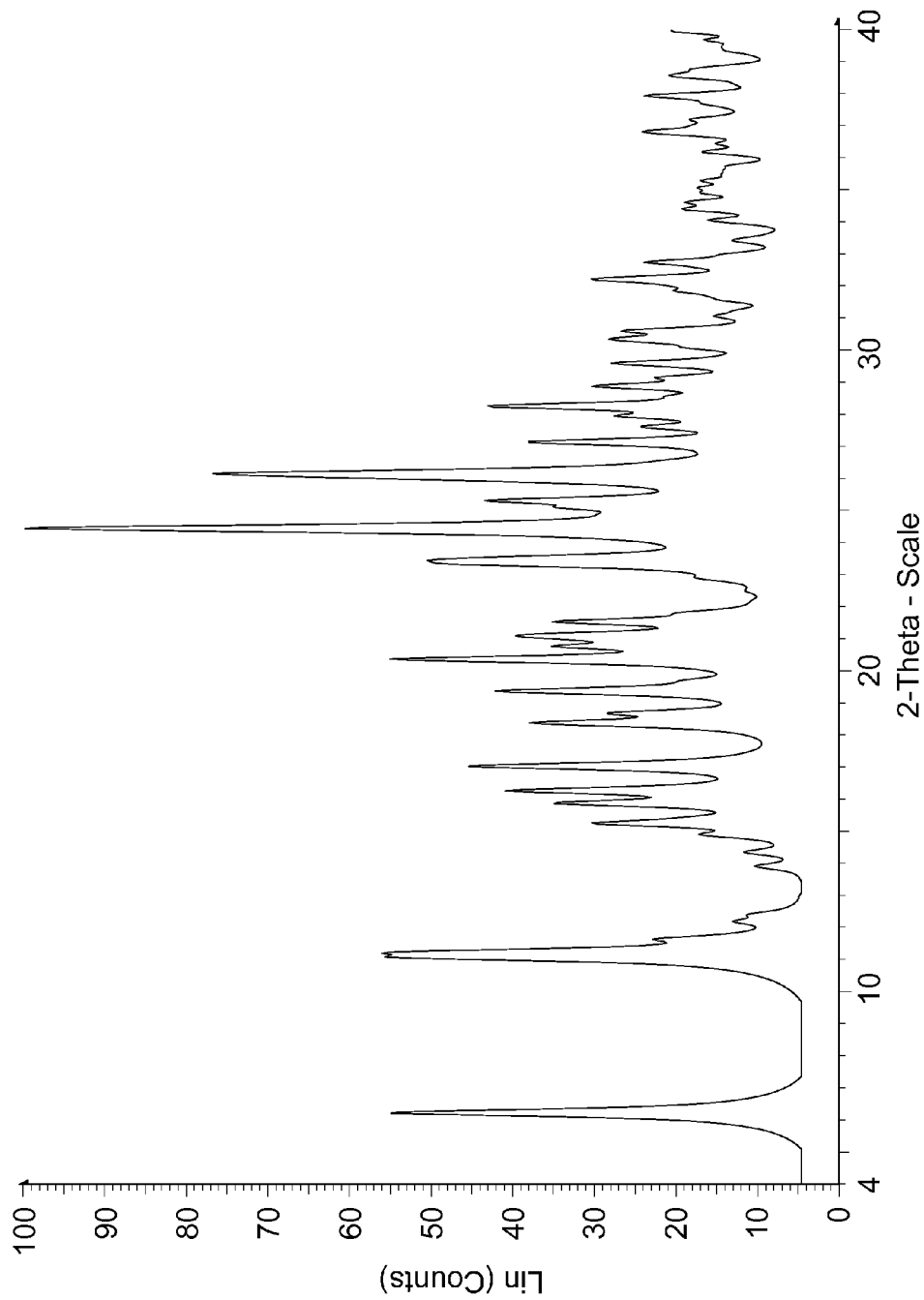
FIG. 17 shows a simulated PXRD pattern of a hydrochloride salt trihydrate of Compound 1, using CuKα radiation at 1.5406 Å.

A hydrochloride salt trihydrate polymorph of Compound 1 was characterized by the simulated PXRD pattern calculated from a single crystal structure, as shown in FIG. 17, using CuKα radiation at 1.5406 Å. The simulated PXRD pattern of the hydrochloride salt trihydrate polymorph, expressed in terms of the degree (2θ) and relative intensities with a relative intensity of ≥15.0%, is also shown in Table 14.

TABLE 14

| Angle (Degree 2θ) | Relative Intensity (≥15.0%) |
| --- | --- |
| 6.2 | 55.1 |
| 11.0 | 56.5 |
| 11.2 | 56.7 |
| 11.6 | 23.1 |
| 14.9 | 17.6 |
| 15.2 | 31.5 |
| 15.9 | 35.3 |
| 16.2 | 40.9 |
| 17.0 | 45.4 |
| 18.4 | 37.9 |
| 18.7 | 28.9 |
| 19.4 | 42.1 |
| 19.7 | 20.3 |
| 20.3 | 55.1 |
| 20.7 | 35.7 |
| 21.1 | 39.6 |
| 21.5 | 35.1 |
| 21.8 | 20.5 |
| 22.9 | 18.3 |
| 23.4 | 50.5 |
| 24.5 | 100.0 |
| 25.1 | 35.4 |
| 25.3 | 43.4 |
| 26.1 | 76.9 |
| 27.1 | 38.0 |
| 27.6 | 24.6 |
| 28.0 | 28.1 |
| 28.3 | 43.0 |
| 28.6 | 22.0 |
| 28.9 | 30.7 |
| 29.2 | 23.2 |
| 29.6 | 27.9 |
| 30.1 | 19.9 |
| 30.4 | 29.0 |
| 30.6 | 27.2 |
| 31.1 | 16.3 |
| 31.9 | 20.8 |
| 32.2 | 30.3 |
| 32.8 | 24.6 |
| 34.1 | 16.0 |
| 34.4 | 19.5 |
| 34.7 | 19.5 |
| 35.3 | 17.3 |
| 36.2 | 17.4 |
| 36.5 | 15.7 |
| 36.8 | 24.3 |
| 37.2 | 18.9 |
| 37.7 | 17.6 |
| 38.0 | 23.8 |
| 38.6 | 20.7 |
| 38.8 | 18.6 |
| 39.7 | 17.9 |

F. S-camsylate Salt of Compound 1, S-camsylate Polymorph Form C

The S-camsylate salt of Compound 1, S-camsylate polymorph Form C, can be produced as described in Example 16.

Figure 18:
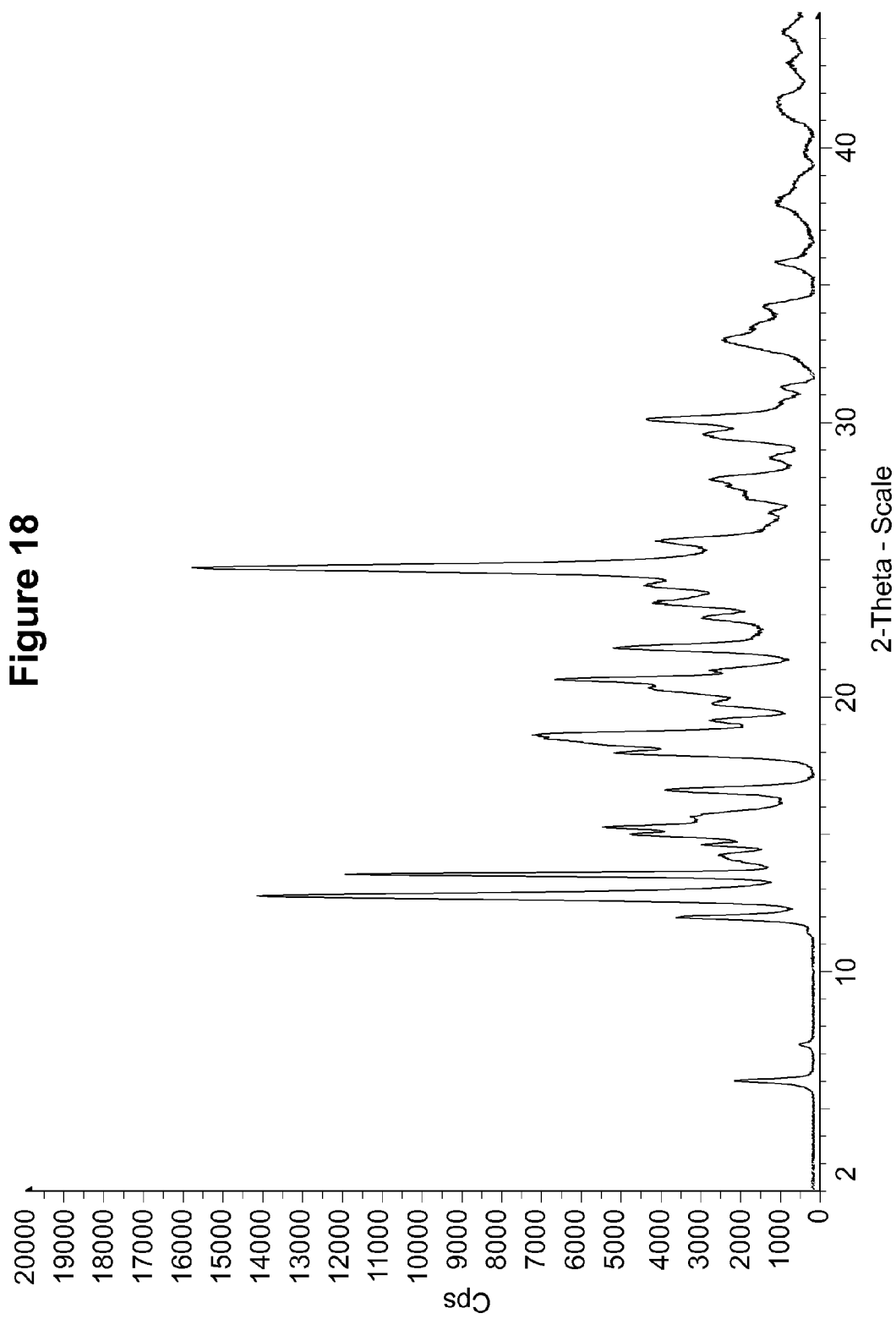
FIG. 18 shows an experimental PXRD pattern of an S-camsylate salt of Compound 1, polymorph Form C, using CuKα radiation at 1.5406 Å.
Figure 19:
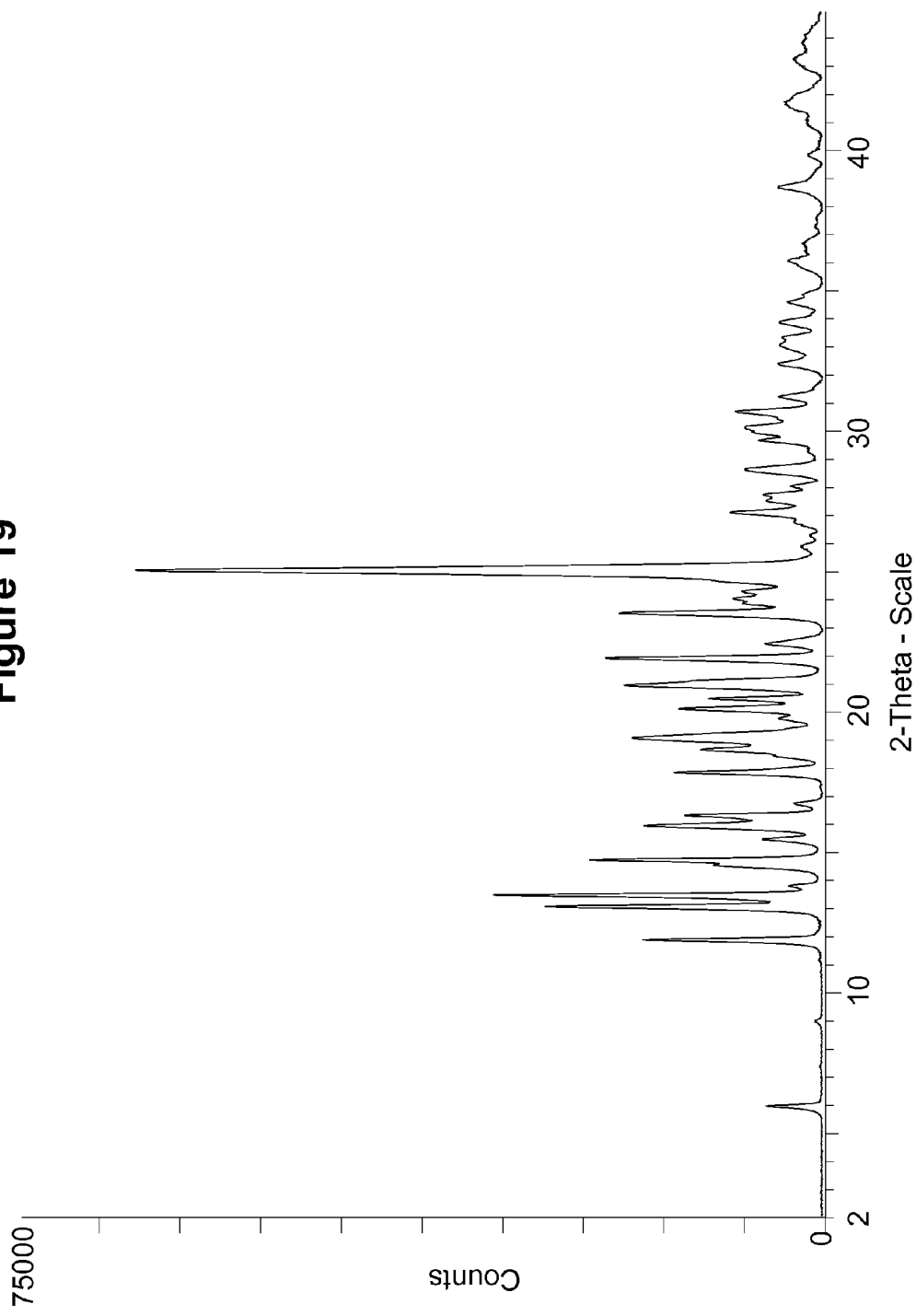
FIG. 19 shows an experimental PXRD pattern of a 1R:1S-camsylate salt, using CuKα radiation at 1.5406 Å.
Figure 20:
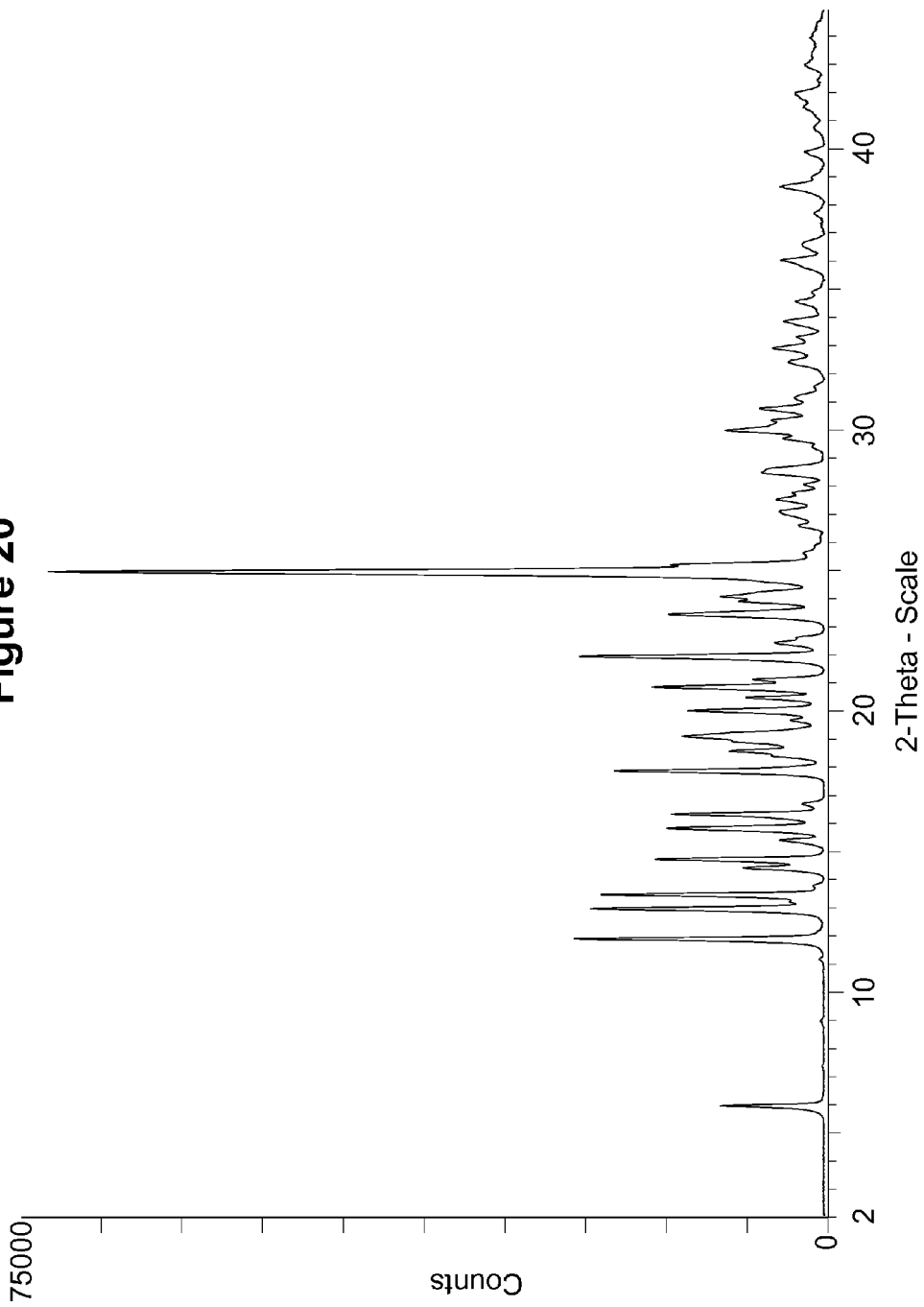
FIG. 20 shows an experimental PXRD pattern of a 1R:9S-camsylate salt, using CuKα radiation at 1.5406 Å.
Figure 21:
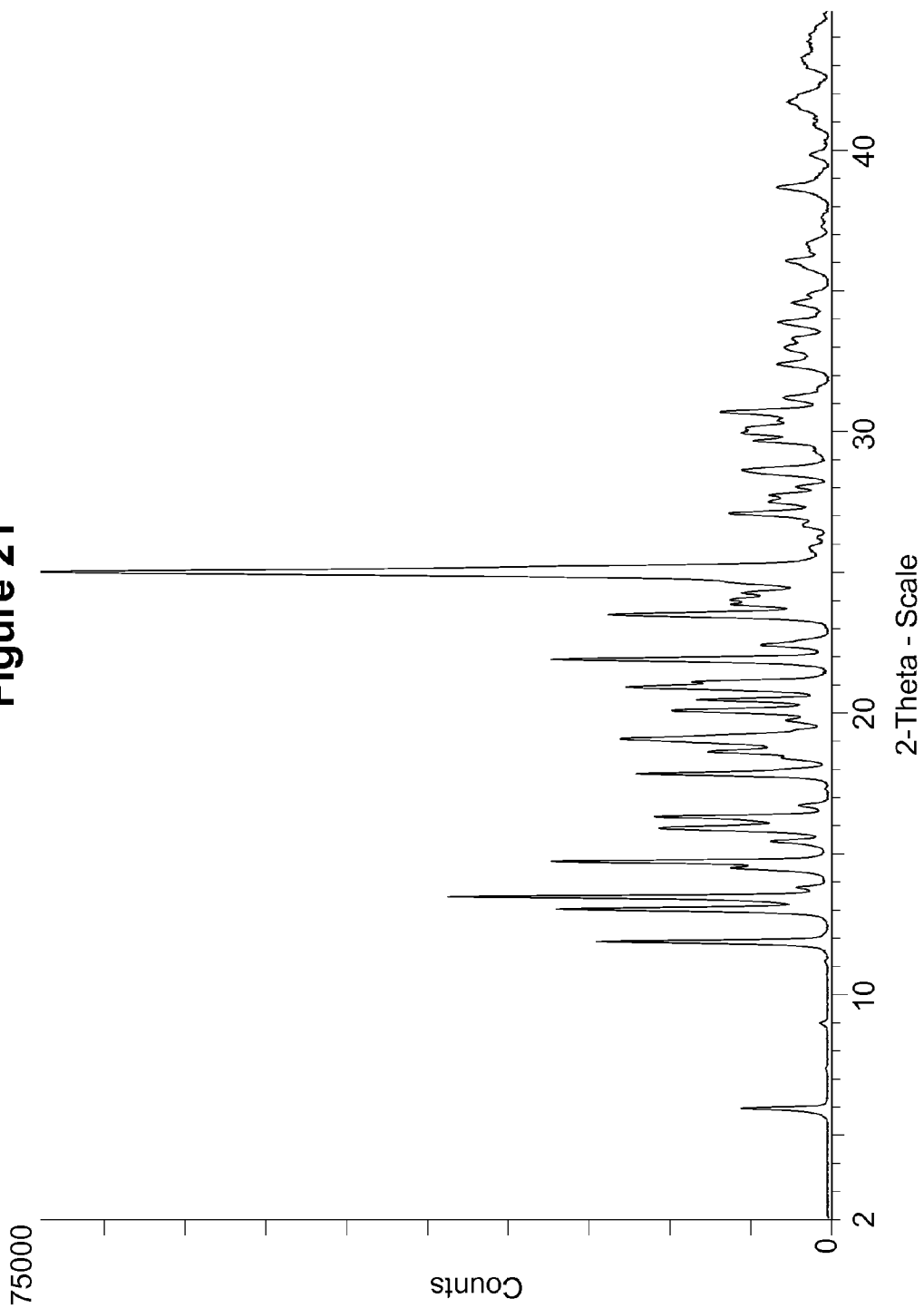
FIG. 21 shows an experimental PXRD pattern of a 1R:3S-camsylate salt, using CuKα radiation at 1.5406 Å.
Figure 22:
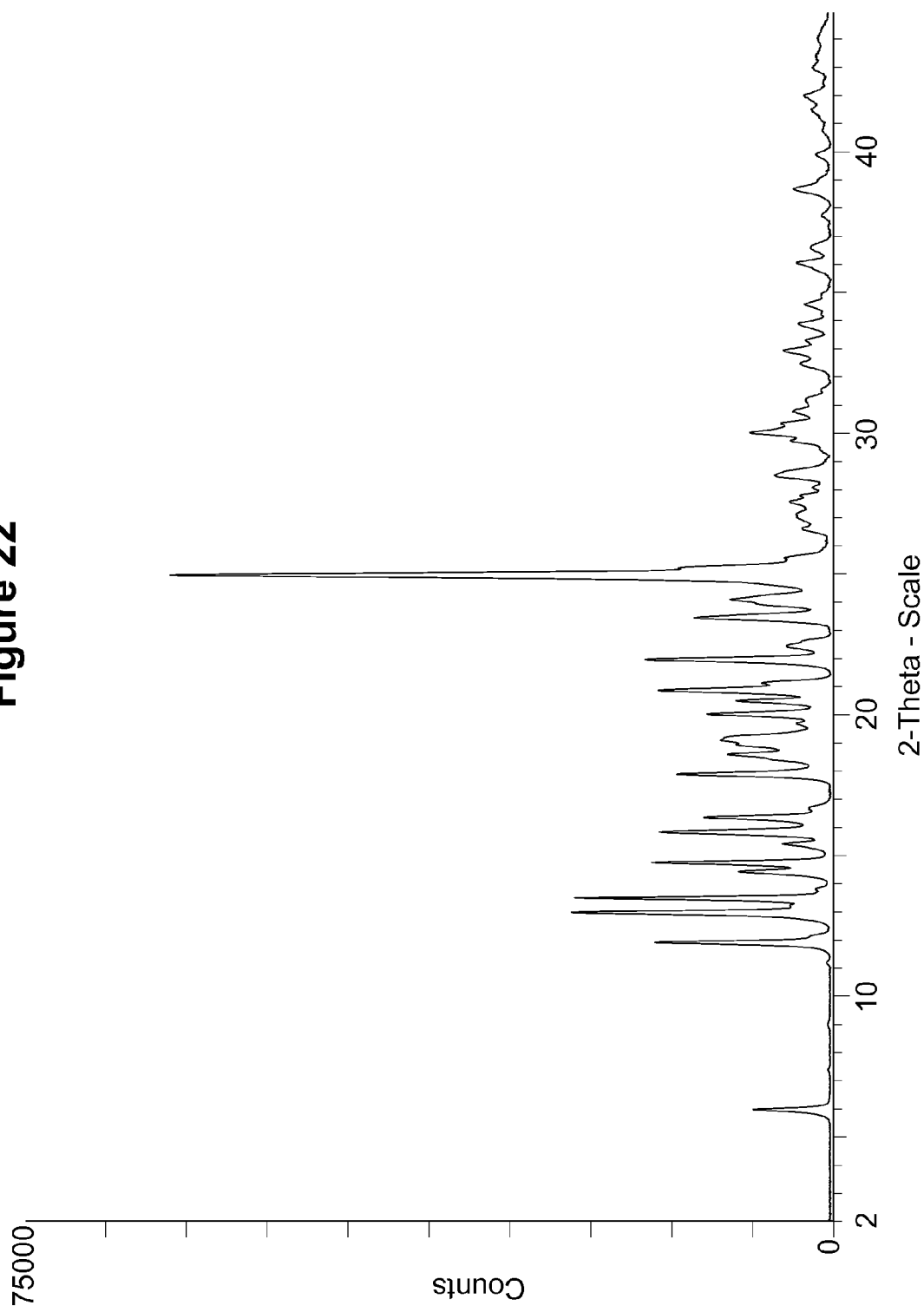
FIG. 22 shows an experimental PXRD pattern of a 1R:7S-camsylate salt, using CuKα radiation at 1.5406 Å.

S-camsylate polymorph Form C was characterized by measuring the PXRD pattern for a particular batch of S-camsylate polymorph Form C. This experimental PXRD pattern is shown in FIG. 18. The experimental PXRD pattern of S-camsylate polymorph Form C, expressed in terms of the degree (2θ) and relative intensities with a relative intensity greater than 10.0%, measured on a Bruker-AXS Ltd., D4 diffractometer with CuKα radiation at 1.5406 Å, is also shown in Table 15.

TABLE 15

| Angle (Degree 2θ ± 0.1°) | Relative Intensity (>10.0%) |
|---|---|
| 6.0 | 13.4 |
| 11.9 | 22.7 |
| 12.7 | 89.6 |
| 13.5 | 75.6 |
| 14.2 | 16.0 |
| 14.6 | 18.8 |
| 15.0 | 33.2 |
| 15.2 | 34.5 |
| 16.6 | 24.5 |
| 17.9 | 32.7 |
| 18.6 | 45.7 |
| 19.1 | 17.2 |
| 19.7 | 17.1 |
| 20.6 | 42.2 |
| 21.0 | 17.5 |
| 21.8 | 32.8 |
| 22.9 | 18.8 |
| 23.4 | 26.6 |
| 24.0 | 27.8 |
| 24.7 | 100.0 |
| 25.7 | 26.1 |
| 27.9 | 17.4 |
| 29.6 | 18.4 |
| 30.1 | 27.6 |
| 33.0 | 15.4 |

Figure 28:
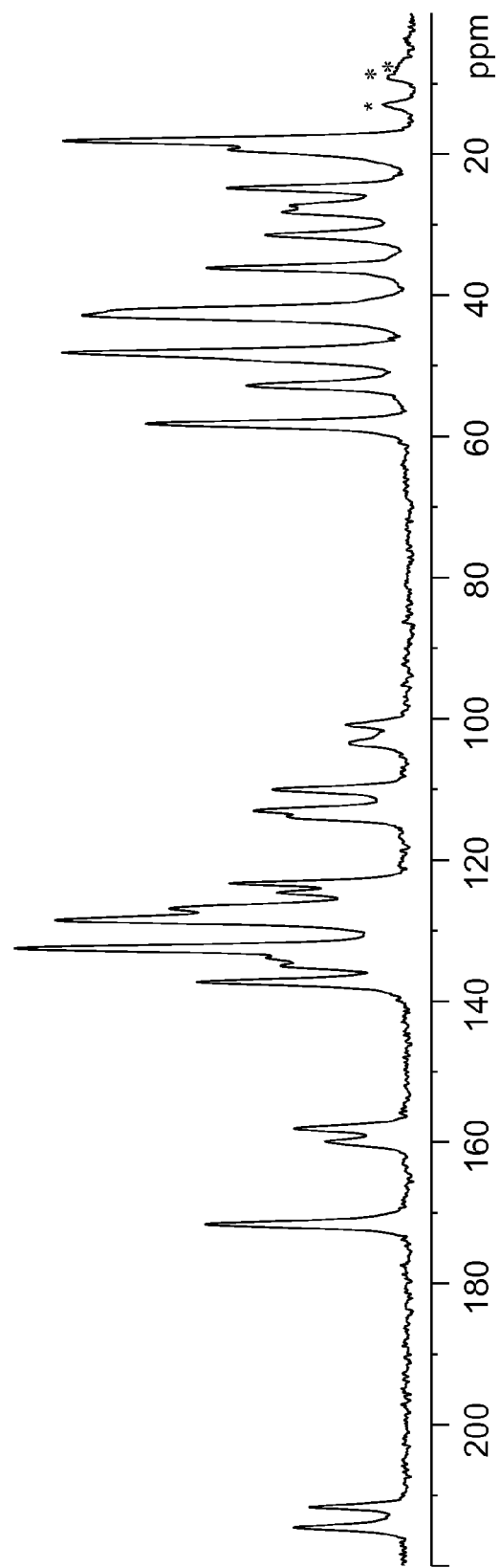
FIG. 28 shows a $^{13}$C solid state NMR spectrum of an S-camsylate salt of Compound 1, polymorph Form C.

S-camsylate polymorph Form C of Compound 1 was also characterized by the solid state NMR spectral pattern shown in FIG. 28, carried out on a Bruker-Biospin 4 mm BL CPMAS probe positioned into a wide-bore Bruker-Biospin DSX 500 MHz NMR spectrometer as described in Example 23. The $^{13}$C chemical shifts of S-camsylate polymorph Form A of Compound 1 are shown in Table 16.

TABLE 16

| $^{13}$C Chemical Shifts[a] [ppm] | Intensity[b] |
|---|---|
| 214.6 | 3.6 |
| 211.7 | 3.0 |
| 171.6 | 6.2 |
| 159.9 | 2.6 |
| 158.0 | 3.5 |
| 137.3 | 6.5 |
| 135.0 | 3.8 |
| 133.9 | 4.2 |
| 132.5 | 12.0 |
| 128.5 | 10.6 |
| 126.9 | 7.2 |
| 124.6 | 4.1 |
| 123.3 | 5.6 |
| 113.8 | 3.7 |
| 113.1 | 4.8 |
| 110.0 | 4.3 |
| 103.4 | 1.9 |
| 100.8 | 2.0 |
| 58.2 | 8.0 |
| 52.8 | 4.9 |
| 48.1 | 10.6 |
| 42.9 | 9.8 |
| 42.2 | 9.1 |
| 36.1 | 6.4 |
| 31.5 | 4.4 |
| 28.3 | 3.9 |
| 27.3 | 3.7 |
| 24.8 | 5.8 |
| 19.4 | 5.4 |
| 18.1 | 3.6 |

[a]Referenced to external sample of solid phase adamantane at 29.5 ppm.
[b]Defined as peak heights. Intensities can vary depending on the actual setup of the CPMAS experimental parameters and the thermal history of the sample. CPMAS intensities are not necessarily quantitative.

Figure 29:
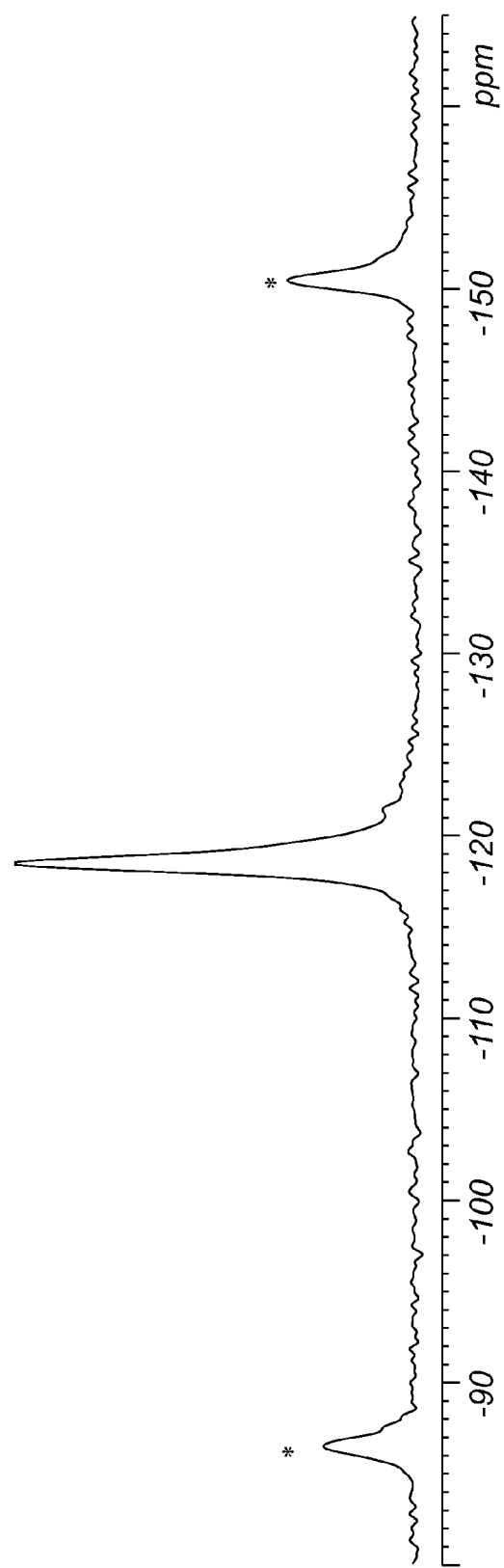
FIG. 29 shows a $^{19}$F solid state NMR spectrum of an S-camsylate salt of Compound 1, polymorph Form C.

The S-camsylate polymorph Form C of Compound 1 was also characterized by the solid state NMR spectral pattern shown in FIG. 29, carried out on a Bruker-Biospin 4 mm BL CPMAS probe positioned into a wide-bore Bruker-Biospin DSX 500 MHz NMR spectrometer as described in Example 23. The $^{19}$F chemical shifts of S-camsylate polymorph Form A of Compound 1 are shown in Table 17.

TABLE 17

| $^{19}$F Chemical Shifts[a] [ppm] | Intensity[b] |
|---|---|
| −118.5 | 12.0 |

[a]Referenced to external standard of trifluoroacetic acid (50% V/V in $H_2O$) at −76.54 ppm.
[b]Defined as peak heights.

Figure 24:
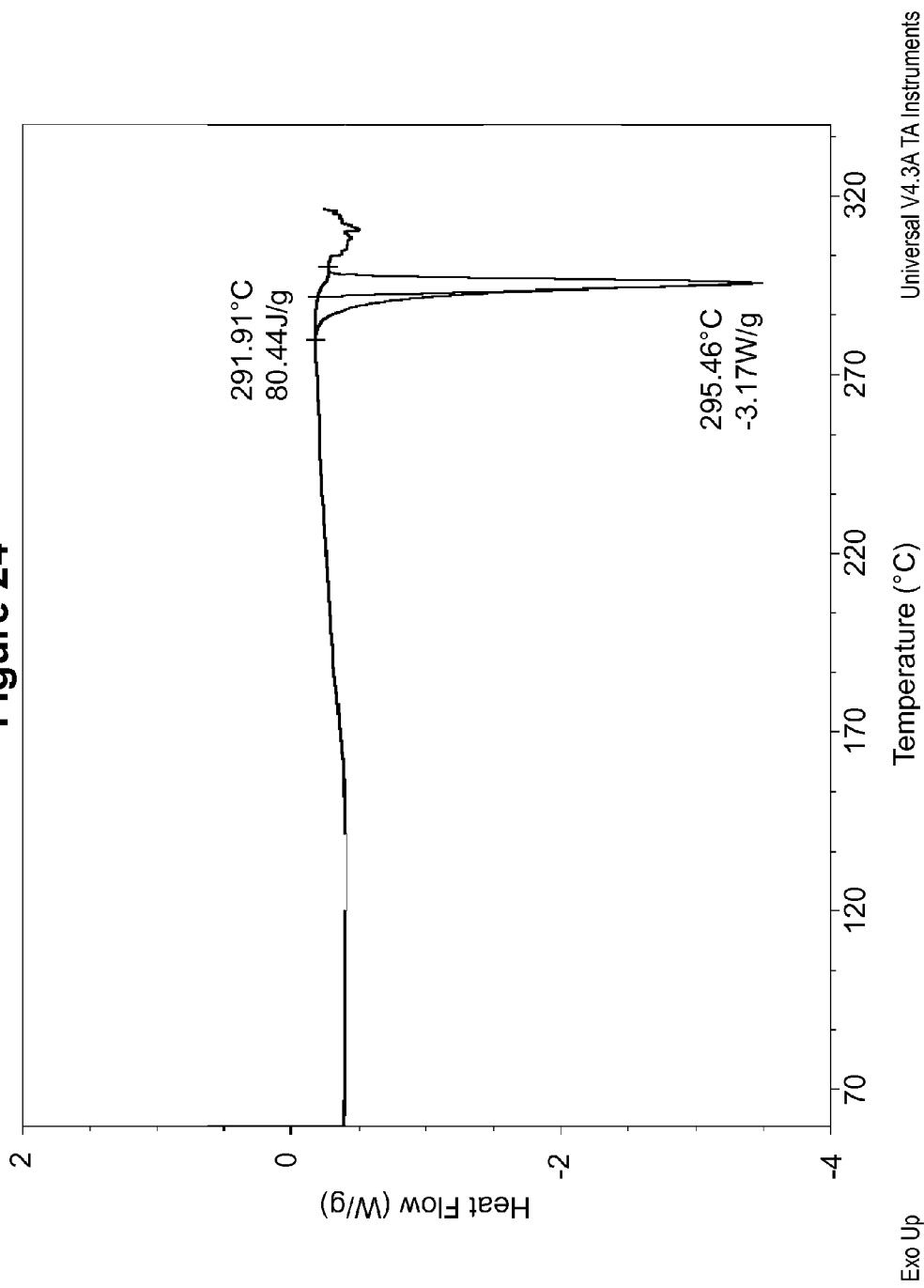
FIG. 24 shows a DSC thermogram of an S-camsylate salt of Compound 1, polymorph Form C.

The DSC thermogram for S-camsylate polymorph Form C, shown in FIG. 24, indicates an endotherm onset at 291.9° C.

S-camsylate polymorph Form C of Compound 1 was also characterized by Fourier Transform-Infrared Spectroscopy (FT-IR) as described in Example 25, and the spectral peaks are shown in Table 18. Absorption band frequencies are listed. (w: weak, m: medium, s: strong, vs: very strong). Experimental error is ±2 cm$^{-1}$ except for * error on peak position could be considerably larger.

TABLE 18

| Wavenumber (cm$^{-1}$) |
|---|
| 3284 m |
| 3074 w |
| 3024 w |
| 2962 m |
| 2912 w |
| 2891 w |
| 2839 w |
| 2581 w |
| 1753 m |
| 1743 m |
| 1637 m |
| 1615 s |
| 1582 w |
| 1513 w |
| 1472 m |
| 1451 s |
| 1415 m |
| 1367 w |
| 1346 m |
| 1324 m |
| 1315 m |
| 1261 m |
| 1240 s |
| 1204 m |
| 1192 m |
| 1175 m |
| 1153 s |
| 1131 s |
| 1106 s |
| 1067 m |
| 1030 s |
| 1024 s |
| 965 w |
| 958 w |
| 937 w |
| 899 w |
| 871 m |
| 843 m |
| 810 m |
| 787 s |
| 752 w |
| 721 w |
| 706 w |
| 674 m |

S-camsylate polymorph Form C of Compound 1 was also characterized by Fourier Transform-Raman Spectroscopy (FT-Raman) as described in Example 26, and the spectral peaks are shown in Table 19. (w: weak, m: medium, s: strong, vs: very strong). Experimental error is ±2 cm$^{-1}$.

TABLE 19

| Wavenumber (cm$^{-1}$) |
| --- |
| 3291 w* |
| 3229 w |
| 3074 w |
| 3057 w |
| 3029 w |
| 2967 w |
| 2946 w |
| 2915 w |
| 2892 w |
| 2844 w |
| 2819 w |
| 2777 w |
| 2732 w |
| 2554 w |
| 1755 w |
| 1745 w |
| 1617 vs |
| 1579 s |
| 1555 vs |
| 1511 w |
| 1454 vs |
| 1408 w |
| 1369 m |
| 1348 m |
| 1324 m |
| 1269 w |
| 1250 w |
| 1217 w |
| 1204 w |
| 1164 w |
| 1134 w |
| 1069 s |
| 1041 w |
| 1022 w |
| 960 w |
| 939 w |
| 902 w |
| 859 w |
| 815 w |
| 791 w |
| 726 w |
| 708 w |
| 683 w |
| 646 w |
| 636 w |
| 616 w |
| 582 w |
| 549 w |
| 504 w |
| 485 w |
| 430 w |
| 413 w |
| 370 w |
| 350 w |
| 275 w |
| 262 w |
| 242 w |
| 222 w |
| 160 w |
| 114 m |
| 89 m |
| 61 m |

G. R-Camsylate and S-Camsylate Salts

Various camsylate salts with different R:S ratios of camphor sulfonic acid were produced and characterized. The 1R:1S-camsylate salt, the 1R:9S-camsylate salt, the 1R:3S-camsylate salt, and the 1R:7S-camsylate salt can be produced as described in Examples 17-20.

The 1R:1S-camsylate salt, the 1R:9S-camsylate salt, the 1R:3S-camsylate salt, and the 1R:7S-camsylate salt were characterized by measuring the PXRD pattern for a particular batch of each salt. These experimental PXRD patterns are shown in FIGS. 19-22. The PXRD patterns for these salts indicate that the packing of the molecules within the crystal lattice of these mixed salts were roughly equivalent. Minor changes in the molecular packing density resulted to accommodate the differing ratios of S and R camphor sulfonic acid in the lattice. This change in packing density resulted in small shifts in peak position for certain of the peaks in the PXRD patterns. Camsylate salts containing different ratios of the R and S camphor sulfonic acid, to those described herein, could also be formed, and these salts would have roughly equivalent crystal lattices.

The experimental PXRD pattern of the 1R:1S-camsylate salt, expressed in terms of the degree (2θ) and relative intensities with a relative intensity greater than 10.0%, measured on a Bruker-AXS Ltd., D4 diffractometer with CuKα radiation at 1.5406 Å, is also shown in Table 20.

TABLE 20

| Angle (Degree 2θ ± 0.1°) | Relative Intensity (>10.0%) |
| --- | --- |
| 11.9 | 26.1 |
| 13.1 | 40.2 |
| 13.5 | 47.5 |
| 14.7 | 34.1 |
| 16.0 | 26.6 |
| 16.3 | 20.9 |
| 17.9 | 22.7 |
| 18.7 | 19.2 |
| 19.1 | 29.0 |
| 20.1 | 22.7 |
| 20.5 | 18.6 |
| 21.0 | 30.6 |
| 21.9 | 33.3 |
| 22.5 | 10.9 |
| 23.5 | 31.5 |
| 23.9 | 14.2 |
| 24.3 | 14.4 |
| 25.1 | 100.0 |
| 27.1 | 16.1 |
| 27.8 | 11.3 |
| 28.7 | 13.8 |
| 29.7 | 11.6 |
| 30.2 | 13.2 |
| 30.7 | 14.4 |

Figure 30:
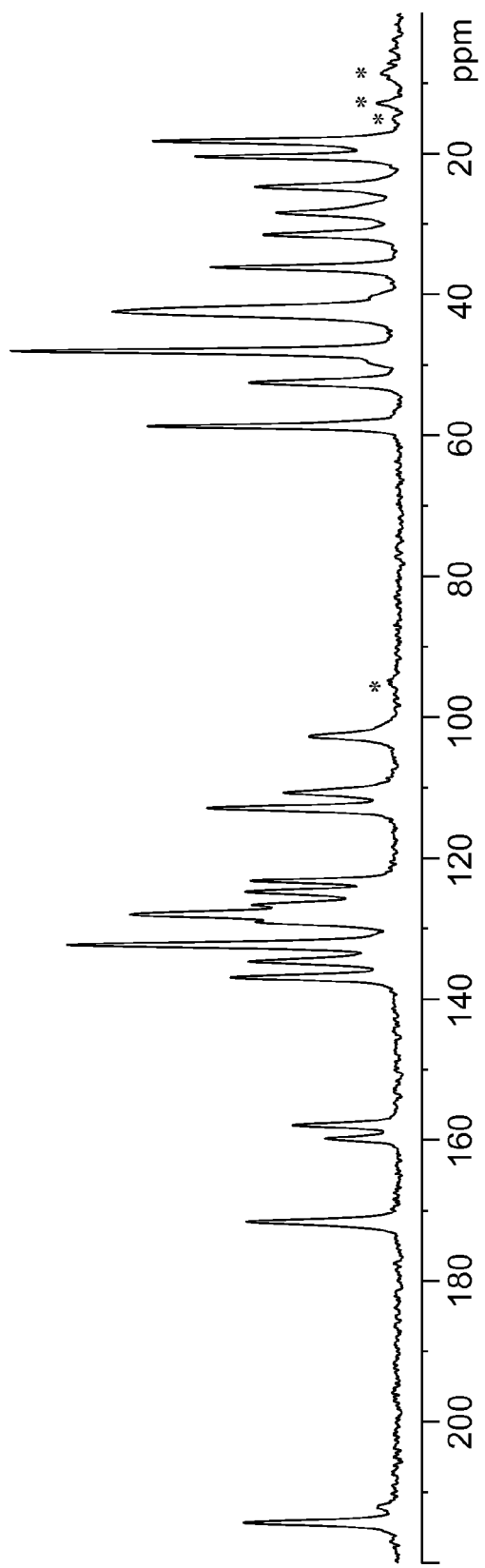
FIG. 30 shows a $^{13}$C solid state NMR spectrum of a 1R:1S-camsylate salt.
Figure 32:
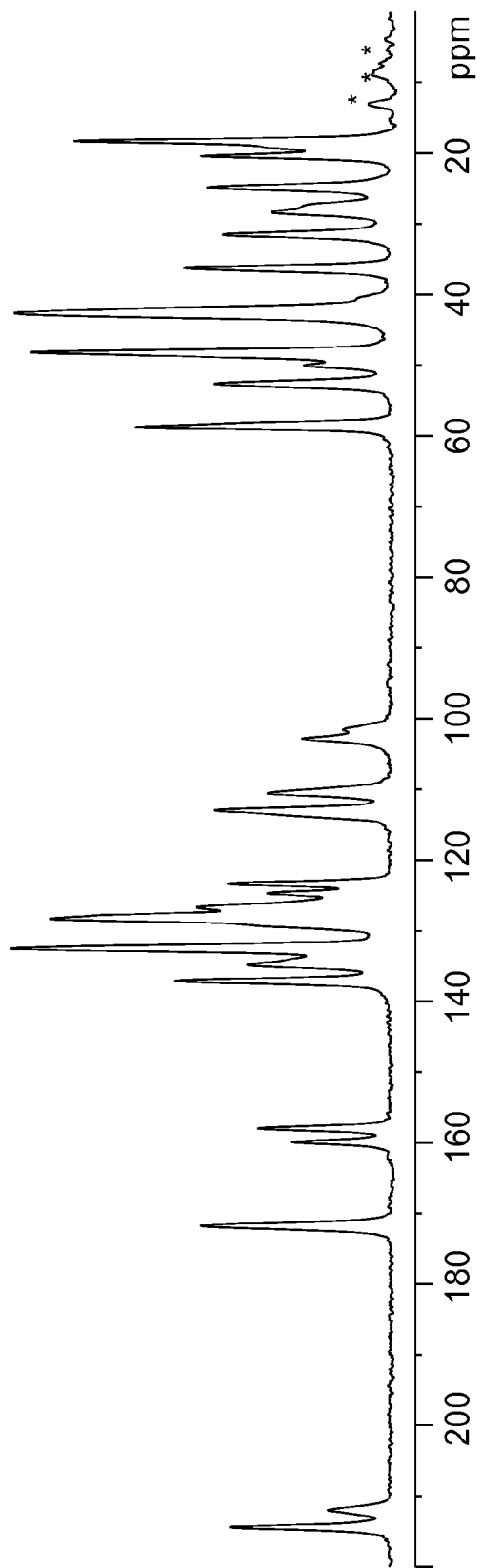
FIG. 32 shows a $^{13}$C solid state NMR spectrum of a 1R:9S-camsylate salt.

The 1R:1S-camsylate salt and the 1R:9S-camsylate salt were also characterized by the solid state NMR spectral pattern shown in FIGS. 30 and 32, carried out on a Bruker-Biospin 4 mm BL CPMAS probe positioned into a wide-bore Bruker-Biospin DSX 500 MHz NMR spectrometer as described in Example 24. The $^{13}$C chemical shifts of the 1R:1S-camsylate salt is shown in Table 21.

TABLE 21

| $^{13}$C Chemical Shifts$^a$ [ppm] | Intensity$^b$ |
| --- | --- |
| 214.3 | 4.8 |
| 212.2 | 0.6 |
| 171.6 | 4.7 |
| 159.8 | 2.2 |
| 157.9 | 3.2 |
| 136.9 | 5.2 |
| 134.7 | 4.6 |
| 132.3 | 10.3 |
| 129.0 | 4.4 |
| 128.0 | 8.3 |

TABLE 21-continued

| $^{13}$C Chemical Shifts$^a$ [ppm] | Intensity$^b$ |
|---|---|
| 126.6 | 4.5 |
| 124.8 | 4.7 |
| 123.2 | 4.6 |
| 112.9 | 5.9 |
| 110.7 | 3.5 |
| 102.7 | 2.7 |
| 58.7 | 7.8 |
| 52.5 | 4.6 |
| 49.6 | 0.9 |
| 48.0 | 12.0 |
| 42.4 | 8.8 |
| 40.5 | 0.9 |
| 36.1 | 5.8 |
| 31.5 | 4.2 |
| 28.4 | 3.7 |
| 24.7 | 4.4 |
| 20.5 | 6.3 |
| 18.2 | 7.6 |

$^a$Referenced to external sample of crystalline adamantane at 29.5 ppm.
$^b$Defined as peak heights. Intensities can vary depending on the actual setup of the CPMAS experimental parameters and the thermal history of the sample. CPMAS intensities are not necessarily quantitative.

The $^{13}$C chemical shifts of the 1R:9S-camsylate salt is shown in Table 22.

TABLE 22

| $^{13}$C Chemical Shifts$^a$ [ppm] | Intensity$^b$ |
|---|---|
| 214.4 | 5.1 |
| 212.0 | 2.0 |
| 171.8 | 6.0 |
| 159.9 | 3.1 |
| 158.0 | 4.2 |
| 137.1 | 6.8 |
| 134.8 | 4.5 |
| 132.5 | 12.0 |
| 128.3 | 10.8 |
| 126.7 | 6.1 |
| 124.7 | 3.9 |
| 123.3 | 5.1 |
| 112.9 | 5.6 |
| 110.5 | 3.9 |
| 102.8 | 2.8 |
| 101.6 | 1.5 |
| 58.7 | 8.1 |
| 52.6 | 5.6 |
| 50.0 | 2.7 |
| 48.2 | 11.4 |
| 42.6 | 11.9 |
| 40.6$^c$ | 1.1 |
| 36.2 | 6.5 |
| 31.5 | 5.3 |
| 28.4 | 3.8 |
| 27.6$^c$ | 2.8 |
| 24.8 | 5.8 |
| 20.4 | 6.0 |
| 19.2$^c$ | 3.9 |
| 18.3 | 10.0 |

$^a$Referenced to external sample of crystalline adamantane at 29.5 ppm.
$^b$Defined as peak heights. Intensities can vary depending on the actual setup of the CPMAS experimental parameters and the thermal history of the sample. CPMAS intensities are not necessarily quantitative.
$^c$Peak shoulder.

Figure 31:
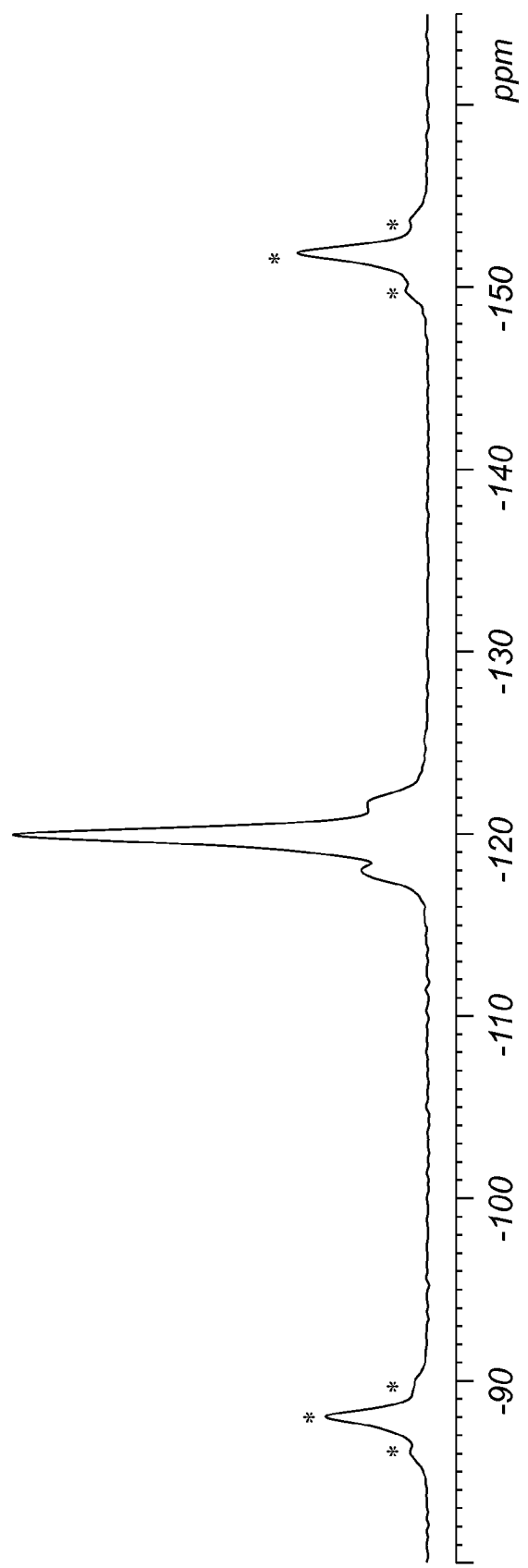
FIG. 31 shows a $^{19}$F solid state NMR spectrum of a 1R:1S-camsylate salt.
Figure 33:
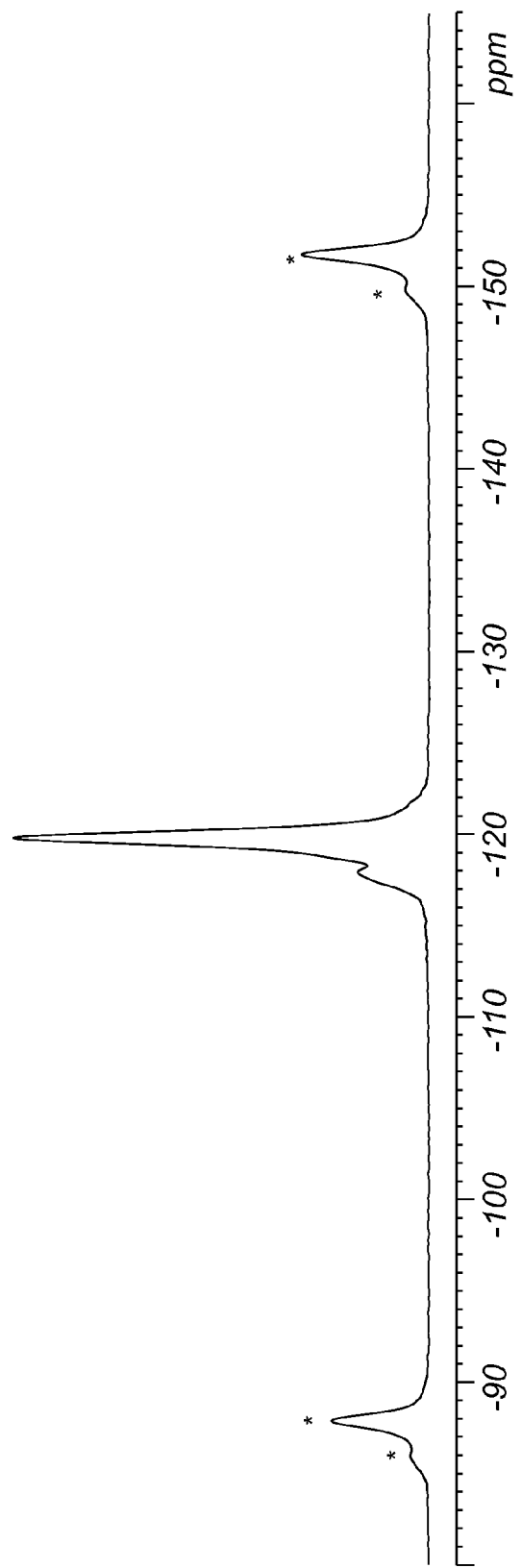
FIG. 33 shows a $^{19}$F solid state NMR spectrum of a 1R:9S-camsylate salt.

The 1R:1S-camsylate salt and the 1R:9S-camsylate salt were also characterized by the solid state NMR spectral pattern shown in FIGS. 31 and 33, carried out on a Bruker-Biospin 4 mm BL CPMAS probe positioned into a wide-bore Bruker-Biospin DSX 500 MHz NMR spectrometer as described in Example 23. The $^{19}$F chemical shifts of the 1R:1S-camsylate salt are shown in Table 23.

TABLE 23

| $^{19}$F Chemical Shifts$^a$ [ppm] | Intensity$^b$ |
|---|---|
| −118.0 | 1.9 |
| −119.9 | 12.0 |
| −121.6 | 1.8 |

$^a$Referenced to external standard of trifluoroacetic acid (50% V/V in H$_2$O) at −76.54 ppm.
$^b$Defined as peak heights.

The $^{19}$F chemical shifts of the 1R:9S-camsylate salt are shown in Table 24.

TABLE 24

| $^{19}$F Chemical Shifts$^a$ [ppm] | Intensity$^b$ |
|---|---|
| −117.9 | 2.0 |
| −119.8 | 12.0 |

$^a$Referenced to external sample of crystalline adamantane at 29.5 ppm.
$^b$Defined as peak heights.

Figure 25:
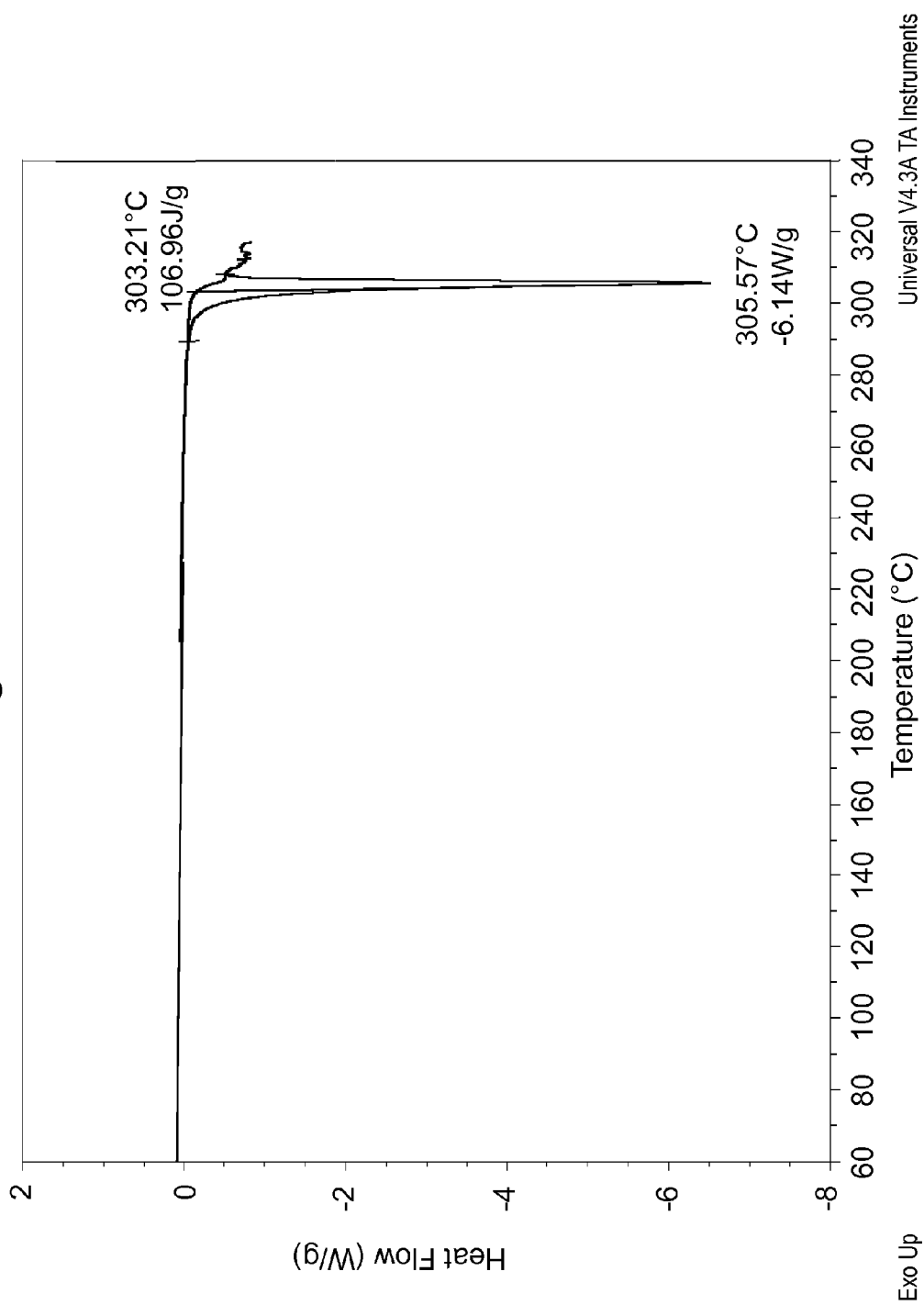
FIG. 25 shows a DSC thermogram of a 1R:1S-camsylate salt.
Figure 26:
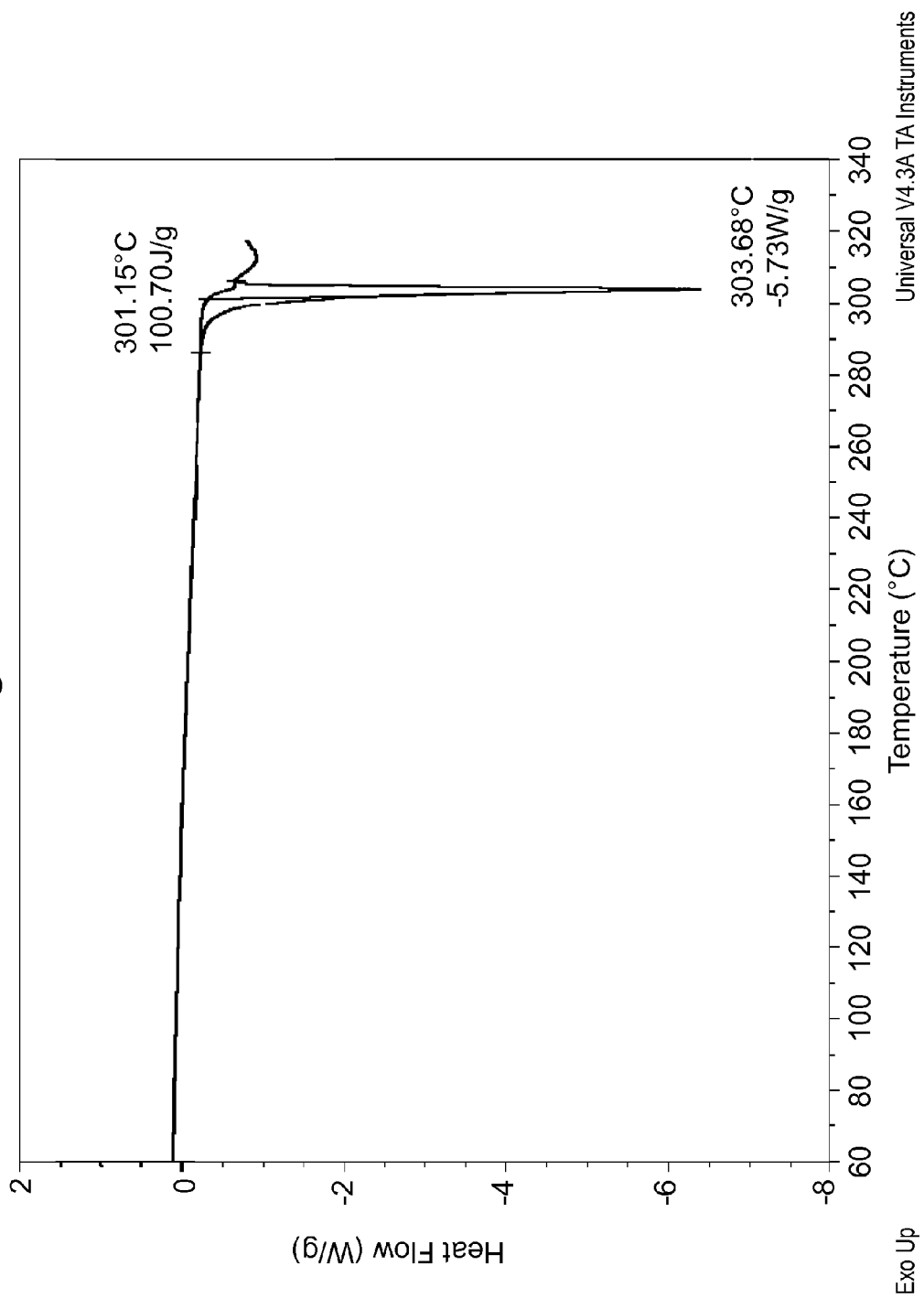
FIG. 26 shows a DSC thermogram of a 1R:9S-camsylate salt.

The DSC thermograms for the 1R:1S-camsylate salt and the 1R:9S-camsylate salt, shown in FIGS. 25 and 26, indicate an endotherm onset at 303.2° C. for the 1R:1S-camsylate salt and an endotherm onset at 301.2° C. for the 1R:9S-camsylate salt.

The 1R:1S-camsylate salt was also characterized by Fourier Transform-Infrared Spectroscopy (FT-IR) as described in Example 25, and the spectral peaks are shown in Table 25. Absorption band frequencies are listed. (w: weak, m: medium, s: strong, vs: very strong). Experimental error is ±2 cm$^{-1}$ except for * error on peak position could be considerably larger.

TABLE 25

| wavenumber (cm$^{-1}$) |
|---|
| 3293 w |
| 3078 w |
| 2966 w |
| 2915 w |
| 1754 w |
| 1743 s |
| 1635 m |
| 1615 s |
| 1582 w |
| 1513 w |
| 1475 m |
| 1463 m |
| 1446 s |
| 1416 m |
| 1366 w |
| 1347 m |
| 1324 m |
| 1315 m |
| 1266 m |
| 1254 m |
| 1241 s |
| 1216 m |
| 1194 m |
| 1180 m |
| 1156 s |
| 1132 s |
| 1125 s |
| 1106 s |
| 1066 m |
| 1056 m |
| 1028 s |
| 982 w |
| 964 w |
| 959 w |
| 950 w |

TABLE 25-continued

| wavenumber (cm$^{-1}$) |
| --- |
| 937 w |
| 899 w |
| 869 s |
| 856 m |
| 843 m |
| 810 m |
| 788 s |
| 754 m |
| 742 w |
| 721 m |
| 705 m |
| 674 m |
| 657 m |

The 1R:1S-camsylate salt was also characterized by Fourier Transform-Raman Spectroscopy (FT-Raman) as described in Example 26, and the spectral peaks are shown in Table 26. (w: weak, m: medium, s: strong, vs: very strong). Experimental error is ±2 cm$^{-1}$.

TABLE 26

| Wavenumber (cm$^{-1}$) |
| --- |
| 3298 w* |
| 3228 w |
| 3074 w |
| 3059 w |
| 3026 w |
| 2986 w |
| 2965 w |
| 2943 w |
| 2917 w |
| 2895 w |
| 2845 w |
| 2818 w |
| 2777 w |
| 2718 w |
| 2553 w |
| 1744 w |
| 1616 vs |
| 1583 s |
| 1578 s |
| 1554 vs |
| 1511 w |
| 1454 vs |
| 1434 m |
| 1419 w |
| 1407 w |
| 1368 m |
| 1348 s |
| 1324 m |
| 1269 w |
| 1251 w |
| 1218 w |
| 1204 m |
| 1164 w |
| 1135 w |
| 1068 s |
| 1039 w |
| 1021 w |
| 1002 w |
| 960 w |
| 939 w |
| 901 w |
| 874 w |
| 859 w |
| 813 w |
| 795 w |
| 754 w |
| 725 w |
| 706 w |
| 678 w |
| 646 w |
| 616 w |

TABLE 26-continued

| Wavenumber (cm$^{-1}$) |
| --- |
| 581 w |
| 549 w |
| 515 w |
| 504 w |
| 485 w |
| 443 w |
| 430 w |
| 413 w |
| 400 w |
| 369 w |
| 350 w |
| 340 w |
| 277 w |
| 261 w |
| 242 w |
| 215 w |
| 161 w |
| 136 w |
| 116 m |
| 86 m |
| 63 m |

H. R-camsylate Salt of Compound 1, R-camsylate Polymorph Form A

The R-camsylate salt of Compound 1, R-camsylate polymorph Form A, can be produced as described in Example 21.

Figure 23:
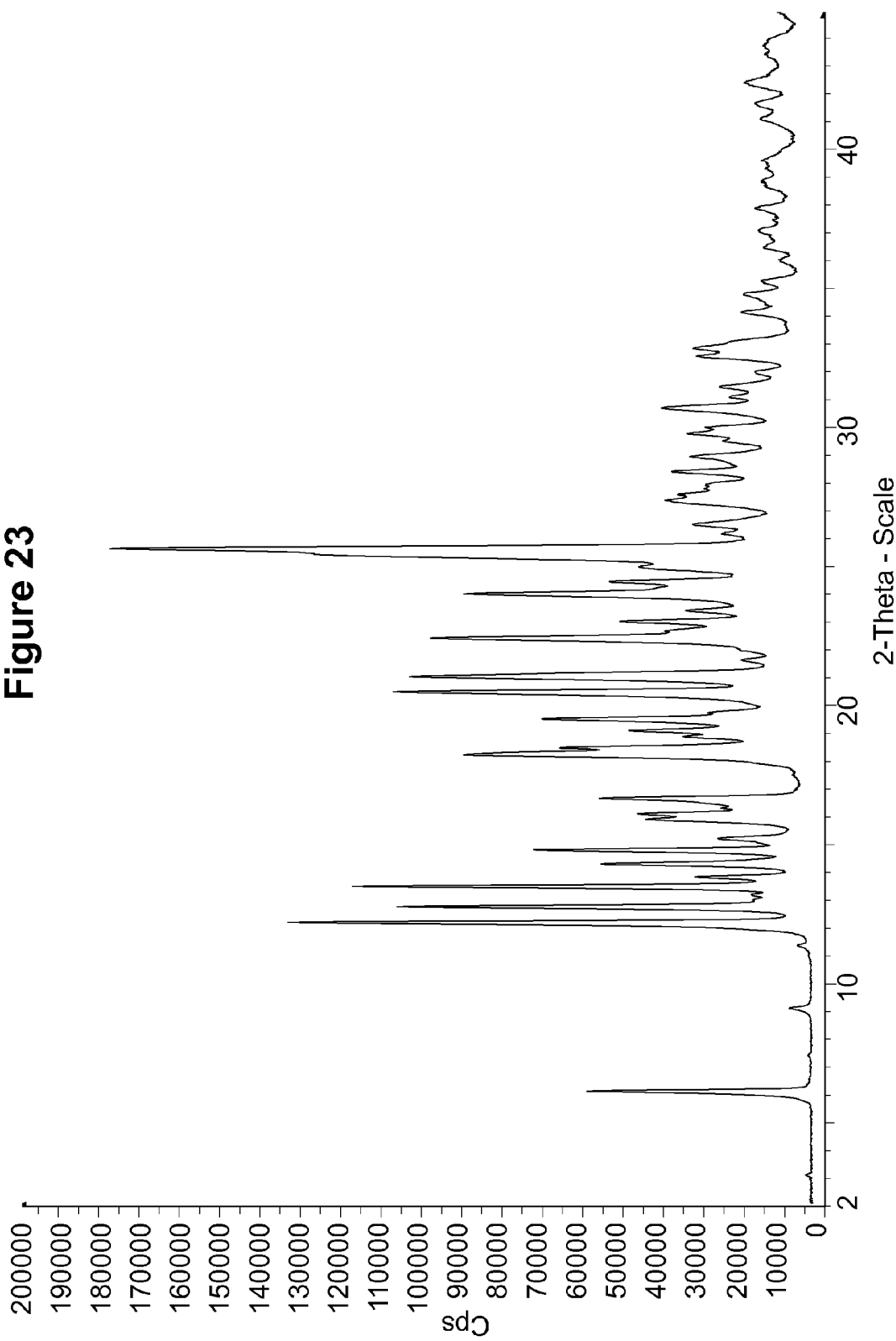
FIG. 23 shows an experimental PXRD pattern of an R-camsylate salt of Compound 1, polymorph Form A, using CuKα radiation at 1.5406 Å.

R-camsylate polymorph Form A was characterized by measuring the PXRD pattern for a particular batch of R-camsylate polymorph Form A. This experimental PXRD pattern is shown in FIG. 23. The experimental PXRD pattern of R-camsylate polymorph Form A, expressed in terms of the degree (2θ) and relative intensities with a relative intensity greater than 10.0%, measured on a Bruker-AXS Ltd., D4 diffractometer with CuKα radiation at 1.5406 Å, is also shown in Table 27.

TABLE 27

| Angle (Degree 2θ ± 0.1°) | Relative Intensity (>10.0%) |
| --- | --- |
| 6.1 | 33.2 |
| 12.2 | 76.9 |
| 12.7 | 60.6 |
| 13.5 | 67.0 |
| 13.8 | 16.0 |
| 14.3 | 29.9 |
| 14.8 | 39.8 |
| 15.2 | 12.3 |
| 15.9 | 22.9 |
| 16.1 | 24.1 |
| 16.6 | 29.7 |
| 18.2 | 49.3 |
| 18.5 | 34.9 |
| 19.1 | 24.4 |
| 19.5 | 37.2 |
| 20.5 | 58.9 |
| 21.0 | 56.3 |
| 22.4 | 52.9 |
| 23.0 | 24.6 |
| 23.4 | 14.8 |
| 24.0 | 47.7 |
| 24.5 | 25.9 |
| 25.0 | 21.6 |
| 25.6 | 100.0 |
| 26.5 | 13.5 |
| 27.4 | 17.5 |
| 28.4 | 16.6 |
| 29.0 | 14.0 |
| 29.8 | 14.4 |
| 30.7 | 18.5 |
| 31.5 | 10.1 |
| 32.9 | 14.3 |

Figure 27:
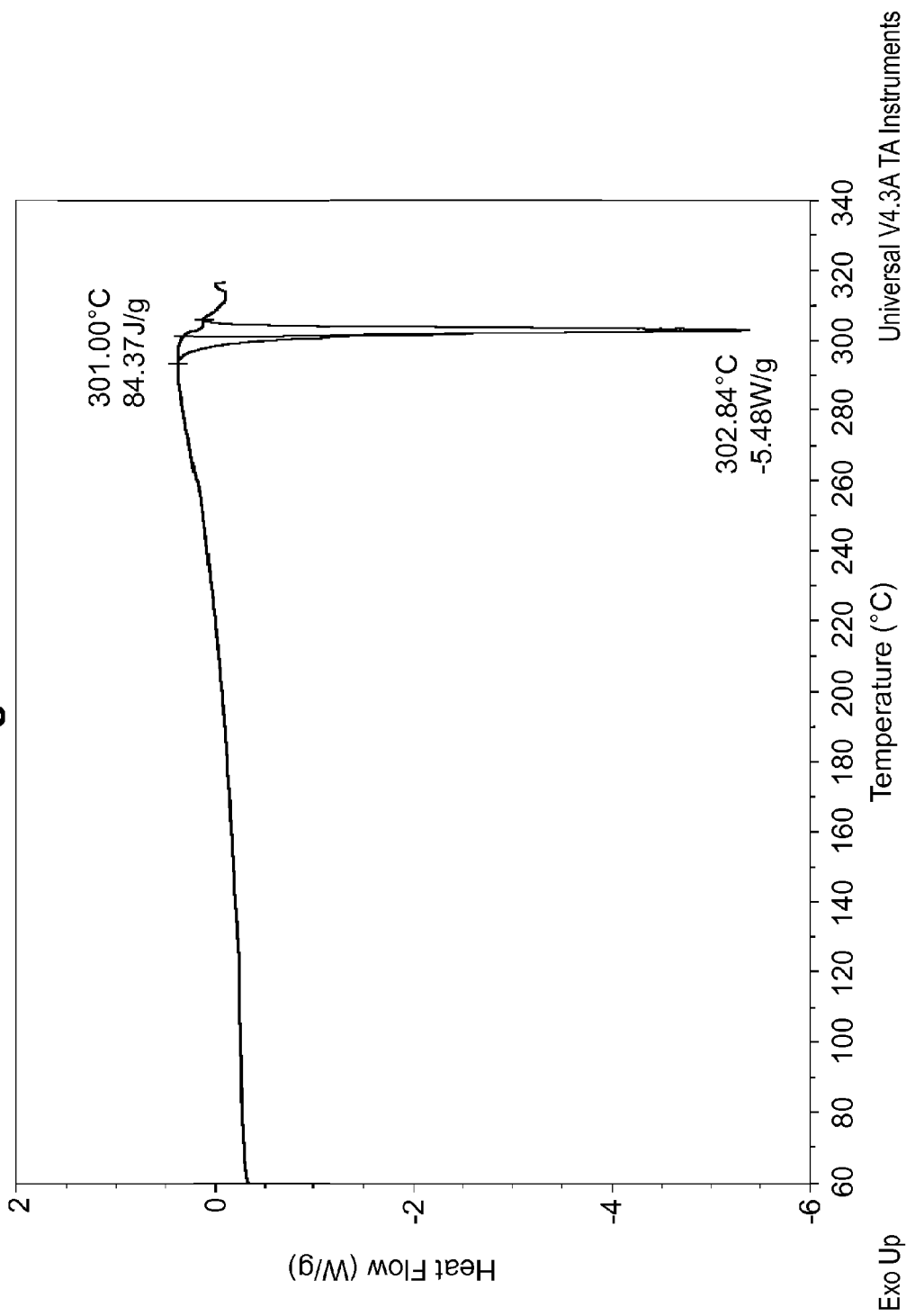
FIG. 27 shows a DSC thermogram of an R-camsylate salt of Compound 1, polymorph Form A.

The DSC thermogram for R-camsylate polymorph Form A, shown in FIG. 27, indicates an endotherm onset at 301.0° C.

R-camsylate polymorph Form A was also characterized by Fourier Transform-Infrared Spectroscopy (FT-IR) as described in Example 25, and the spectral peaks are shown in Table 28. Absorption band frequencies are listed. (w: weak, m: medium, s: strong, vs: very strong). Experimental error is ±2 cm$^{-1}$ except for * error on peak position could be considerably larger.

TABLE 28

| wavenumber (cm$^{-1}$) |
|---|
| 3288 m |
| 3238 m |
| 3076 w |
| 2966 w |
| 2949 w |
| 2916 w |
| 2892 w |
| 2840 w |
| 1743 s |
| 1637 s |
| 1615 s |
| 1581 w |
| 1510 w |
| 1474 m |
| 1451 m |
| 1416 m |
| 1366 w |
| 1348 w |
| 1315 m |
| 1290 w |
| 1266 m |
| 1255 m |
| 1240 s |
| 1234 s |
| 1203 s |
| 1193 s |
| 1152 s |
| 1129 s |
| 1104 s |
| 1066 m |
| 1056 w |
| 1029 s |
| 979 w |
| 967 w |
| 958 w |
| 951 w |
| 937 w |
| 899 w |
| 870 m |
| 864 m |
| 848 m |
| 835 m |
| 811 m |
| 787 s |
| 754 m |
| 720 m |
| 707 m |
| 674 m |
| 660 m |

R-camsylate polymorph Form A was also characterized by Fourier Transform-Raman Spectroscopy (FT-Raman) as described in Example 26, and the spectral peaks are shown in Table 29. (w: weak, m: medium, s: strong, vs: very strong). Experimental error is ±2 cm$^{-1}$.

TABLE 29

| wavenumber (cm$^{-1}$) |
|---|
| 3296 w |
| 3231 w |

TABLE 29-continued

| wavenumber (cm$^{-1}$) |
|---|
| 3109 w |
| 3075 w |
| 3059 w |
| 3042 w |
| 3024 w |
| 2999 w |
| 2966 w |
| 2942 w |
| 2921 w |
| 2895 w |
| 2845 w |
| 2820 w |
| 2777 w |
| 2718 w |
| 2555 w |
| 1745 w |
| 1617 vs |
| 1581 s |
| 1554 vs |
| 1510 w |
| 1454 vs |
| 1434 w |
| 1419 w |
| 1408 w |
| 1369 m |
| 1348 m |
| 1324 m |
| 1270 w |
| 1251 w |
| 1214 w |
| 1201 w |
| 1160 w |
| 1134 w |
| 1068 s |
| 1041 w |
| 1022 w |
| 939 w |
| 901 w |
| 859 w |
| 816 w |
| 726 w |
| 708 w |
| 679 w |
| 645 w |
| 621 w |
| 585 w |
| 549 w |
| 516 w |
| 503 w |
| 484 w |
| 430 w |
| 415 w |
| 370 w |
| 350 w |
| 277 w |
| 261 w |
| 243 w |
| 219 w |
| 158 w |
| 137 w |
| 115 m |
| 84 m |
| 64 m |

R-camsylate polymorph Forms B and C can also be produced and characterized according to the methods described above.

II. Amorphous Form of the S-Camsylate Salt of Compound 1

The amorphous form of the S-camsylate salt of Compound 1, can be produced as described in Example 27.

Figure 34:
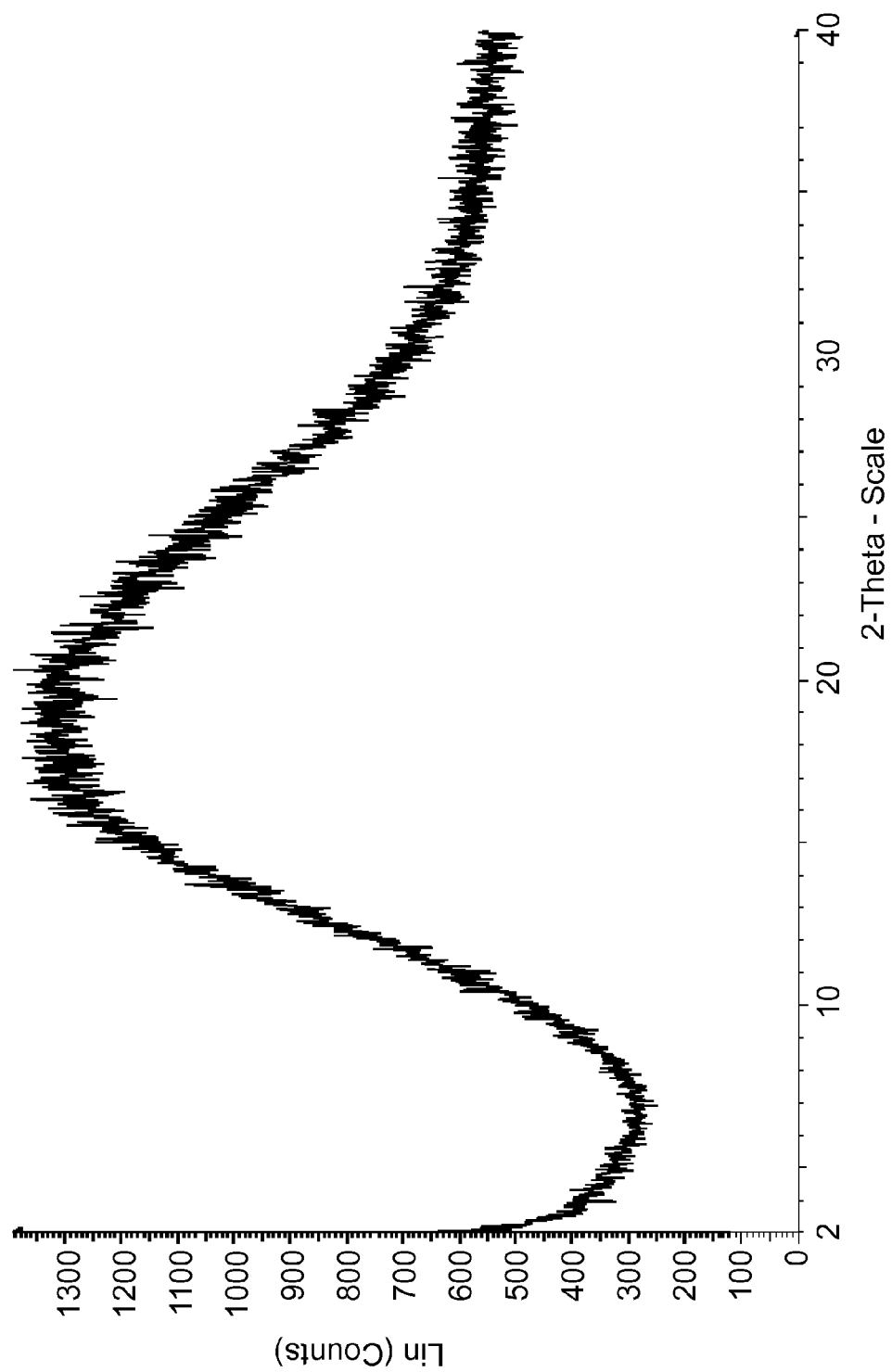
FIG. 34 shows an experimental PXRD pattern of an amorphous form of the S-camsylate salt of Compound 1.

The amorphous form of the S-camsylate salt of Compound 1 was characterized by measuring the PXRD pattern for a particular batch of the amorphous form of the S-camsylate salt of Compound 1, as described in Example 28. This experimental PXRD pattern is shown in FIG. 34.

Figure 35:
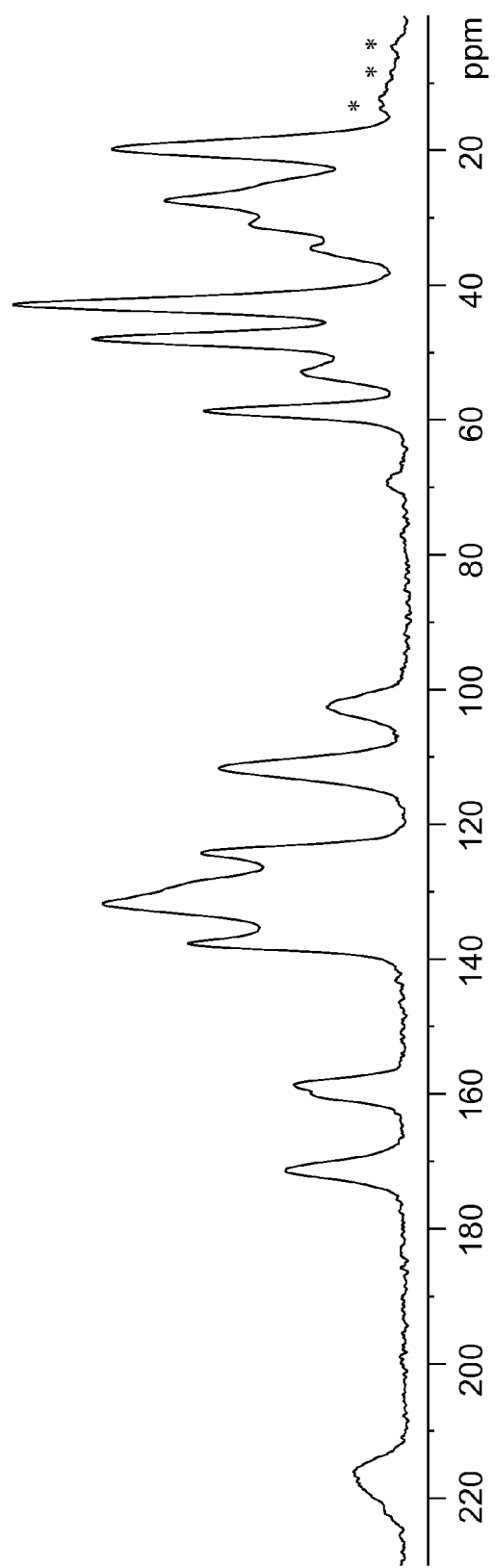
FIG. 35 shows a $^{13}$C solid state NMR spectrum of an amorphous form of the S-camsylate salt of Compound 1.

The amorphous form of the S-camsylate salt of Compound 1 was also characterized by the solid state NMR spectral pattern shown in FIG. 35, carried out on a Bruker-Biospin 4 mm BL CPMAS probe positioned into a wide-bore Bruker-Biospin DSX 500 MHz NMR spectrometer as described in Example 29. The $^{13}$C chemical shifts of the amorphous form of the S-camsylate salt of Compound 1 are shown in Table 30.

TABLE 30

| $^{13}$C Chemical Shifts[a] [ppm] | Intensity[b] |
| --- | --- |
| 216.1 | 1.5 |
| 171.5 | 3.6 |
| 160.2[c] | 2.8 |
| 158.6 | 3.4 |
| 137.7 | 6.6 |
| 131.8 | 9.2 |
| 129.5[c] | 7.3 |
| 124.3 | 6.2 |
| 111.7 | 5.7 |
| 102.6 | 2.3 |
| 58.7 | 6.1 |
| 52.8 | 3.2 |
| 48.0 | 9.6 |
| 42.9 | 12.0 |
| 34.6 | 2.8 |
| 31.2 | 4.7 |
| 27.5 | 7.3 |
| 19.8 | 9.0 |

[a]Referenced to external sample of solid phase adamantane at 29.5 ppm.
[b]Defined as peak heights. Intensities can vary depending on the actual setup of the CPMAS experimental parameters and the thermal history of the sample. CPMAS intensities are not necessarily quantitative.
[c]Peak shoulder.

Figure 36:
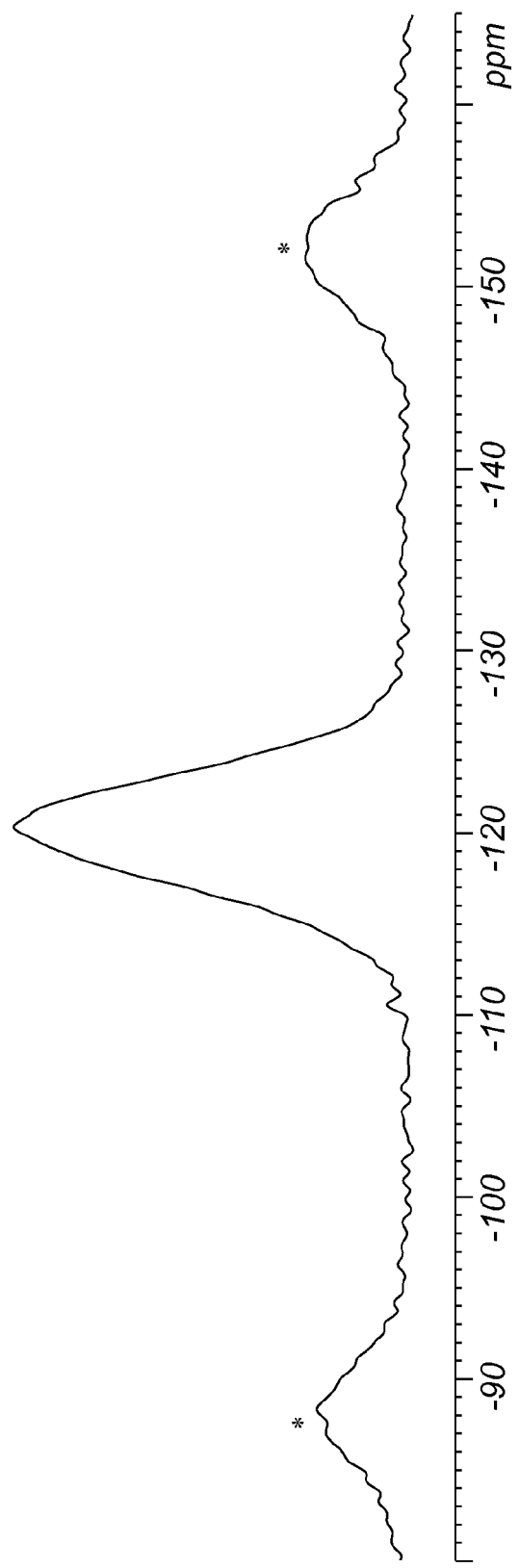
FIG. 36 shows a $^{19}$F solid state NMR spectrum of an amorphous form of the S-camsylate salt of Compound 1.
Figure 37:
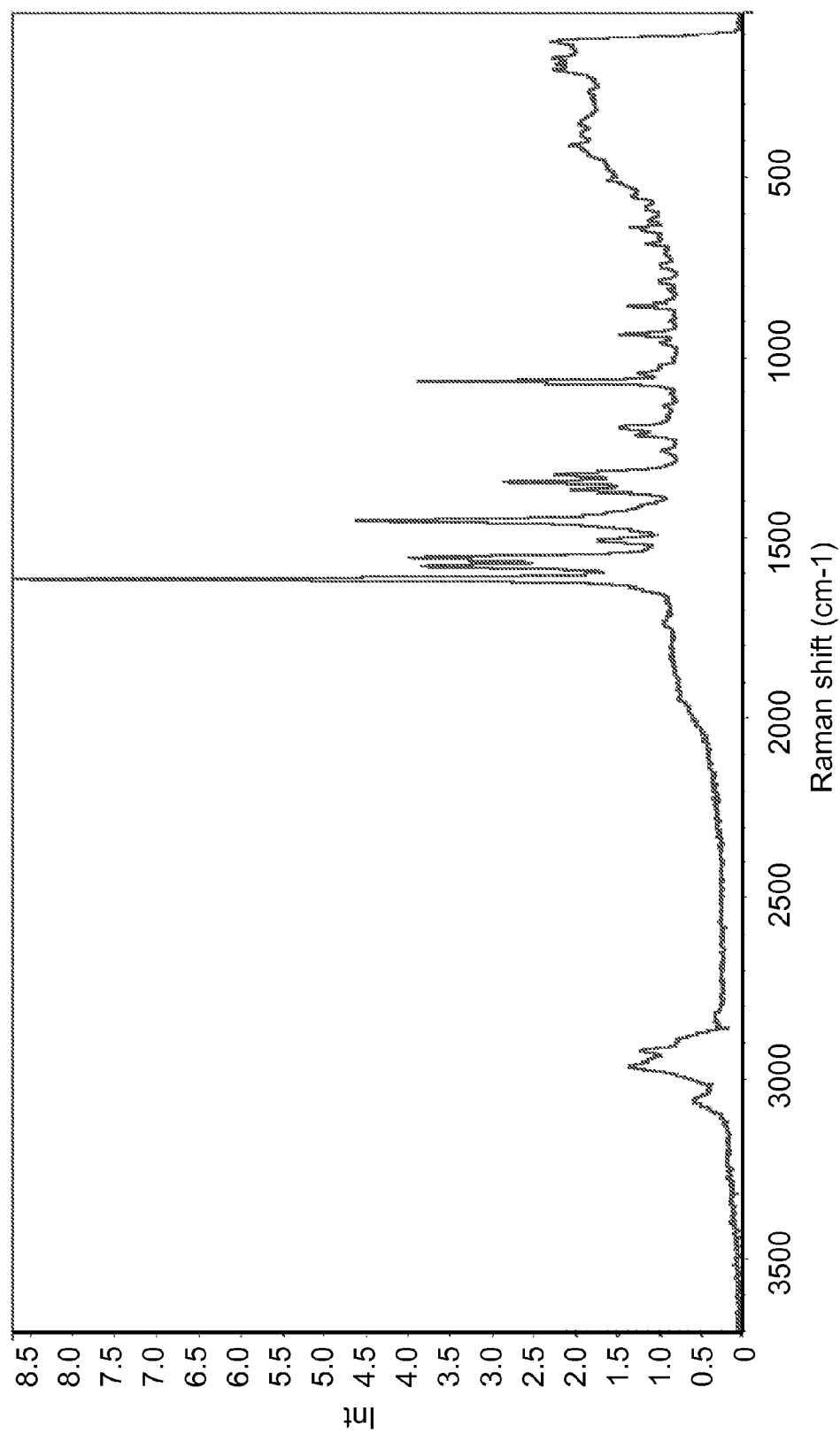
FIG. 37 shows a Raman spectrum of an amorphous form of the S-camsylate salt of Compound 1.

The amorphous form of the S-camsylate salt of Compound 1 was also characterized by the solid state NMR spectral pattern shown in FIG. 36, carried out on a Bruker-Biospin 4 mm BL CPMAS probe positioned into a wide-bore Bruker-Biospin DSX 500 MHz NMR spectrometer as described in Example 29. The $^{19}$F chemical shifts of the amorphous form of the S-camsylate salt of Compound 1 are shown in Table 31.

TABLE 31

| $^{19}$F Chemical Shifts[a] [ppm] | Intensity[b] |
| --- | --- |
| −120.3 | 12.0 |

[a]Referenced to external standard of trifluoroacetic acid (50% V/V in H$_2$O) at −76.54 ppm.
[b]Defined as peak heights.

Figure 38:
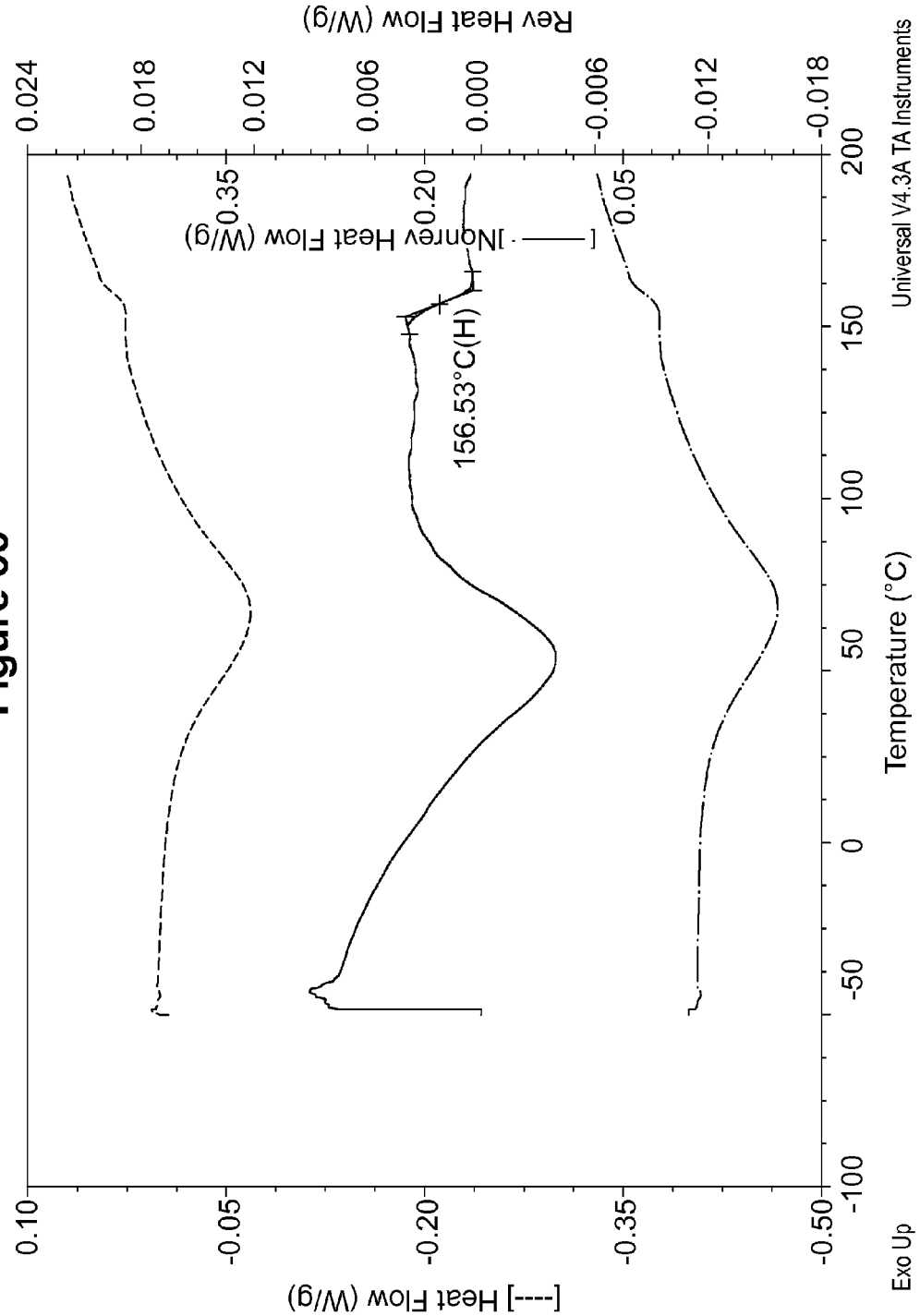
FIG. 38 shows a DSC thermogram of an amorphous form of the S-camsylate salt of Compound 1.

The DSC thermogram for the amorphous form of the S-camsylate salt of Compound 1, shown in FIG. 38, indicates a glass transition temperature (Tg) of 156.5° C.

III. Pharmaceutical Compositions of the Invention

The active agents (e.g., the crystalline salt forms or solid forms comprising two or more such forms, of Compound 1) described herein may be formulated into pharmaceutical compositions suitable for mammalian medical use. Any suitable route of administration may be employed for providing a patient with an effective dosage of any of the polymorphic forms of Compound 1. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of Compound 1. In all dosage forms, polymorphic forms of Compound 1 can be admixtured with other suitable constituents. The compositions may be conveniently presented in unit dosage forms, and prepared by any methods known in the pharmaceutical arts. Pharmaceutical compositions of the invention typically include a therapeutically effective amount of the active agent and one or more inert, pharmaceutically acceptable carriers, and optionally any other therapeutic ingredients, stabilizers, or the like. The carrier(s) are typically pharmaceutically acceptable in the sense of being compatible with the other ingredients of the formulation and not unduly deleterious to the recipient thereof. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in *Remington: The Science & Practice of Pharmacy*, 19$^{th}$ ed., Williams & Williams, (1995), and in the "Physician's Desk Reference", 52$^{nd}$ ed., Medical Economics, Montvale, N.J. (1998), and in *Handbook of Pharmaceutical Excipients*, 3$^{rd}$. Ed., Ed. A.H. Kibbe, Pharmaceutical Press, 2000. The active agents of the invention may be formulated in compositions including those suitable for oral, rectal, topical, nasal, ophthalmic, or parenteral (including intraperitoneal, intravenous, subcutaneous, or intramuscular injection) administration.

The amount of the active agent in the formulation can vary depending upon a variety of factors, including dosage form, the condition to be treated, target patient population, and other considerations, and will generally be readily determined by one skilled in the art. A therapeutically effective amount will typically be an amount necessary to modulate, regulate, or inhibit a PARP enzyme. In practice, this can vary widely depending, for example, upon the particular active agent, the severity of the condition to be treated, the patient population, the stability of the formulation, and the like. Compositions will generally contain anywhere from about 0.001% by weight to about 99% by weight active agent, preferably from about 0.01% to about 5% by weight active agent, and more preferably from about 0.01% to 2% by weight active agent, and can also depend upon the relative amounts of excipients/additives contained in the composition.

In some embodiments, a pharmaceutical composition can be administered in conventional dosage form prepared by combining a therapeutically effective amount of an active agent as an active ingredient with one or more appropriate pharmaceutical carriers according to conventional procedures. These procedures may involve mixing, granulating and compressing or dissolving the ingredients as appropriate to the desired preparation.

The pharmaceutical carrier(s) employed may be either solid or liquid. Exemplary solid carriers include, but are not limited to, lactose, sucrose, talc, gelatin, agar, pectin, acacia, magnesium stearate, stearic acid and the like. Exemplary liquid carriers include syrup, peanut oil, olive oil, water and the like. Similarly, the carrier(s) may include time-delay or time-release materials known in the art, such as glyceryl monostearate or glyceryl distearate alone or with a wax, ethylcellulose, hydroxypropylmethylcellulose, methylmethacrylate and the like.

A variety of pharmaceutical forms can be employed. For example, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an active agent can be dissolved in an aqueous solution of an organic or inorganic acid, such as 0.3 M solution of succinic acid or citric acid. If a soluble salt form is not available, the active agent may be dissolved in a suitable co-solvent or combinations of co-solvents. Examples of suitable co-solvents include, but are not limited to, alcohol, propylene glycol, polyethylene glycol 300, polysorbate 80, gylcerin and the like in concentrations ranging from about 0 to about 60% of the total volume. The composition may also be in the form of a solution of a salt form of the active agent in an appropriate aqueous vehicle such as water or isotonic saline or dextrose solution.

It will be appreciated that the actual dosages of Compound 1 used in the compositions of this invention can vary according to the particular polymorphic form being used, the particular composition formulated, the mode of administration and the particular site, host and disease being treated. Those skilled in the art using conventional dosage-determination tests in view of the experimental data for an agent can ascertain optimal dosages for a given set of conditions. For oral administration, an exemplary daily dose generally employed is from about 0.001 to about 1000 mg/kg of body weight, more preferably from about 0.001 to about 50 mg/kg body weight, and courses of treatment can be repeated at appropriate intervals. Administration of prodrugs is typically dosed at weight levels that are chemically equivalent to the weight levels of the fully active form. In the practice of the invention, the most suitable route of administration as well as the magnitude of a therapeutic dose will depend on the nature and severity of the disease to be treated. The dose, and dose frequency, may also vary according to the age, body weight, and response of the individual patient. In general, a suitable oral dosage form may cover a dose range from 0.5 mg to 100 mg of active ingredient total daily dose, administered in one single dose or equally divided doses. A preferred amount of Compound 1 in such formulations is from about 0.5 mg to about 20 mg, such as from about 1 mg to about 10 mg or from about 1 mg to about 5 mg.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

For oral administration, a polymorphic form of Compound 1 can be formulated readily by combining the active agent with pharmaceutically acceptable carriers known in the art. Such carriers enable the compounds of the invention to be formulated as tablets, pills, dragees, capsules, gels, syrups, slurries, suspensions and the like, for oral ingestion by a patient to be treated. Pharmaceutical preparations for oral use can be obtained using a solid excipient in admixture with the active agent, optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The active agents may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include, for example, suspensions of the active agents and may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active agents to allow for the preparation of highly concentrated solutions.

For administration to the eye, the active agent can be delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be, for example, an ointment, vegetable oil, or an encapsulating material. An active agent of the invention may also be injected directly into the vitreous and aqueous humor or subtenon.

Alternatively, the active ingredient may be in powder form for constitution with a suitable vehicle, e.g., sterile pyrogen-free water, before use. The compounds may also be formulated in rectal or vaginal compositions such as suppositories or retention enemas, e.g., containing conventional suppository bases such as cocoa butter or other glycerides.

In addition to the formulations described above, the polymorphic forms may also be formulated as a depot preparation. Such long-acting formulations may be administered by implantation (for example, subcutaneously or intramuscularly) or by intramuscular injection. Thus, for example, the polymorphic forms may be formulated with suitable polymeric or hydrophobic materials (for example, as an emulsion in an acceptable oil) or ion-exchange resins, or as sparingly soluble derivatives, for example, as a sparingly soluble salt.

Additionally, polymorphic forms of Compound 1 may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compound for a few weeks up to over 100 days.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

IV. Methods of Using the Polymorphs of the Invention

Polymorphic forms of the crystalline salts of Compound 1 can be useful for mediating the activity of poly(ADP-ribose) polymerase (PARP). More particularly, these polymorphic forms can be useful as chemosensitizers that enhance the efficacy of radiotherapy or cytotoxic drugs whose mechanism depends on DNA damage. These drugs include, but are not limited to, temozolomide (SCHERING), irinotecan (PFIZER), topotecan (GLAXO SMITHKLINE), cisplatin (BRISTOL MEYERS SQUIBB; AM PHARM PARTNERS; BEDFORD; GENSIA SICOR PHARMS; PHARMACHEMIE), and doxorubicin hydrochloride (AM PHARM PARTNERS; BEDFORD; GENSIA; SICOR PHARMS; PHARMACHEMIE; ADRIA; ALZA).

Polymorphic salt forms of Compound 1 can also be useful for enhancing the induction of the expression of Reg gene in β cells and HGF gene and, accordingly, promoting the proliferation of pancreatic β-cells of Langerhans' islets and suppressing apoptosis of the cells. Further, the inventive polymorphic salt forms of Compound 1 can be useful for preparing cosmetics, for example, in after-sun lotions.

Therapeutically effective amounts of the agents of the invention may be administered, typically in the form of a pharmaceutical composition, to treat diseases mediated by modulation or regulation of PARP. An "effective amount" refers to that amount of an agent that, when administered to a mammal, including a human, in need of such treatment, is sufficient to effect treatment for a disease mediated by the activity of one or more PARP enzyme. Thus, a therapeutically effective amount of a compound refers to a quantity sufficient to modulate, regulate, or inhibit the activity of one or more PARP enzyme such that a disease condition that is mediated by that activity is reduced or alleviated. The effective amount of a given compound can vary depending upon factors such as the disease condition and its severity and the identity and condition (e.g., weight) of the mammal in need of treatment, but can nevertheless be routinely determined by one skilled in the art. "Treating" refers to at least the mitigation of a disease condition in a mammal, including a human, that is affected, at least in part, by the activity of one or more PARP enzymes and includes: preventing the disease condition from occurring in a mammal, particularly when the mammal is found to be predisposed to having the disease condition but has not yet been diagnosed as having it; modulating and/or inhibiting the disease condition; and/or alleviating the disease condition. Exemplary disease conditions include diabetic retinopathy, neovascular glaucoma, rheumatoid arthritis, psoriasis, age-related macular degeneration (AMD), and abnormal cell growth, such as cancer. Cancer includes, but is not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

Abnormal cell growth also includes, but is not limited to, benign proliferative diseases, including, but not limited to, psoriasis, benign prostatic hypertrophy or restinosis.

The activity of the polymorphic salt forms of Compound 1 as modulators of PARP activity may be measured by any of the methods available to those skilled in the art, including in vivo and/or in vitro assays. Examples of suitable assays for activity measurements include those described in U.S. Pat. No. 6,495,541 and U.S. Provisional Patent Application No. 60/612,458, the disclosures of which are incorporated herein by reference in their entireties.

Some embodiments are also directed to therapeutic methods of treating a disease condition mediated by PARP activity, for example, cancer and a variety of disease and toxic states that involve oxidative or nitric oxide induced stress and subsequent PARP hyperactivation. Such conditions include, but are not limited to, neurologic and neurodegenerative disorders (eg, Parkinson's disease, Alzheimer's disease), cardiovascular disorders (e.g., myocardial infarction, ischemia-reperfusion injury), diabetic vascular dysfunction, cisplatin-induced nephrotoxicity. In some embodiments, the therapeutic methods include administering to a mammal in need thereof a therapeutically effective amount of a pharmaceutical composition which includes any of the polymorphic forms, or pharmaceutical compositions discussed herein.

Some embodiments are also directed to combination therapeutic methods of treating a disease condition mediated by PARP activity, which comprises administering to a mammal in need thereof a therapeutically effective amount of a pharmaceutical composition which comprises any of the polymorphic forms, or pharmaceutical compositions discussed herein, in combination with a therapeutically effective amount of one or more substances, such as anti-tumor agents, anti-angiogenesis agents, signal transduction inhibitors, and antiproliferative agents, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Such substances include, but are not limited to, those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include temozolomide (SCHERING), irinotecan (PFIZER), topotecan (GLAXO SMITHKLINE), cisplatin (BRISTOL MEYERS SQUIBB; AM PHARM PARTNERS; BEDFORD; GENSIA SICOR PHARMS; PHARMACHEMIE), and doxorubicin hydrochloride (AM PHARM PARTNERS; BEDFORD; GENSIA; SICOR PHARMS; PHARMACHEMIE; ADRIA; ALZA).

Additional examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example, carboplatin, oxiplatin, iproplatin, ethyl ester of N-acetyl-DL-sarcosyl-L-leucine (Asaley or Asalex), 1,4-cyclohexadiene-1,4-dicarbamic acid, 2,5-bis (1-azirdinyl)-3,6-dioxo-, diethyl ester (diaziquone), 1,4-bis (methanesulfonyloxy)butane (bisulfan or leucosulfan), chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea, 1-(2-chloroethyl)-3-(2,6-dioxo-3-piperidyl)-1-nitroso-urea, bis (2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, and strptozoin. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)methyl]amino]benzoyl]R-aspartic acid, N-[4-[[(2,4-diamino-5-ethyl-6-quinazolinyl)methyl]amino]benzoylFL-aspartic acid, N-[2-chloro-4-[[(2,4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/1B98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoylcyclobutyl)-amino]-propionic acid; 4-[4-(4-chloro-phenoxy)-benzenesulfonylaminoFtetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors include, for example, those described in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. Examples of VEGF inhibitors are described in, for example in WO 99/24440 (published May 20, 1999), PCT International Application PCT/1B99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include, but are not limited to, those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include, but are not limited to, inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998), which is herein incorporated by reference in its entirety.

The disclosures of all cited references are incorporated herein by reference in their entirety.

EXAMPLES

The examples which follow will further illustrate the preparation and characterization of the distinct polymorphic salt forms of Compound 1, but are not intended to limit the scope of the invention as described herein or as claimed herein. Unless otherwise indicated, all temperatures are set forth in degrees Celsius and all parts and percentages are by weight.

Example 1

Preparation of a Maleate Salt of Compound 1, Maleate Polymorph Form A

A solution of Compound 1 (100.8 mg; 0.31 mmol) in 80/20 v/v isopropyl alcohol/water (25 mL) was prepared by dissolving the solid in the liquid medium with stirring at ambient conditions (20-25° C.). A solution of maleic acid (25.13 mg; 0.22 mmol) in a minimum volume of 80/20 v/v isopropyl alcohol/water was prepared as above. 17.26 mL of the solution of Compound 1 was added slowly to the maleic acid solution with stirring at ambient conditions to provide an equimolar solution of Compound 1 and maleic acid. The resulting solution was allowed to stir for 24 hours at ambient conditions, followed by the addition of hexane (6 mL) and storage at −20° C. for 24 hours; crystallization occurred during that time. Following filtration and washing with 80/20 v/v isopropyl alcohol/water, the product was dried under vacuum at 40° C. which provided approximately 100 mg of crystalline material.

Example 2

Preparation of a Maleate Salt of Compound 1, Maleate Polymorph Form B, Using Ethanol A solution of Compound 1 (10 g; 30.9 mmol) in ethanol (450 mL) was prepared by heating to reflux in a jacketed reaction vessel with overhead stirring. A solution of maleic acid (3.95 g, 1.1 eq) in ethanol (20 mL) was added dropwise over 1 hour at 80° C.; crystallization occurred during this time. The suspension was cooled at 0.5° C./min and isolated at 0° C. after 1 hour granulation. Following filtration and washing with ethanol (50 mL), the product was dried under vacuum at 50° C. to furnish 12 g of the crystalline product (89% theoretical yield).

Example 3

Preparation of a Maleate Salt of Compound 1, Maleate Polymorph Form B, Using Isopropyl Alcohol A solution of Compound 1 (18 g; 55.7 mmol) in isopropyl alcohol (1500 mL) was prepared by heating in a jacketed reaction vessel with overhead stirring. A solution of maleic acid (7.11 g, 1.1 eq) in isopropyl alcohol (100 mL) was prepared and was added dropwise (over 1 hour) following the addition of seed crystals of the title compound (45 mg). Once the addition was complete, the suspension was cooled to 0° C. (at natural rate) and granulated for 2 days. Following filtration the product was dried under vacuum at 50° C. to furnish 23.7 g of a crystalline product (97% theoretical yield).

Example 4

Preparation of an S-camsylate Salt of Compound 1, S-camsylate Polymorph Form A, Using Tetrahydrofuran Compound 1 (20 g) was slurried at reflux in tetrahydrofuran (42 mL) and water (40 mL) in a jacketed reaction vessel with overhead stirring, and remained as a free base slurry. S-camphor sulfonic acid solution (17.25 g in 20 mL of water) was added slowly over approximately 10 minutes, to form a clear yellow solution, which was held at reflux for 30 minutes. Water (135 mL) was then added, over approximately 20 minutes, maintaining reflux. The resulting yellowish slurry was cooled to 10° C. and granulated at this temperature to improve crystallinity and yield for a suitable amount of time. Suitable granulation times can be chosen by one of skill in the art. Typical granulation times can range, for example, from about 1 hour to about 48 hours. Filtered solids were washed with chilled water (20 mL) and dried under vacuum at 50° C. to give the final product.

Example 5

Preparation of an S-camsylate Salt of Compound 1, S-camsylate Polymorph Form A, Using Isopropyl Alcohol A solution of Compound 1 (982.5 mg; 3.03 mmol) in isopropyl alcohol (225 mL) was prepared by dissolving the solid in the liquid medium with stirring at ambient conditions (20-25° C.). A solution of S-camphor sulfonic acid (53.81 mg) in a minimum volume of isopropyl alcohol was prepared as above. 17.16 mL of the Compound 1 solution was added slowly to the maleic acid solution with stirring at ambient conditions to provide an equimolar solutions of Compound 1 and S-camphor sulfonic acid. The solution was allowed to stir for 48 hours at ambient conditions; crystallization occurred during that time. Following filtration and washing with isopropyl alcohol, the product was dried under vacuum at 40° C. which provided approximately 75 mg of crystalline material.

Example 6

Characterization of the S-camsylate Salt of Compound 1, Polymorph Form A and the Maleate Salt of Compound 1, Polymorph Form B by Powder X-ray Diffraction (PXRD)

The powder X-ray diffraction patterns, as shown in FIGS. 3, 4, 9, and 10, were determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The specimen was rotated while being irradiated with copper K-alpha$_1$ X-rays (wavelength=1.5406 Å) with the X-ray tube operated at 40 kV/35 mA. The analyses were performed with the goniometer running in continuous mode set for a 0.2 second count per 0.018° step over a two theta range of 2° to 55°. Peaks were aligned against those of the calculated simulated powder pattern.

Example 7

Characterization of the Maleate Salt of Compound 1, Polymorph Form A by Powder X-Ray Diffraction (PXRD)

The powder X-ray diffraction (PXRD) pattern measurement, as shown in FIG. 1, was carried out on a Bruker D5000 diffractometer using copper radiation (CuKα, wavelength: 1.54056 Å). The tube voltage and amperage were set to 40 kV and 40 mA, respectively. The divergence and scattering slits were set at 1 mm, and the receiving slit was set at 0.6 mm. Diffracted radiation was detected by a Kevex PSI detector. A theta-two theta continuous scan at 2.4 degrees/min (1 second/0.04 degree step) from 3.0 to 40 degrees 2θ was used. An alumina standard was analyzed to check the instrument alignment. Samples were prepared by placing them in a quartz holder.

Example 8

Characterization of the S-camsylate Salt of Compound 1, Polymorph Form B by Powder X-ray Diffraction (PXRD)

The powder X-ray diffraction pattern, as shown in FIG. 15, was obtained using a Bruker AXS Ltd. D8 Advance powder X-ray diffractometer fitted with Gobel mirror optics, a single sample heating stage and a position sensitive detector (PSD). Each specimen was irradiated with copper K-alpha$_1$ X-rays (wavelength=1.5406 Å) with the X-ray tube operated at 40 kV/40 mA. Analysis was performed with the goniometer running in continuous scan mode set for a 0.2 second count per 0.014° step over a range of 3° to 35° 2θ. Measurement was performed at 150° C. with the temperature controlled using an Ansyco sycos-H-HOT temperature controller.

Example 9

Characterization of the Maleate Salt of Compound 1, Polymorph Form B by Solid State Nuclear Magnetic Resonance (SSNMR)

Spectra were collected at ambient temperature and pressure on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The $^{13}$C solid state spectrum, as shown in FIG. 5, was collected using a proton decoupled cross-polarization magic angle spinning (CP-MAS). The cross-polarization contact time was set to 2.0 ms. A proton decoupling field of approximately 85 kHz was applied. 4096 scans were collected with a 14 second recycle delay. The carbon spectrum was referenced using an external standard of crystalline adamantane, setting its upfield resonance to 29.5 ppm. The $^{19}$F solid state spectrum, as shown in FIG. 6, was collected using a proton decoupled magic angle spinning experiment (MAS). A proton decoupling field of approximately 85 kHz was applied. 128 scans were collected with recycle delay of 140 seconds. The fluorine spectrum was referenced using an external standard of trifluoroacetic acid (50% V/V in $H_2O$), setting its resonance to −76.54 ppm.

Example 10

Characterization of the S-camsylate Salt of Compound 1, Polymorph Form A by Solid State Nuclear Magnetic Resonance (SSNMR)

Approximately 80 mg of sample were tightly packed into a 4 mm $ZrO_2$ rotor. Spectra were collected at ambient temperature and pressure on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The $^{13}$C solid state spectrum, as shown in FIG. 11, was collected using a proton decoupled cross-polarization magic angle spinning (CPMAS). The cross-polarization contact time was set to 2.0 ms. A proton decoupling field of approximately 85 kHz was applied. 2048 scans were collected with a 6 second recycle delay. The carbon spectrum was referenced using an external standard of crystalline adamantane, setting its upfield resonance to 29.5 ppm. The $^{19}$F solid state spectrum, as shown in FIG. 12, was collected using a proton decoupled magic angle spinning experiment (MAS). A proton decoupling field of approximately 85 kHz was applied. 256 scans were collected with recycle delay of 28 seconds. The fluorine spectrum was referenced using an external standard of trifluoroacetic acid (50% V/V in $H_2O$), setting its resonance to −76.54 ppm.

Example 11

Characterization of Polymorphs of Compound 1 by Differential Scanning Calorimetry (DSC)

Differential Scanning calorimetry of various polymorphs, as shown in FIGS. 2, 7, 13, and 24-27, was performed using a TA Instruments Q1000 or a Mettler Instruments DSC822. Samples (1 to 2 mg) were heated in a crimped aluminum pans from 20° C. at 10° C. per minute with a nitrogen gas purge, up to as much as about 320° C.

Example 12

Characterization of Polymorphs of Compound 1 by Dynamic Vapor Sorption (DVS)

Hygroscopicity, as shown in FIGS. 8 and 14, was measured using an Automated Sorption Analyser Model DVS-1, manufactured by Surface Measurements Systems Ltd. UK. Solid (20-25 mg) was exposed to a controlled relative humidity (% RH) and temperature environment (30° C.), and the weight change was recorded over time. The humidity was stepped from 0 to 90% RH in 15% RH intervals. A rate of sorption of 0.0005%/min averaged over 10 min was achieved at each humidity prior to exposure to the next humidity in the method.

Example 13

Preparation of a Solid Dosage Form of the S-camsylate Salt of Compound I, Polymorph Form A The S-camsylate salt polymorph Form A of Compound 1 was formulated into immediate release tablets. The formulated composition contained the following components:

| Component: | Quantity/unit: (%) |
| --- | --- |
| S-camsylate polymorph Form A Polymorph of Compound 1 | 17.18 |
| Microcrystalline cellulose | 52.55 |
| Dicalcium phosphate anhydrous | 26.27 |
| Sodium Starch Glycolate (Type A) | 3 |
| Magnesium Stearate | 1 |
| Total: | 100 |

Figure 16:
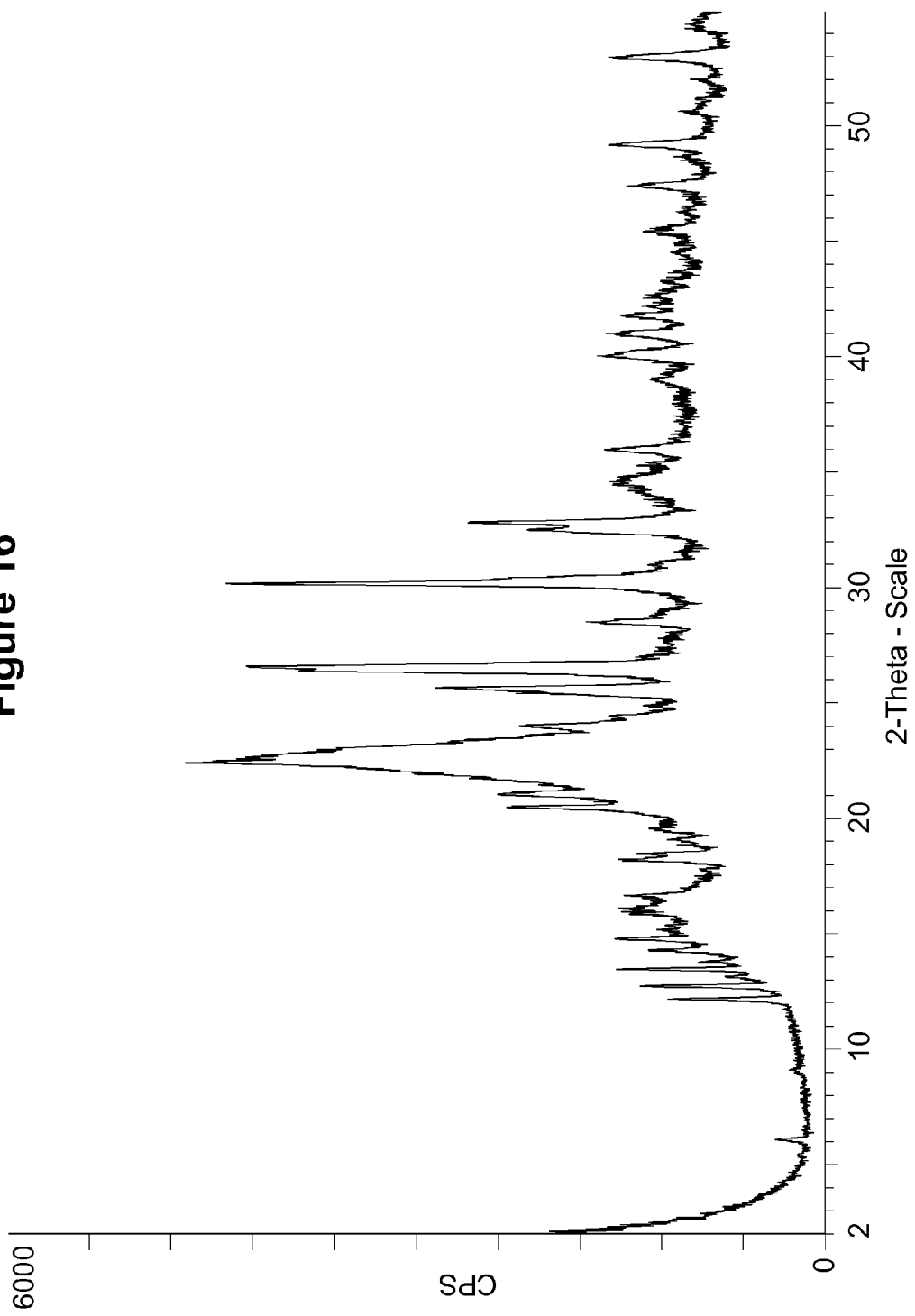
FIG. 16 shows an experimental PXRD pattern of a formulated composition containing the S-camsylate salt of Compound 1, polymorph Form A.

The formulated composition was characterized by the PXRD pattern shown in FIG. 16.

The same or similar formulation as above can be made using the maleate salt polymorphs, such that the same or a similar amount of free base drug concentration is maintained in the maleate salt formulation as in the formulation above.

Example 14

Physical Stability of Maleate Polymorph Form B

A PXRD pattern for maleate polymorph Form B was measured at: 1) an initial time point and 2): two weeks after storage at 70° C. with 75% relative humidity (RH). The PXRD pattern of maleate polymorph Form B did not change significantly after two weeks of storage at 70° C. with 75% relative humidity. This demonstrates that maleate polymorph Form B exists in a physically stable form.

Example 15

Physical Stability of S-Camsylate Polymorph Form A

A PXRD pattern for S-camsylate polymorph Form A was measured at: 1) an initial time point and 2): two weeks after storage at 70° C. with 75% relative humidity (RH). The PXRD pattern of S-camsylate polymorph Form A did not change significantly after two weeks of storage at 70° C. with 75% relative humidity. This demonstrates that S-camsylate polymorph Form A exists in a physically stable form.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

Example 16

Preparation of an S-Camsylate Salt of Compound 1, S-camsylate Polymorph Form C

A slurry of S-Camsylate polymorph Form A (1 g) was prepared in isopropyl alcohol:water (10 mL; 40:60% v/v). The slurry was heated to 70° C. over a 10 minute period to obtain a solution. The solution was cooled to 25° C. to obtain a supersaturated solution. Isopropyl alcohol:water (25 mL; 10:90% v/v) and water (30 mL) were added. The resultant supersaturated solution was transferred to a rotary evaporator and the solvent removed under vacuum (50 mbar) at 70° C. A precipitate was formed and isolated (0.6 g).

Example 17

Preparation of a 1R:1S-Camsylate Salt

A slurry of Compound 1 (1.5 g) was prepared in isopropyl alcohol:water (25 mL; 40:60% v/v). R-camphor sulfonic acid (0.65 g) and S-camphor sulfonic acid (0.65 g) were added, as a solution, in water (1.5 mL). The slurry was heated to 70° C. over a 10 minute period. The resultant solution was cooled to 0° C. over a 10 minute period. Solid crystallized after holding this solution at a temperature of 0° C. for one hour. This resulted in the formation of a slurry. This slurry was granulated for a total of 36 hours. The crystals were filtered and washed with water and then dried overnight at 50° C. providing a pale yellow powder (1.9 g).

Example 18

Preparation of a 1R:9S-Camsylate Salt

A slurry of Compound 1 (1.5 g) was prepared in isopropyl alcohol:water (25 mL; 40:60% v/v). R-camphor sulfonic acid (0.13 g) and S-camphor sulfonic acid (1.17 g) were added, as a solution, in water (1.5 mL). The slurry was heated to 70° C. over a 10 minute period. The resultant solution was cooled to 10° C. over a 10 minute period. Solid crystallized after holding this solution at a temperature of 10° C. for one hour. This resulted in the formation of a slurry. This slurry was granulated for a total of 48 hours. The crystals were filtered and washed with water and then dried overnight at 50° C. providing a pale yellow powder.

Example 19

Preparation of a 1R:3S-Camsylate Salt

A slurry of Compound 1 (1.5 g) was prepared in isopropyl alcohol:water (25 mL; 40:60% v/v). R-camphor sulfonic acid (0.325 g) and S-camphor sulfonic acid (0.975 g) were added, as a solution, in water (1.5 mL). The slurry was heated to 70° C. over a 10 minute period. The resultant solution was cooled to 10° C. over a 10 minute period. Solid crystallized after holding this solution at a temperature of 10° C. This resulted in the formation of a slurry. This slurry was granulated for a total of 4 hours. The crystals were filtered and washed with water and then dried overnight at 50° C. providing a pale yellow powder.

Example 20

Preparation of a 1R:7S-Camsylate Salt

A slurry of Compound 1 (1.5 g) was prepared in isopropyl alcohol:water (25 mL; 40:60% v/v). R-camphor sulfonic acid (0.16 g) and S-camphor sulfonic acid (1.14 g) were added, as a solution, in water (1.5 mL). The slurry was heated to 70° C. over a 10 minute period. The resultant solution was cooled to 10° C. over a 10 minute period. Solid crystallized after holding this solution at a temperature of 10° C. This resulted in the formation of a slurry. This slurry was granulated for a total of 4 hours. The crystals were filtered and washed with water and then dried overnight at 50° C. providing a pale yellow powder.

Example 21

Preparation of an R-Camsylate Salt of Compound 1, R-Camsylate Polymorph Form A

A slurry of Compound 1 (1.5 g) was prepared in isopropyl alcohol:water (25 mL; 40:60% v/v). R-camphor sulfonic acid (1.3 g) was added, as a solution, in water (1.5 mL). The slurry was heated to 70° C. over a 10 minute period. The resultant solution was cooled to 10° C. over a 10 minute period. Solid crystallized after holding this solution at a temperature of 10° C. This resulted in the formation of a slurry. This slurry was granulated for a total of 4 hours. The crystals were filtered and washed with water and then dried overnight at 50° C. providing a pale yellow powder.

Example 22

Characterization of the S-Camsylate Salt of Compound 1, Polymorph Form C, the 1R:1S-Camsylate Salt, the 1R:9S-Camsylate Salt, the 1R:3S-Camsylate Salt, the 1R:7S-Camsylate Salt, and the R-Camsylate Salt of Compound 1, R-Camsylate Polymorph Form A by Powder X-ray Diffraction (PXRD).

The powder X-ray diffraction patterns, as shown in FIGS. 18-23, were determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The specimen was rotated while being irradiated with copper K-alpha$_1$ X-rays (wavelength=1.5406 Ångstroms) with the X-ray tube operated at 40 kV/35 mA. The analyses were performed with the goniometer running in continuous mode set for a 0.2 second count per 0.018° step over a two theta range of 2° to 55°. Peaks were aligned against those of the calculated simulated powder pattern where available. Alternatively, the peaks were aligned using an internal reference material, such as silicon or corundum ($Al_2O_3$), mixed with the powder sample prior to analysis.

Example 23

Characterization of the S-camsylate Salt of Compound 1, Polymorph Form C, by Solid State Nuclear Magnetic Resonance (SSNMR)

Approximately 80 mg of each sample was tightly packed into a 4 mm $ZrO_2$ rotor. Spectra were collected at ambient conditions on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The $^{13}$C solid state spectrum, as shown in FIG. 28, was collected using a proton decoupled cross-polarization magic angle spinning (CPMAS) experiment. The cross-polarization contact time was set to 2.0 ms. A proton decoupling field of approximately 85 kHz was applied during acquisition. A minimum of 2048 scans were collected with a 7 second recycle delay. The carbon spectra were referenced using an external standard of crystalline adamantane, setting its upfield resonance to 29.5 ppm. The $^{19}$F solid state spectrum, as shown in FIG. 29, was collected using a proton decoupled magic angle spinning (MAS) experiment. A proton decoupling field of approximately 85 kHz was applied during acquisition. A minimum of 128 scans were collected with a recycle delay of approximately 30 seconds. The fluorine spectrum was referenced using an external standard of trifluoroacetic acid (50% V/V in H$_2$O), setting its resonance to −76.54 ppm.

Example 24

Characterization of the 1R:1S-Camsylate Salt and the 1R:9S-Camsylate Salt by Solid State Nuclear Magnetic Resonance (SSNMR)

Approximately 80 mg of each sample was tightly packed into a 4 mm ZrO$_2$ rotor. Spectra were collected at ambient conditions on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The $^{13}$C solid state spectra, as shown in FIGS. 30 and 32, were collected using a proton decoupled cross-polarization magic angle spinning (CPMAS) experiment. The cross-polarization contact time was set to 2.0 ms. A proton decoupling field of approximately 85 kHz was applied during acquisition. A minimum of 2048 scans were collected with a 6 second recycle delay. The carbon spectra were referenced using an external standard of crystalline adamantane, setting its upfield resonance to 29.5 ppm. The $^{19}$F solid state spectra, as shown in FIGS. 31 and 33, were collected using a proton decoupled magic angle spinning (MAS) experiment. A proton decoupling field of approximately 85 kHz was applied during acquisition. A minimum of 128 scans were collected with a recycle delay of approximately 30 seconds. The fluorine spectra were referenced using an external standard of trifluoroacetic acid (50% V/V in H$_2$O), setting its resonance to −76.54 ppm.

Example 25

Characterization of Salts and Polymorphs of Compound 1 by Fourier Transform-Infrared Spectroscopy (FT-IR)

The IR spectra were acquired using a ThermoNicolet Nexus FTIR spectrometer equipped with a 'DurasampIIR' single reflection ATR accessory (diamond surface on zinc selenide substrate) and d-TGS KBr detector. The spectra were collected at 2 cm$^{-1}$ resolution and a co-addition of 512 scans. Happ-Genzel apodization was used. Because the FT-IR spectra were recorded using single reflection ATR, no sample preparation was required. Using ATR FT-IR will typically cause the relative intensities of infrared bands to differ from those seen in a transmission FT-IR spectrum using KBr disc or nujol mull sample preparations. Due to the nature of ATR FT-IR, the bands at lower wavenumber are typically more intense than those at higher wavenumber. Experimental error, unless otherwise noted, was ±2 cm$^{-1}$.

Example 26

Characterization of Salts and Polymorphs of Compound 1 by Fourier Transform-Raman Spectroscopy (FT-Raman)

The Raman spectra were collected using a Bruker Vertex70 FT-IR spectrometer with RamII Raman module equipped with a 1064 nm NdYAG laser and LN-Germanium detector. All spectra were recorded using 2 cm$^{-1}$ resolution and Blackman-Harris 4-term apodization. The laser power was 250 mW and 1024 scans were co-added.

Example 27

Preparation of the Amorphous Form of the S-Camsylate Salt of Compound 1

A solution of S-Camsylate polymorph Form A (150 mg) was prepared in tBA:water (50 ml; 60:40% v/v) at room temperature. The solution was frozen by swirling on dry ice-acetone bath over a 4-5 minute period to obtain a thick frozen layer on the sides of the sample flask. The condenser of the lyophilizer was cooled to −100° C. and vacuum was switched on. Sample flask with frozen solution was quickly attached to the port of a manifold or drying chamber. The vacuum was created by opening the vent to the chamber. The amorphous form of the S-camsylate salt of Compound 1 was isolated after overnight drying at room temperature.

Example 28

Characterization of the Amorphous Form of the S-Camsylate Salt of Compound 1 by Powder X-ray Diffraction (PXRD)

The powder X-ray diffraction pattern was obtained using a Bruker-AXS Ltd. D4 powder X-ray diffractometer fitted with an automatic sample changer, a theta-theta goniometer, automatic beam divergence slit, and a LynxEye detector. The sample was prepared for analysis by mounting on a low background cavity silicon wafer specimen mount. The specimen was rotated while being irradiated with copper K-alpha$_1$ X-rays (wavelength=1.5406 Ångstroms) with the X-ray tube operated at 40 kV/40 mA. The analysis were performed with the goniometer running in continuous mode set for a 0.3 second count per 0.020° step over a two theta range of 3° to 40°. The PXRD diffractogram, as shown in FIG. 34, exhibits a broad peak having a base that extends from about 5° 2θ to about 40° 2θ.

Example 29

Characterization of the Amorphous Form of the S-Camsylate Salt of Compound 1 by Solid State Nuclear Magnetic Resonance (SSNMR)

Approximately 80 mg of sample was tightly packed into a 4 mm ZrO$_2$ rotor. Spectra were collected on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The rotor was cooled with a direct stream of nitrogen having an output temperature of 0° C. The $^{13}$C solid state spectrum, as shown in FIG. 35, was collected using a proton decoupled cross-polarization magic angle spinning (CP-MAS) experiment. The cross-polarization contact time was set to 2.0 ms. A proton decoupling field of approximately 85 kHz was applied during acquisition. 10240 scans were collected with a 5.5 second recycle delay. The carbon spectrum was referenced using an external standard of crystalline adamantane, setting its upfield resonance to 29.5 ppm. The $^{19}$F solid state spectrum, as shown in FIG. 36, was collected using a proton decoupled magic angle spinning (MAS) experiment. A proton decoupling field of approximately 85 kHz was applied during acquisition. 512 scans were collected with a recycle delay of 5.5 seconds. The fluorine spectrum was referenced using an external standard of trifluoroacetic acid (50% V/V in H$_2$O), setting its resonance to −76.54 ppm.

Example 30

Characterization of the Amorphous Form of the S-Camsylate Salt of Compound 1 by Raman Spectroscopy Raman spectra were collected using a Nicolet NXR FT-Raman accessory attached to the FT-IR bench. The spectrometer was equipped with a 1064 nm Nd:YAG laser and a liquid nitrogen cooled Germanium detector. Prior to data acquisition, instrument performance and calibration verifications were conducted using polystyrene. Samples were analyzed in glass NMR tubes that were spun during spectral collection. The spectra were collected using 0.5 W of laser power and 100 co-added scans. The collection range was 3700-300 cm$^{-1}$. All spectra were recorded using 4 cm$^{-1}$ resolution and Happ-Genzel apodization.

Two separate spectra were recorded for each sample, which were subsequently averaged and intensity normalized prior to peak picking. Peaks were manually identified using the Thermo Nicolet Omnic 7.3a software. Peak position was picked at the peak maximum, and peaks were only identified as such, if there was a slope on each side; shoulders on peaks were not included. The peak position was rounded to the nearest whole number.

Example 31

Characterization of the Amorphous Form of the S-Camsylate Salt of Compound 1 by Differential Scanning calorimetry (DSC)

Differential Scanning calorimetry (DSC), as shown in FIG. 38, was performed with a TA DSC (Q1000) Samples of approximately 5 mg were weighed into Perkin Elmer hermetic aluminum pans (40 µl). Glass transition temperature (Tg) measurement was conducted at 2° C./minute heating rate with 1° C. amplitude and 100 seconds frequency in the −50 to 200° C. The nitrogen purge was 50 mL/minute unless otherwise noted. The temperature was calibrated using indium.

The Tg of 156.5° C. obtained is the midpoint of the step transition at half height in the reversing signal. Tg can change as a function of water and or solvent content.

We claim:
1. A crystalline camsylate salt of 8-fluoro-2-{4-[(methylamino)methyl]phenyl}-1,3,4,5-tetrahydro-6H-azepino[5,4,3-cd]indol-6-one.
2. The salt of claim 1, wherein the salt is a crystalline anhydrous salt.
3. The salt of claim 1, wherein the camsylate is S-camsylate.
4. The salt of claim 1, wherein the camsylate is R-camsylate.
5. The salt of claim 1, wherein the salt has a powder X-ray diffraction pattern comprising one or more or two or more or three peaks at diffraction angles (2θ) selected from the group consisting of 12.2±0.2, 14.8±0.2 and 22.4±0.2, wherein said powder X-ray diffraction pattern is obtained using copper K-alpha$_1$ X-rays at a wavelength of 1.5406 Ångstroms.
6. The salt of claim 1, wherein the salt has a solid state NMR spectrum comprising one or more $^{13}$C chemical shifts selected from the group consisting of 213.4±0.2, 171.8±0.2, and 17.3±0.2 ppm.
7. The salt of claim 1, wherein the salt has a solid state NMR spectrum comprising one or more $^{19}$F chemical shifts selected from the group consisting of −118.9±0.2 and −119.7 ppm±0.2.
8. The salt of claim 1, wherein the salt has a powder X-ray diffraction pattern comprising one or more or two or more or three peaks at diffraction angles (2θ) selected from the group consisting of 12.2±0.2, 14.8±0.2 and 22.4±0.2 obtained using copper K-alpha$_1$ X-rays at a wavelength of 1.5406 ÅÅngstroms; a solid state NMR spectrum comprising one or more or two or more or three $^{13}$C chemical shifts selected from the group consisting of 213.4±0.2, 171.8±0.2, and 17.3±0.2 ppm; and a solid state NMR spectrum comprising one or more or two $^{19}$F chemical shifts selected from the group consisting of −118.9±0.2 and −119.7 ppm±0.2.
9. The salt of claim 1, wherein the salt is a substantially pure polymorph of S-camsylate polymorph Form A.
10. The salt of claim 1, wherein the salt is a substantially pure polymorph of S-camsylate polymorph Form B or a substantially pure polymorph of S-camsylate polymorph Form C.
11. A crystalline maleate salt of 8-fluoro-2-{4-[(methylamino)methyl]phenyl}-1,3,4,5-tetrahydro-6H-azepino[5,4,3-cd]indol-6-one.
12. The salt of claim 11, wherein the salt is a crystalline anhydrous salt.
13. The salt of claim 11, wherein the salt has a powder X-ray diffraction pattern comprising peaks at diffraction angles (2θ) 6.0±0.2, 20.3±0.2, and 21.7±0.2, wherein said powder X-ray diffraction pattern is obtained using copper K-alpha$_1$ X-rays at a wavelength of 1.5406 Ångstroms.
14. The salt of claim 11, wherein the salt is a substantially pure polymorph of maleate polymorph Form A.
15. The salt of claim 11, wherein the salt has a powder X-ray diffraction pattern comprising peaks at diffraction angles (2θ) of 7.5±0.2, 11.3±0.2, and 24.3±0.2, wherein said powder X-ray diffraction pattern is obtained using copper K-alpha$_1$ X-rays at a wavelength of 1.5406 Ångstroms.
16. The salt of claim 11, wherein the salt has a solid state NMR spectrum comprising one or more $^{13}$C chemical shifts selected from the group consisting of 171.3±0.2, 112.4±0.2, and 43.8±0.2 ppm.
17. The salt of claim 11, wherein the salt has a solid state NMR spectrum comprising a $^{19}$F chemical shift at −123.1 ppm±0.2.
18. The salt of claim 11, wherein the salt has a powder X-ray diffraction pattern comprising: one or more or two or more or three peaks at diffraction angles (2θ) selected from the group consisting of 7.5±0.2, 11.3±0.2, and 24.3±0.2 obtained using copper K-alpha$_1$ X-rays at a wavelength of 1.5406 Ångstroms; a solid state NMR spectrum comprising one or more or two or more or three $^{13}$C chemical shifts selected from the group consisting of 171.3±0.2, 112.4±0.2, and 43.8±0.2 ppm; and a solid state NMR spectrum comprising a $^{19}$F chemical shift at −123.1±0.2 ppm.

19. The salt of claim 11, wherein the salt is a substantially pure polymorph of maleate polymorph Form B.

20. A pharmaceutical composition comprising the salt of claim 1 and a pharmaceutically acceptable carrier.

21. A pharmaceutical composition comprising the salt of claim 11 and a pharmaceutically acceptable carrier.

* * * * *